(12) United States Patent
Enoki et al.

(10) Patent No.: US 6,525,082 B1
(45) Date of Patent: Feb. 25, 2003

(54) APOPTOSIS INDUCER

(75) Inventors: Tatsuji Enoki, Otsu (JP); Nobuto Koyama, Otsu (JP); Katsushige Ikai, Otsu (JP); Ikunoshin Kato, Otsu (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/581,087

(22) PCT Filed: Dec. 8, 1998

(86) PCT No.: PCT/JP98/05554

§ 371 (c)(1),
(2), (4) Date: Jun. 9, 2000

(87) PCT Pub. No.: WO99/29647

PCT Pub. Date: Jun. 17, 1999

(30) Foreign Application Priority Data

| Dec. 11, 1997 | (JP) | 9-361644 |
| Dec. 19, 1997 | (JP) | 9-364356 |
| Dec. 22, 1997 | (JP) | 9-364813 |
| Jan. 14, 1998 | (JP) | 10-017660 |
| Mar. 9, 1998 | (JP) | 10-073018 |

(51) Int. Cl.[7] ............ A61K 31/415; C07D 233/64
(52) U.S. Cl. ............ 514/399; 514/396; 548/345.1
(58) Field of Search ............... 514/396, 399; 548/345.1

(56) References Cited

U.S. PATENT DOCUMENTS

3,381,691 A    5/1968   Schumacher et al.
5,443,596 A    8/1995   Junino et al.

FOREIGN PATENT DOCUMENTS

| JP | 56-102851 | 8/1981 |
| WO | 98/39291 | 9/1998 |
| WO | 98/40346 | 9/1998 |

OTHER PUBLICATIONS

Arnau et al., J. Heterocycl. Chem., 34(1), p. 233–239 (1997).
Saville–Stones et al., J. Chem. Soc., Perkin Trans. 1, (10), p. 2603–2604 (1991).
Sakai et al, Journal of Pesticide Science, 18(3), p. 217–223 (1993).
Norris et al, Can. J. Chem., 55(10), p. 1687–1695 (1977).
Groenneberg et al., Acta Chem. Scand., 26(5), p. 1847–1850 (1972).

*Primary Examiner*—Jerome D. Goldberg
(74) *Attorney, Agent, or Firm*—Wenderoth, Lind & Ponack, L.L.P.

(57) ABSTRACT

A substance for inducing apoptosis represented by specific formulae. A pharmaceutical composition which can be used for an anticancer agent containing said substance.

2 Claims, 39 Drawing Sheets

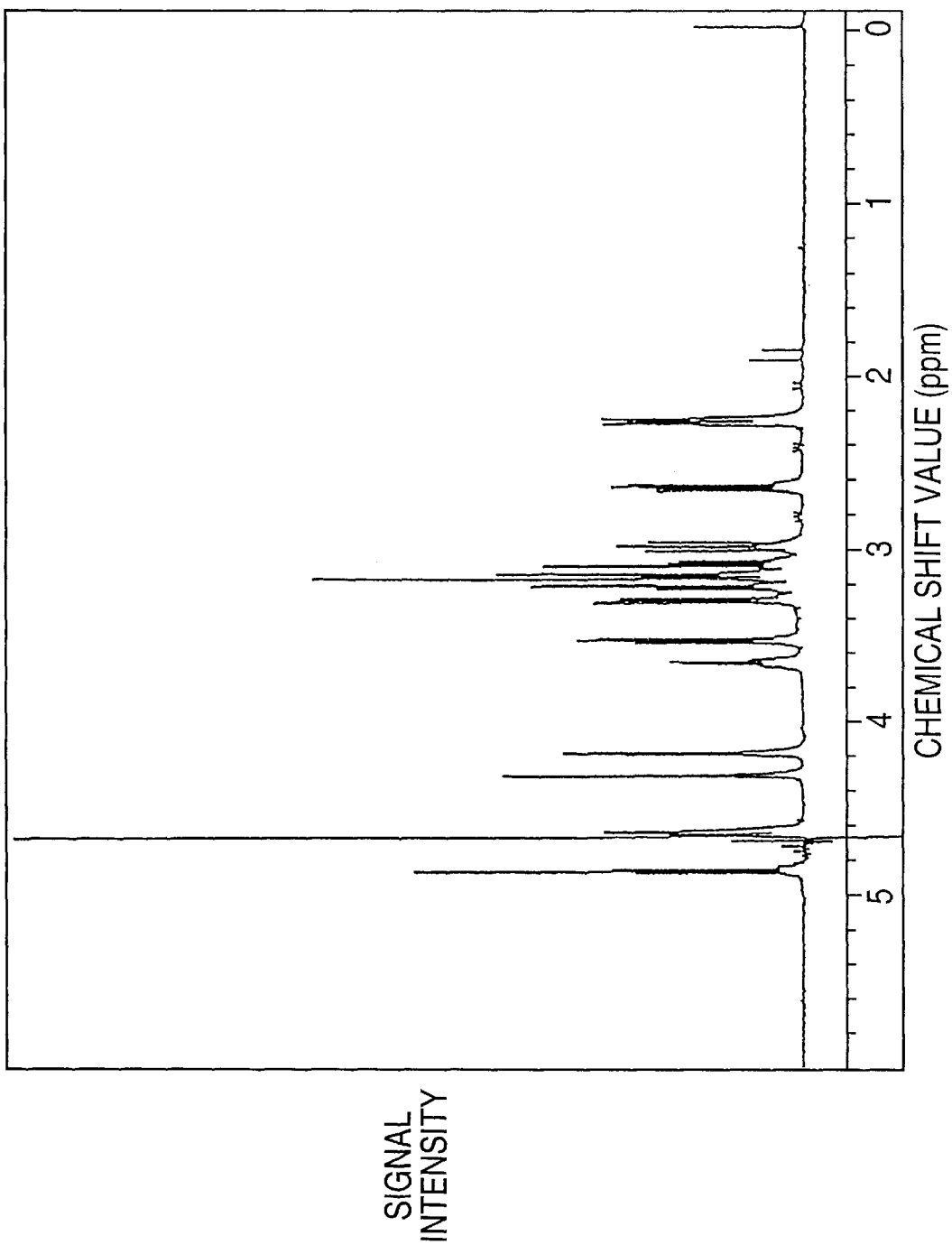

APOPTOSIS INDUCER

This application is a 371 of PCT/JP98/05554 filed Dec. 8, 1998.

TECHNICAL FIELD

The present invention relates to a substance for inducing apoptosis useful in the field of pharmaceuticals having a physiological activity such as anticancer action and use thereof.

PRIOR ART

In recent years, a mode of apoptosis has been drawing the attention concerning the death of cell tissues.

Unlike necrosis which is a pathological cell death, apoptosis is a death which is initially programmed in the gene of the cell itself. Thus, the gene which programs the apoptosis is activated by certain external or internal causes whereby programmed cell death gene protein is produced based upon said gene and then the cell itself is decomposed and dead by the resulting programmed death protein.

If such apoptosis can be expressed in desired tissues or cells, it will be now possible to exclude the unnecessary or harmful cells from living body in their natural form and that will be significantly meaningful.

PROBLEMS TO BE SOLVED BY THE INVENTION

Pharmaceuticals which have been used in clinical therapy include many agents such as anticancer agents, antibiotic substances, immunopotentiators, immunomodulators, etc. (such as alkylating agents, antimetabolites and plant alkaloids) but it can be hardly said that such a drug therapy has been completely established already.

An object of the present invention is to develop the highly-safe substance having a physiological function such as apoptosis-inducing action, etc. and to offer a method for the manufacture of said substance and pharmaceuticals containing said substance.

MEANS TO SOLVE THE PROBLEMS

The present invention will be summarized to be as follows. Thus, the first feature of the present invention relates to a substance for inducing apoptosis represented by the respective following formulae [I]–[VIII] or an optically active substance or a salt thereof.

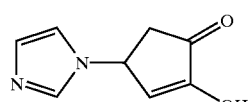
[I]

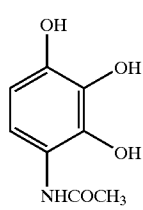
[II]

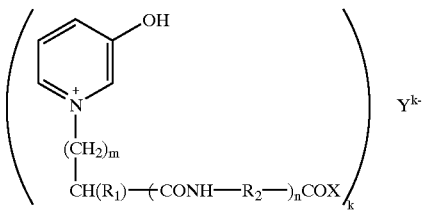
[III]

(In the formula [III], $R_1$ is H, an amino group, a lower alkyl group or a lower alkyl group having a substituent in an amino acid; $R_2$ is a divalent residue after removal of carboxyl group and amino group participating in a peptide bond in an amino acid; X is $O^-$ or an amino group; $Y^{k-}$ is an anion having valence(s) of k; m is an integer of 0–4; n is 0 or a positive integer; k is a positive integer; and when n is 2 or more, two or more $R_2$ existing therein may be same or different while, when X is $O^-$, the substance is an inner salt whereby $Y^{k-}$ does not exist.)

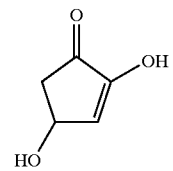
[IV]

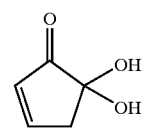
[V]

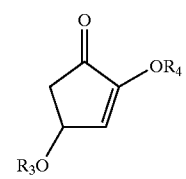
[VI]

(In the formula [VI], $R_3$ and $R_4$ may be same or different and each is an alkyl group having 1–3 carbons.)

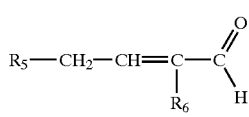
[VII]

(In the formula [VII], $R_5$ and $R_6$ may be same or different and each is an aromatic ring of an aromatic amino acid.)

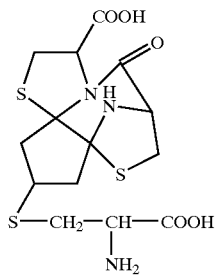

[VIII]

The second feature of the present invention relates a pharmaceutical composition which is characterized in containing the substance for inducing apoptosis, an optically active substance or a salt thereof of the first feature of the present invention.

In a preferred embodiment of the second feature of the present invention, said pharmaceutical composition is an anticancer agent.

BRIEF EXPLANATION OF THE DRAWINGS

FIG. 39 shows a $^1$H-NMR spectrum of LCD2.

EMBODIMENTS OF THE INVENTION

Figure 1:
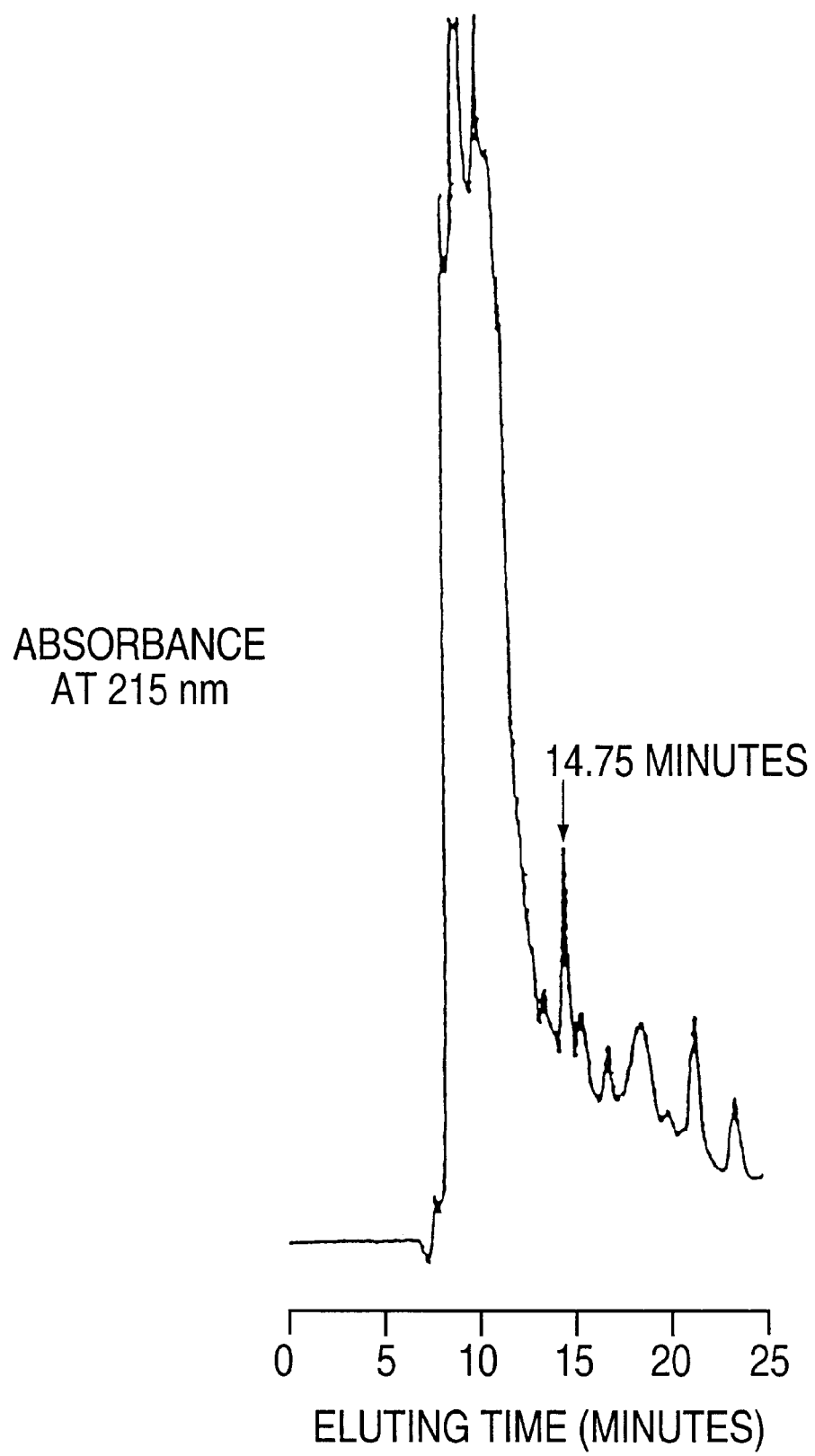
FIG. 1 shows an elution pattern of reverse phase HPLC of the imidazolylcyclopentenone.

The present invention will now be specifically illustrated as hereinafter.

First of all, the present inventors have found that 2-hydroxy-4-(1-imidazolyl)-2-cyclopenten-1-one represented by the formula [I] (hereinafter, referred to as just "imidazolylcyclopentenone") is produced by the reaction of 4,5-dihydroxy-2-cyclopenten-1-one (hereinafter, referred to as just "cyclopentenone") represented by the formula [IX] with imidazole and that said imidazolylcyclopentenone has an apoptosis-inducing action and a strong activity of growth inhibition of cancer cells.

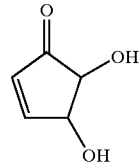

[IX]

Thus, the present invention offers a method for the manufacture of 2-hydroxy-4-(1-imidazolyl)-2-cyclopenten-1-one represented by the formula [I], an optically active substance or a salt thereof which is characterized in being produced by the reaction of cyclopentenone represented by the formula [IX], an optically active substance or a salt thereof with imidazole.

Cyclopentenone represented by the formula [IX] used in the present invention may be manufactured by the method disclosed in the present invention or by a chemical synthetic method [Carbohydrate Research, volume 247, pages 217–222 (1993); Helvetica Chimica Acta, volume 55, pages 2838–2844 (1972)]. Further, the compound which is produced in the heat-treated substance of at least one selected from uronic acid, uronic acid derivative(s), a saccharide compound containing uronic acid, a saccharide compound containing uronic acid derivative(s), a substance which contains a saccharide compound containing uronic acid and a substance which contains a saccharide compound containing uronic acid derivative(s) [refer to an article of the 56th Annual Meeting of the Japanese Cancer Association, page 599 (1997) and PCT/JP97/03052] (in the present invention, the heat-treated substance thereof) as well as purified product may be used as well.

The polysaccharides which are saccharide compounds containing uronic acid and/or uronic acid derivative(s) can be manufactured by known chemical, enzymatic or physical methods. For example, commercially available pectin or alginic acid may be used. Uronic acid, uronic acid derivatives, oligosaccharides, etc. which are synthesized by a synthetic means may be used in the present invention as well.

For example, when D-glucuronic acid is used as a uronic acid and its 1% solution is heated at 121° C. for four hours, the cyclopentenone represented by the formula [IX] is produced in the heat-treated substance. The cyclopentenone in this heat-treated substance is extracted with a solvent and the extract is concentrated. Then, this concentrated extract is separated by means of a silica gel column chromatography, the eluted cyclopentenone fraction is concentrated, the cyclopentenone is extracted with chloroform from the concentrate and the extract of the concentrate is subjected to a normal phase column chromatography whereupon the cyclopentenone in the heat-treated substance is isolated.

When the isolated cyclopentenone is subjected to an optical resolution, (−)-4,5-dihydroxy-2-cyclopenten-1-one and (+)-4,5-dihydroxy-2-cyclopenten-1-one are obtained. It goes without saying that the cyclopentenone obtained by a synthetic method can be subjected to an optical resolution as well.

Separation of the optically active substances can be conducted by subjecting the racemic mixture to mechanical resolution, preferential crystallization, resolution by crystallization as diastereomer salts or as inclusion compounds, dynamic resolution using enzymes or microorganism, resolution by means of chromatography, etc.

Gas chromatography, liquid chromatography, thin layer chromatography, etc. may be used in the case of a resolution by chromatography and a chiral stationary phase which is suitable for each of them may be used. A method using a chiral stationary phase, a method using a chiral eluate, separation as a diastereomer, etc. may be used in an optical resolution by liquid chromatography. A stationary phase of an amide type, that of a urea type, that of a ligand exchange type, polysaccharide-polysaccharide derivative stationary phase, protein stationary phase, polymethacrylate stationary phase, polymethacrylamide stationary phase, etc. may be used as a chiral stationary phase. With regard to an eluting liquid, that of a hexane type, an alcohol type, an aqueous (buffer) type, etc. may be suitably used taking the combination with the above-mentioned stationary phase into consideration.

For example, the cyclopentenone is dissolved in ethanol. To this ethanolic solution is further added hexane/ethanol (94/6) to prepare a cyclopentenone solution. The cyclopentenone can be optically resolved when this sample solution is subjected to an HPLC using, for example, a Chiral Pack AS (manufactured by Daicel Chemical Industries) under such a condition that the column temperature was 40° C. and the mobile phase was hexane/ethanol (94/6).

Conditions for Optical Resolution HPLC.

Columns: Chiral Pack AS (manufactured by Daicel) 2.0 cm×25.0 cm

Column temperature: 40° C.

Mobile phase: hexane/ethanol (94/6)

Flow rate: 14.0 ml/minute

Detection: UV 210 nm

Amount of the charged sample: 150 µl (2.55 mg)

Optical rotation of the optically resolved (−)-trans-4,5-dihydroxy-2-cyclopenten-1-one [hereinafter, referred to as (−)-cyclopentenone] is $[\alpha]_{D20}$ −105° (c 0.30, ethanol) while that of the optically resolved (+)-trans-4,5-dihydroxy-2-cyclopenten-1-one [hereinafter, referred to as (+)-cyclopentenone] is $[\alpha]_{D20}$ +104° (c 0.53, ethanol). Incidentally, the optical rotation was measured by the above-mentioned polarimeter of the type DIP-370 (manufactured by Nippon Bunko). The eluting times in above optical resolution HPLC of the (−)-cyclopentenone and (+)-cyclopentenone are 33 minutes and 40 minutes, respectively.

When the cyclopentenone or its optically active substance or a salt thereof is made to react with imidazole, the imidazolylcyclopentenone represented by the formula [I] of the present invention or its optically active substance or a salt thereof is produced in the reaction solution. With regard to imidazole, a commercially available substance may be used or it may be synthesized from glyoxal, formalin and ammonia or by a decarboxylation of imidazole-4,5-dicarboxylic acid.

Reaction of the cyclopentenone or its optically active substance or a salt thereof with imidazole is preferably carried out usually at a neutral pH.

The imidazolylcyclopentenone or its optically active substance or a salt thereof produced by the reaction of the cyclopentenone or its optically active substance or a salt thereof with imidazole has a strong activity of growth inhibition of cancer cells and, using the said activity as an index, the imidazolylcyclopentenone or its optically active substance or a salt thereof can be purified and isolated from the reaction solution. With regard to the purifying and isolating means, known purifying means such as a chemical method and a physical method may be used and the conventionally known purifying methods such as gel filtration, fractionation using molecular weight fractionating membrane, extraction with solvent, fractional distillation and various chromatographic methods using ion-exchange resin, etc. may be combined whereby the imidazolylcyclopentenone or its optically active substance or a salt thereof in the reaction product can be purified and isolated.

For example, when the cyclopentenone is made to react with imidazole at 37° C. for one hour, the imidazolylcyclopentenone represented by the formula [I] is produced in the reaction solution and, when the reaction product containing the said derivative is subjected to a normal phase column chromatography, the imidazolylcyclopentenone can be purified and isolated and, in addition, an optically active substance can be obtained by its optical resolution.

With regard to a salt of the imidazolylcyclopentenone, there is a pharmaceutically acceptable salt. Its examples are hydrochloride, sulfate, acetate, sodium salt, potassium salt and ammonium salt and a conversion thereto can be done by a known method.

The present inventors have then found that, when N-acetylhexosamine dialdose or a derivative thereof is heated, N-(2,3,4-trihydroxyphenyl)acetamide represented by the formula [II] is produced and that this substance has an apoptosis-inducing action and a strong activity of growth inhibition of cancer cells.

Thus, in accordance with the present invention, there is provided a method for the manufacture of N-(2,3,4-trihydroxyphenyl)acetamide or a salt thereof which is characterized in including a step of heating an N-acetylhexosamine dialdose or a derivative thereof.

An example of the said manufacturing method is a method for the manufacture of N-(2,3,4-trihydroxyphenyl) acetamide or a salt thereof in which the N-acetylhexosamine dialdose or a derivative thereof is N-acetyl-D-galactosamine dialdose represented by the following formula [X] or its antipode or a derivative thereof.

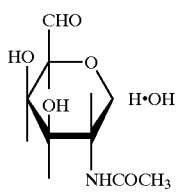

N-Acetylhexosamine dialdose is an aldehyde in which a 6-position of N-acetylhexosamine is oxidized and its molecular formula is $C_8H_{13}NO_6$ and its molecular weight is 219.19.

N-Acetylhexosamine dialdose may, for example, be manufactured by oxidation of the 6-position of N-acetylhexosamine either chemically or enzymatically. An example of the chemical oxidation is a Fenton method where oxidation is carried out with hydrogen peroxide in the presence of a ferrous salt while that of the enzymatic oxidation is an oxidation using galactose oxidase [EC 1.1.3.9; Cooper, et al.; *The Journal of Biological Chemistry*, volume 234, pages 445–448 (1959)]. Oxidation of N-acetyl-D-galactosamine with galactose oxidase gives N-acetylgalactosamine dialdose.

Examples of N-acetylhexosamine dialdose are esters and ethers and all substances wherefrom N-(2,3,4-trihydroxyphenyl)acetamide (hereinafter, referred to as the trihydroxyacetamide) is produced by a heating treatment are covered by the present invention. Examples of an ester of N-acetylhexosamine dialdose are acetate, formate, sulfate and phosphate and they can be manufactured from N-acetylhexosamine dialdose. It is also possible to prepare an ether compound by etherification and such an ether compound can be used in the present invention. A compound which contains N-acetylhexosamine dialdose and/or a derivative thereof may be used in the present invention as well.

With regard to the N-acetylhexosamine dialdose of the present invention and a derivative thereof, there is no particular limitation so far as trihydroxyphenylacetamide represented by the formula [II] is produced in the heat-treated product.

Trihydroxyphenylacetamide has a strong activity of growth inhibition of cancer cells and it is possible to purify and isolate the trihydroxyphenylacetamide from the reaction solution using the said activity as an index. With regard to the purifying and isolating means, known purifying means such as a chemical method and a physical method may be used and the conventionally known purifying methods such as gel filtration, fractionation using molecular weight fractionating membrane, extraction with solvent, fractional distillation and various chromatographic methods using ion-exchange resin, etc. may be combined whereby the trihydroxyphenylacetamide in the reaction product can be purified and isolated.

For example, when N-acetylhexosamine dialdose is made to react at 121° C. for 4 hours, trihydroxyphenylacetamide represented by the formula [II] is produced in the reaction solution and, when the reaction product containing the derivative is subjected to a reverse phase column chromatography, the trihydroxyphenylacetamide can be purified and isolated.

With regard to a salt of the trihydroxyphenylacetamide, there is a pharmaceutically acceptable salt. Its examples are the salts with alkaline metals such as sodium and potassium and a conversion thereto can be carried out by a known method.

The present inventors have then found that, when at least one substance selected from the following (a1), (a2) and (a3) is heated in the presence of a compound represented by the formula [XI], a 3-hydroxy-1-substituted pyridinium salt represented by the formula [III] (hereinafter, called as the substituted pyridinium salt) is produced and that the said substance has an apoptosis-inducing action and an activity of growth inhibition of cancer cells.

(a1): uronic acid or uronic acid derivative(s),
(a2): a saccharide compound which contains uronic acid and/or uronic acid derivative(s), and
(a3): a substance containing a saccharide compound which contains uronic acid and/or uronic acid derivative(s);

(In the formula [XI], $R_7$ is H, an amino group, a lower alkyl group or a lower alkyl group having a substituent in an amino acid; $R_8$ is a divalent residue after removal of carboxyl group and amino group participating in a peptide bond in an amino acid; X is OH or an amino group; m is an integer of 0–4; n is 0 or a positive integer; and when n is 2 or more, two or more $R_8$ existing therein may be same or different.)

Thus, in accordance with the present invention, there is provided a method for the manufacture of a 3-hydroxy-1-substituted pyridinium salt represented by the formula [III] or an optically active substance thereof which is characterized in that at least one substance selected from the above (a1), (a2) and (a3) is heated in the presence of a compound represented by the formula [XI] or a derivative thereof.

Uronic acid is sometimes called glycuronic acid and is a general name for hydroxyaldehyde carboxylic acids in which an aldehyde group on aldose remains as it is while only a primary alcohol group at another end is oxidized to a carboxyl group. It is present in nature as a constituting component for various polysaccharides of animals and plants.

There is no particular limitation for the uronic acid used in the present invention. Thus, examples of the uronic acid are galacturonic acid, glucuronic acid, guluronic acid, mannuronic acid, iduronic acid and salts etc. of the above-mentioned ones while examples of the uronic acid derivative(s) are lactones, esters, amides, salts, etc. of the above-mentioned ones and any substance. Examples of the uronic acid lactone are glucurono-6,3-lactone, mannurono-6,3-lactone and idurono-6,3-lactone.

Examples of the uronic acid ester are methyl, ethyl, propylene glycol and carboxymethyl uronates which can be manufactured from uronic acid. Uronic acid amide can be manufactured by amidation of uronic acid. Salts of them can be manufactured by common methods.

There is no particular limitation for the saccharide compound containing uronic acid and/or uronic acid derivative(s) in this specification and the examples applicable are pectin, pectic acid, alginic acid, hyaluronic acid, heparin, fucoidan, chondroitin sulfate, chondroitin and dermatan sulfate including decomposed products, derivatives of the decomposed products and salts of the decomposed products thereof which are chemically, enzymatically or physically-treated products thereof.

With regard to the compound represented by the formula [XI] used in the present invention, there is no particular limitation so far as it is heated with at least one substance selected from the above (a1), (a2) and (a3) or, preferably, with glucuronic acid to give a substituted pyridinium salt represented by the formula [III].

The type of the compound represented by the formula [XI] may be appropriately selected depending upon the types of $R_7$, $R_8$ and X and the values of m and n in the formula [III] which is an aimed substituted pyridinium salt and/or an optically active substance thereof. With regard to a compound represented by the formula [XI], an α-amino acid may be used for example while, with regard to an amino acid containing an asymmetric carbon atom, its L-substance, D-substance and a mixture thereof may be used. With regard to the compound represented by the formula [XI], β-amino acid, oligopeptide, polypeptide or glycopeptide, for example, may be used in addition to an α-amino acid. It is also possible to use derivatives thereof such as salt, ester, amide, lactone and lactam.

In the present invention, a substance containing a compound represented by the formula [XI] may be used as well.

When a substance selected from the above (a1), (a2) and (a3) is heated in the presence of a compound represented by the formula [XI], a substituted pyridinium salt or an optically active substance thereof is produced. There is no particular limitation for the reaction conditions such as concentrations of the substance selected from the above (a1), (a2) and (a3) and the compound represented by the formula [XI] upon heating, pH, heating temperature, heating time, etc. so far as the condition is that whereby the substituted pyridinium salt or an optically active substance thereof is produced.

The resulting substituted pyridinium salt has a positive charge in its pyridine ring and forms an inner salt when X in the formula [III] is O⁻ while, when it is an amino group, a salt is formed together with a monovalent anion. In addition, a multivalent anion forms a salt with plural substituted pyridinium salt as well and such a salt is also covered by the present invention.

Further, each of the positive and the negative charges of the substituted pyridinium salt is able to form a salt with each counter ion. Such a salt is covered by the present invention as well.

The resulting substituted pyridinium salt or an optically active salt thereof can be purified and isolated by a known method using the activity of growth inhibition of cancer cells as an index. With regard to the purifying and isolating means, known purifying means such as a chemical method and a physical method may be used and the conventionally known purifying methods such as gel filtration, fractionation using molecular weight fractionating membrane, extraction with solvent, fractional distillation and various chromatographic methods using ion-exchange resin, etc. may be combined whereby the substituted pyridinium salt or its optically active substance or a salt thereof in the reaction product can be purified and isolated.

For example, when glucuronic acid is made to react with an aqueous solution of glycine at 121° C. for 30 minutes, 1-carboxymethyl-3-hydroxypyridinium inner salt (hereinafter, referred to as B-UG) represented by the formula [XII] is produced in the reaction solution. When the reaction product containing the said derivative is subjected to a silica column chromatography and a reverse phase column chromatography, the B-UG can be purified and isolated.

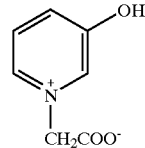

[XII]

When the purified substituted pyridinium salt is a racemic substance, it is subjected to an optical resolution by, for example, the above-mentioned method whereupon a (−)-substituted pyridinium salt and a (+)-substituted pyridinium salt can be obtained.

The present inventors have then found that a cyclopentenone derivative represented by the formula [VI] or an optically active substance thereof is produced when the cyclopentenone or an optically active substance thereof is made to react with an alcohol and, when the cyclopentenone derivative represented by the formula [VI] or an optically active substance thereof is treated with an acid, a composition consisting of 2,4-dihydroxy-2-cyclopenten-1-one represented by the formula [IV] and 5,5-dihydroxy-2-cyclopenten-1-one represented by the formula [V] is produced; that, when the cyclopentenone or an optically active substance thereof is treated with an acid, a composition consisting of 2,4-dihydroxy-2-cyclopenten-1-one represented by the formula [IV] and 5,5-dihydroxy-2-cyclopenten-1-one represented by the formula [V] is produced; and that the composition consisting of 2,4-dihydroxy-2-cyclopenten-1-one represented by the formula [IV] and 5,5-dihydroxy-2-cyclopenten-1-one represented by the formula [V] produced as such has a strong activity of growth inhibition of cancer cells and an apoptosis-inducing activity.

Thus, in accordance with the present invention, there is provided a composition consisting of 2,4-dihydroxy-2-cyclopenten-1-one represented by the formula [IV] and 5,5-dihydroxy-2-cyclopenten-1-one represented by the formula [V].

In accordance with the present invention, there is provided a method for the manufacture of the above-mentioned composition which is characterized in including a step where the cyclopentenone derivative represented by the formula [VI] or an optically active substance thereof is treated with an acid.

In accordance with the present invention, there is provided a method for the manufacture of the above-mentioned composition which is characterized in including a step where the cyclopentenone or an optically active substance thereof is treated with an acid.

In accordance with the present invention, there is provided a pharmaceutical composition which is characterized in containing the above-mentioned composition as an effective component.

In accordance with the present invention, there is provided a method for the manufacture of a cyclopentenone derivative represented by the formula [VI] or an optically active substance thereof which is characterized in including a step where the cyclopentenone or an optically active substance thereof is made to react with an alcohol having 1–3 carbon(s) or a reactive derivative thereof.

When the cyclopentenone and/or an optically active substance thereof are/is made to react with an alcohol, the cyclopentenone derivative of the present invention represented by the formula [VI] or an optically active substance thereof is produced in the reaction solution. Examples of the alcohol having 1–3 carbon(s) used in the present invention are methanol, ethanol, 1-propanol and 2-propanol. Reaction of the cyclopentenone and/or an optically active substance thereof with an alcohol is recommended to carry out usually under an acidic pH. Examples of the reactive derivative of the both materials are a salt such as a sodium salt, an acid halide and an active ester.

With regard to the purifying and isolating means for the resulting cyclopentenone derivative or an optically active substance thereof by the reaction of the cyclopentenone or an optically active substance thereof with an alcohol, known purifying means such as a chemical method and a physical method may be used and the conventionally known purifying methods such as gel filtration, fractionation using molecular weight fractionating membrane, extraction with solvent, fractional distillation and various chromatographic methods using ion-exchange resin, etc. may be combined whereby the cyclopentenone derivative or an optically active substance thereof in the reaction product can be purified and isolated.

When the cyclopentenone derivative represented by the formula [VI] is treated with an acid, a composition consisting of 2,4-dihydroxy-2-cyclopenten-1-one represented by the formula [IV] and 5,5-dihydroxy-2-cyclopenten-1-one represented by the formula [V] is produced. There is no particular limitation for the type and the concentration of acid, temperature upon the acid treatment and reaction time but the conditions whereby the above-mentioned reaction proceeds may be used. Examples of the acid used are inorganic acids such as hydrochloric acid, sulfuric acid and nitric acid and organic acids such as acetic acid, formic acid, citric acid, lactic acid and ascorbic acid.

For example, when the cyclopentenone is dissolved in a 5:95 mixture of 10N HCl and methanol and made to react at 37° C. for one night, the cyclopentenone derivative represented by the formula [VI] is produced in the reaction solution and, when the reaction product containing the said derivative is subjected to a reverse phase column chromatography, the cyclopentenone derivative can be purified and isolated.

When the cyclopentenone derivative represented by the formula [VI] is dissolved in 1 mM HCl and made to react at 37° C. for 16 hours, a composition consisting of 2,4-dihydroxy-2-cyclopenten-1-one represented by the formula [IV] and 5,5-dihydroxy-2-cyclopenten-1-one represented by the formula [V] is produced and, when a reaction product containing the above is subjected to a reverse phase column chromatography, a composition consisting of 2,4-dihydroxy-2-cyclopenten-1-one represented by the formula [IV] and 5,5-dihydroxy-2-cyclopenten-1-one represented by the formula [V] can be purified.

When the cyclopentenone is treated with an acid, a composition consisting of 2,4-dihydroxy-2-cyclopenten-1-one represented by the formula [IV] and 5,5-dihydroxy-2-cyclopenten-1-one represented by the formula [V] is produced. There is no particular limitation for the type and the concentration of acid, temperature upon the acid treatment and reaction time but the conditions whereby the above-mentioned reaction proceeds may be used. Examples of the acid used are inorganic acids such as hydrochloric acid, sulfuric acid and nitric acid and organic acids such as acetic acid, formic acid, citric acid, lactic acid and ascorbic acid.

For example, when the cyclopentenone is dissolved in 300 mM sulfuric acid and made to react at 100° C. for 4 hours, a composition consisting of 2,4-dihydroxy-2-cyclopenten-1-one and 5,5-dihydroxy-2-cyclopenten-1-one is produced. When this reaction mixture is subjected to a reverse phase HPLC, a composition consisting of 2,4-dihydroxy-2-cyclopenten-1-one and 5,5-dihydroxy-2-cyclopenten-1-one can be purified.

The present inventors have then found that, when at least one substance selected from the following (b1), (b2) and (b3) is heated in the presence of at least one substance selected from the above-mentioned (a1), (a2) and (a3), a compound represented by the formula [VII] or a salt thereof is produced and that the said substance has an activity of growth inhibition of cancer cells and an apoptosis-inducing action.

In accordance with the present invention, there is provided a method for the manufacture of a compound represented by the formula [VII] or a salt thereof which is characterized in that at least one substance selected from the following (b1), (b2) and (b3) is heated in the presence of at least one substance selected from the above-mentioned (a1), (a2) and (a3).

(b1): an aromatic amino acid
(b2): an aromatic amino acid derivative
(b3): a substance containing an aromatic amino acid and/or an aromatic amino acid derivative.

There is no particular limitation for the aromatic amino acid, the aromatic amino acid derivative and the substance containing the aromatic amino acid and/or the aromatic amino acid derivative used in the present invention so far as it/they give(s) the compound represented by the formula [VII] or a salt thereof when heated together with at least one of the above-mentioned (a1), (a2) and (a3).

Examples of the aromatic amino acid are tyrosine, phenylalanine, tryptophan, histidine, DOPA and dopamine and an L-substance, a D-substance and a mixture thereof may be used. With regard to the aromatic amino acid derivative, an oligopeptide containing the aromatic amino acid, a polypeptide containing the aromatic amino acid and a glycopeptide containing the aromatic amino acid may, for example, be used. It is also possible to use salt, ester, amide, lactone, lactam, etc. thereof.

In the present invention, a substance containing the aromatic amino acid and/or the aromatic amino acid derivative may be used as well.

When the above (a3) contains at least one substance selected from the above (b1) and (b2) or, when the above (b3) contains at least one substance selected from the above (a1), (a2) and (a3), it goes without saying that further addition of at least one substance selected from the above (b1), (b2) and (b3) or at least one substance selected from the above (a1), (a2) and (a3) prior to the heating treatment is not essential.

When at least one substance selected from the above (a1), (a2) and (a3) is heated in the presence of at least one substance selected from the above (b1), (b2) and (b3), a compound represented by the formula [VII] or a salt thereof is produced. There is no particular limitation for the conditions such as concentrations of at least one substance selected from the above (a1), (a2) and (a3) and of at least one substance selected from the above (b1), (b2) and (b3), pH, temperature, time, etc. upon heating so far as the condition is such a one that the said compound or a salt thereof is produced.

In the heating treatment, at least one substance selected from (a1), (a2) and (a3) acts as an oxidizing agent.

The resulting compound represented by the formula [VII] or a salt thereof can be purified and isolated by a known method using an activity of growth inhibition of cancer cells as an index. With regard to the purifying and isolating means, known purifying means such as a chemical method and a physical method may be used and the conventionally known purifying methods such as gel filtration, fractionation using molecular weight fractionating membrane, extraction with solvent, fractional distillation and various chromatographic methods using ion-exchange resin, etc. may be combined whereby the compound represented by the formula [VII] or a salt thereof in the reaction product can be purified and isolated.

For example, when glucuronic acid is made to react with an aqueous solution of tyrosine at 121° C. for 4 hours, 2,4-bis(p-hydroxyphenyl)-2-butenal represented by the formula [XIII] (hereinafter, referred to as S-1127) or a salt thereof is produced in the reaction solution. When the reaction product containing this compound is subjected to a silica gel column chromatography and a reverse phase column chromatography, it is possible to purify and isolate the S-1127 or a salt thereof.

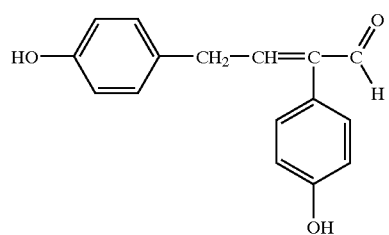

[XIII]

In the compound obtained by the present invention and represented by the formula [VII] or a salt thereof, the bond between the carbons of the positions 2 and 3 is a double bond whereby there are cis- and trans-compounds. The compound of the present invention represented by the formula [VII] or a salt thereof may be any of the cis- and trans-isomers or may be a mixture thereof.

With regard to a salt of the compound represented by the formula [VII] obtained in the present invention, there is a pharmaceutically-acceptable salt and its examples are sodium salt, potassium salt, ammonium salt, calcium salt and magnesium salt. Conversion thereto may be carried out by a known method.

The present inventors have then succeeded in the production of 9-cystein-S-yl-2-oxo-6,12-dithia-3,14-diazatetracyclo[9,2,1,03,7,07,11]tetradecane-4-carboxylic acid represented by the formula [VIII] (hereinafter, referred to as tCD) by the reaction of the cyclopentenone with cysteine and in isolation of this tCD whereupon the present invention has been accomplished.

Thus, in accordance with the present invention, there is provided a method for the manufacture of tCD or its optically active substance or a salt thereof which is characterized by the reaction of the cyclopentenone or an optically active substance thereof with cysteine.

The tCD, each diastereomer thereof or its optically active substance or a salt thereof produced by the reaction of the cyclopentenone or an optically active substance thereof with cysteine has an activity of growth inhibition of cancer cells and, using the said activity as an index, the tCD, each diastereomer thereof or its optically active substance or a salt thereof can be purified and isolated from the reaction solution. With regard to the purifying and isolating means, known purifying means such as a chemical method and a physical method may be used and the conventionally known purifying methods such as gel filtration, fractionation using molecular weight fractionating membrane, extraction with solvent, fractional distillation and various chromatographic methods using ion-exchange resin, etc. may be combined whereby the tCD, each diastereomer thereof or its optically active substance or a salt thereof in the reaction product can be purified and isolated.

For example, when the cyclopentenone is made to react with L-cysteine at 37° C. for one night, the tCD represented by the formula [VIII] is produced in the reaction solution and, when the reaction solution containing the said compound is subjected to a reverse phase column chromatography, the tCD can be purified and isolated.

With regard to a salt of the tCD, there is a pharmaceutically acceptable salt. Its examples are hydrochloride, sulfate, acetate, sodium salt, potassium salt and ammonium salt and conversion thereto may be carried out by a known method.

The compound selected from the substance for inducing apoptosis represented by the formula [I], [II], [III], [IV], [V], [VI], [VII] or [VIII] (hereinafter, referred to as just "the compound of the present invention"), an optically active substance thereof or a salt thereof has physiological activities such as anticancer activity, activity of growth inhibition of cancer cells, apoptosis-inducing activity, activity of topoisomerase II inhibition, induction activity of the cancer cell differentiation, antirheumatic activity, activity of chronic articular rheumatism inhibition, activity of inducing the Fas antigen production, antibacterial activity, antiviral activity, activity of improving the hepatic function, activity of inducing the heat shock protein, normalizing activity of the blood components, enhancer activity of the cancer immunity, anti-inflammation activity, inhibition activity of tumor necrosis factor expression, inhibition activity of nitrogen monoxide production, immunomodulating activity such as inhibition activity of delayed type hypersensitivity, inhibition activity of lymphocyte transformation, inhibition activity of mixed lymphocyte reaction, inhibition activity of IgE production and inhibition activity of carrageenan edema and, due to those activities, pharmaceutical agent containing as an effective component at least one compound which is selected from the compound of the present invention, an optically active substance thereof and a salt thereof is useful as a drug acting biophylaxic function such as pharmaceutical preparation acting the antibody production function, anti-inflammatory agent, antiallergic agent, antirheumatic agent and interferon inducer, a drug acting the saccharide metabolism such as remedy for diabetes mellitus and a drug acting the pathogenic organisms such as antibacterial agent and antiviral agent. Accordingly, the pharmaceutical agent obtained by the present invention is quite useful as a drug for the diseases which show sensitivity to the compound of the present invention, an optically active substance thereof or a salt thereof, i.e. as a pharmaceutical composition for therapy or prevention of, for example, cancer, viral diseases, rheumatism, diabetes mellitus, allergy, autoimmune diseases, inflammation, etc.

When at least one of the compound selected from the compound of the present invention, an optically active substance thereof or a salt thereof having various physiological actions is used as an effective component and is made into a pharmaceutical preparation by compounding with known pharmaceutical carriers, it is now possible to prepare a pharmaceutical composition.

The compound of the present invention, an optically active substance thereof or a salt thereof has a cell growth inhibiting action and anticancer action to cancer cells such as human promyelocytic leukemia cells HL-60, human acute lymphoblastic leukemia cells MOLT-3, pulmonary cancer cells A-549, SV40-transformed pulmonary cancer cells WI-38VA13, hepatoma cells Hep G2, colon cancer cells HCT 116, human colon cancer cells SW 480, human colon cancer cells WiDr, stomach cancer cells AGS and myeloma cells. Thus, the compound of the present invention, an optically active substance thereof or a salt thereof can be used as an effective component of anticancer agent. Further, those compounds have an apoptosis-inducing action to those cancer cells too. Mechanism of the action for inhibiting the cancer cell growth of the compound of the present invention, an optically active substance thereof or a salt thereof does not limit the scope of the present invention at all and, for example, a topoisomerase II inhibiting action and an apoptosis inducing action to cancer cells is covered by anticancer activity of the present invention as well.

When at least one of the compound selected from the compound of the present invention, an optically active substance thereof or a salt thereof having anticancer action is used as an effective ingredient and is made into a pharmaceutical preparation by compounding with known pharmaceutical carriers, it is now possible to prepare an anticancer agent. Generally, at least one of the compound selected from the compound of the present invention, an optically active substance thereof or a salt thereof is compounded with a pharmaceutically acceptable liquid or solid carrier and, if necessary, solvent, dispersing agent, emulsifier, buffer, stabilizer, filler, binder, disintegrating agent, lubricant, etc. are added thereto to give an anticancer agent which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where at least one of the compound selected from the compound of the present invention, an optically active substance thereof or a salt thereof which is an effective ingredient of the pharmaceutical composition according to the present invention is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The anticancer agent of the present invention is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as an anticancer agent is appropriately decided by its form of preparation, method of administration, purpose of use and age, body weight and symptom of the patient to be treated and it is not constant but, usually, the amount of at least one of the compound selected from the compound of the present invention, an optically active substance thereof or a salt thereof contained in the preparation is from 0.1 $\mu$g to 200 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The compound of the present invention, an optically active substance thereof or a salt thereof has an anticancer action and, at low concentrations, it shows an ability of inducing the differentiation of cancer cells whereby it is useful as a differentiation inducer (a decancerizing agent) for cancer cells. An inducer for cancer cell differentiation containing at least one of the compound selected from the compound of the present invention, an optically active substance thereof or a salt thereof as an effective ingredient can be made into pharmaceutical preparations in accordance with the above-mentioned method for anticancer agents and can be administered by the method similar to that for anticancer agents.

The above-mentioned inducer for cancer cell differentiation can be used in a method for induction of cancer cell differentiation. Thus, when at least one of the compound selected from the compound of the present invention, an optically active substance thereof or a salt thereof is used as an effective ingredient, it is possible to differentiate the cancer cells and such a method is useful for elucidation of mechanism for induction of cancer cell differentiation, for screening of the differentiation inducers, etc.

The compound of the present invention or an optically active substance thereof or a salt thereof has an antibacterial action and, when at least one compound selected from such compounds is used as an effective component and is made into a pharmaceutical preparation by combining with known pharmaceutical carriers, an antibacterial agent can be manufactured. Said pharmaceutical preparation can be manufactured by the same manner as in the case of the above-mentioned anticancer agent and can be administered by the same manner as in the case of the anticancer agent. Further, it may be used together with ethanol, glycine, sodium acetate, ascorbic acid, glycerol fatty acid esters, salt, EDTA and other antibiotic substances.

The apoptosis inducer of the present invention contains at least one of the compound selected from the apoptosis-inducing compound of the present invention, an optically active substance thereof or a salt thereof as an effective ingredient. It can be made into pharmaceutical preparations by the same manner as in the above-mentioned case of anticancer agents and is administered by the same manner as in the anticancer agents.

The dose as the apoptosis inducers is not particularly specified but may be appropriately determined depending upon the dosage form, administration method, purpose of the use and age, body weight, conditions, etc. of the patient to whom the inducer is administered. Usually, however, the amount of at least one of the compound selected from the compound of the present invention, an optically active substance thereof or a salt thereof contained in the preparation for an adult is 0.1 $\mu$g-100 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well.

Unlike necrosis which is a pathogenic death of cells, apoptosis is believed to be a death which is initially programmed in the gene of the cell itself. Thus, the gene which programs the apoptosis is activated by certain external or internal causes whereby programmed cell death gene protein is produced based upon said gene and then the cell itself is decomposed and dead by the resulting programmed death protein.

The apoptosis inducer of the present invention is quite useful since it is capable of induction of such apoptosis in desired tissues and cells and able to exclude the unnecessary cells or the pathogenic cells from living organisms in a natural state.

The apoptosis inducer of the present invention can be used in a method for the induction of apoptosis. Thus, when at least one of the compound selected from the compound of the present invention, an optically active substance thereof or a salt thereof is used as an effective ingredient, it is possible to induce apoptosis and said method is useful, for example, for elucidation of a mechanism for apoptosis induction and for screening of apoptosis inducers and apoptosis induction inhibitors.

The compound of the present invention or an optically active substance thereof or a salt thereof has an antirheumatic activity and, when at least one compound selected from such compounds is used as an effective component and is made into a pharmaceutical preparation by combining with known pharmaceutical carriers, an antirheumatic agent can be manufactured.

The compound of the present invention, an optically active substance thereof or a salt thereof has various physiological activity such as anti-inflammatory activity to arthritis, etc., inhibition activity of carrageenan edema, inhibition activity of tumor necrosis factor production, increasing activity of interleukin-10 production, inhibition activity of nitrogen monoxide production, induction activity of Fas antigen production, immunomodulating activity such as inhibition activity of delayed type hypersensitivity, inhibition activity of lymphocyte transformation, inhibition activity to mixed lymphocyte reaction, inhibition activity to IgE production, etc. Thus, the drug such as anti-inflammatory agent or inflammation preventer, inhibitor of tumor necrosis factor production or preventer of tumor necrosis factor production, enhancer of interleukin-10 production, immunomodulator, inhibitor of nitrogen monoxide production, inducer of Fas antigen production, immunomodulator, inhibitor of IgE production, inhibitor of delayed type hypersensitivity and antiallergic agent containing at least one compound selected from the compound of the present invention, an optically active substance thereof or a salt thereof can be made into pharmaceutical preparations by the same manner as in the case of the above anti-rheumatic agent and can be administered by the same manner as above.

Rheumatism is an autoimmune disease where hindrance takes place in perisoteal cells and cartilage cells and the antiallergic agent of the present invention is useful as a therapeutic agent to autoimmune diseases as well.

The compound of the present invention, an optically active substance thereof and a salt thereof inhibits the production of tumor necrosis factor which is believed to directly cause the inflammation in organ-specific autoimmune diseases such as chronic rheumatoid arthritis or inflammatory diseases and enhances the production of interleukin-10 which is a ThI inhibiting cytokine.

Accordingly, symptoms of inflammation such as rheumatism which is an organ-specific autoimmune disease, particularly chronic rheumatoid arthritis are improved; inflammation markers such as C-reactive protein (CRP) value, rheumatoid factor (RF) value and erythrocyte sedimentation rate (blood sedimentation) are greatly decreased; and complications such as dysbasia is significantly improved as well.

Tumor necrosis factor was found as a factor which induces hemorrhagic necrosis to tumor site and, at present, it is recognized as cytokine which broadly participates in inflammatory-based biophylaxis and immune function. Failure in a regulation of production of this tumor necrosis factor causes various inconveniences to the host, and excess or unmodulated production of tumor necrosis factor is related to many diseases including chronic rheumatoid arthritis, rheumatic myelitis, osteoarthritis, gouty arthritis, sepsis, septic shock, endotoxin shock, sepsis by gram-negative bacteria, toxic shock syndrome, cerebral malaria, chronic pneumonia, graft versus host disease, rejection reaction to allograft, influenza and other fever and muscular pain by infectious diseases, secondary cachexia to infection or malignant tumor, secondary cachexia to human acquired immunodeficiency syndrome (AIDS), AIDS, AIDS-related syndrome, keloid formation, ulcerative colitis, multiple sclerosis, autoimmune diabetes mellitus and systemic lupus erythematosus [Molecular Medicine, volume 33, pages 1010–1020 and pages 1182–1189 (1996)]. The inhibitor of tumor necrosis factor production of the present invention is useful for therapy of diseases which is mediated or worsened by tumor necrosis factor. The present invention further offers a method for controlling the production of tumor necrosis factor where at least one compound selected from the compound of the present invention, an optically active substance thereof or a salt thereof is used as an effective component.

Nitrogen monoxide (hereinafter, abbreviated as NO) is a main factor of endothelium-dependent relaxing factor (EDRF) [Nature, volume 327, pages 524–526 (1987)]. The present invention offers a drug containing at least one compound selected from the compound of the present invention, an optically active substance thereof or a salt thereof as an effective component for the therapy or prevention of the diseases requiring the inhibition of NO production. There is no particular limitation for the diseases which require the inhibition of NO production and the examples thereof are systemic hypotension caused by toxic shock or by therapy of certain cytokine, lowering in blood pressure response, autoimmune diseases, inflammation, arthritis, rheumatic arthritis, diabetes mellitus, inflammatory intestine diseases, insufficiency of blood vessel function, etiological dilation of blood vessel, damage of tissues, cardiovascular ischemia, sensitivity to pain, cerebral ischemia, diseases caused by angiogenesis, cancer, etc. The diseases include those which are mentioned in the Japanese Laid-Open Patent Publications Hei-09/504,524; 09/505,288; 08/501,069; 08/512,318; and 06/508,849.

The inhibitor of NO production containing at least one compound selected from the compound of the present invention, an optically active substance thereof or a salt thereof as an effective component is useful for the study of mechanism of NO production and of mechanism of biological activity of NO and, in addition, it may be used for screening the substances participating in the mechanism of NO production.

The compound of the present invention, an optically active substance thereof or a salt thereof has an inhibition activity of NO production in the NO-productive cells. For example, when endotoxin (lipopolysaccharide or LPS) is added to macrophage cell strain, inducible NO synthetase (NOS) is expressed and NO is secreted into a medium while, when LPS is added in the co-existance of the compound of the present invention, an optically active substance thereof or a salt thereof, production of NO is inhibited. When NO production is induced by treating with LPS, survival rate of cells decreases due to a cytopathy activity of NO but, when the compound of the present invention, an optically active substance thereof or a salt thereof is added during the treatment with LPS, production of NO decreases and disturbance to cells inhibits as well.

Angiogenesis is essential for growth of solid carcinoma and angioendothelial growth factor/vascular endothelial growth factor (VEGF) plays an important role in this step. In various cancer cells, VEGF is induced by NO. When the compound of the present invention, an optically active substance thereof or a salt thereof inhibits the NO production, VEGF production of cancer cells is inhibited as well and, as a result, angiogenesis around the cancer tissues is inhibited. When the compound of the present invention, an optically active substance thereof or a salt thereof is administered to mouse wherein solid cancer is formed by a subcutaneous transplantation of cancer cells, formation of blood vessel around the cancer tissues becomes insufficient and cancer is detached therefrom.

Nitrosoamines are a series of compounds which is synthesized by nitroso group addition to secondary amine and several hundreds of nitrosoamines have been known. Many of them damage the DNA, and have carcinogenicity to animals. It has been said that nitrosoamines are greatly related to cancer generation in human being as well and are usually produced in stomach by the reaction of nitrite with amine. Even under a physiological condition of neutral pH, NO reacts with amine to afford nitrosoamine. In addition, NO production is increased in the patients infected by oriental liver fluke and those suffering from hepatic cirrhosis which is highly related to cancer immunologically. Accordingly, when increase of the NO production is suppressed by administration of the compound of the present invention, an optically active substance thereof or a salt thereof, it is possible to prevent the generation of cancer, especially in a high-risk group. As such, the compound of the present invention, optically active substance thereof or salt thereof exhibits an anticancer action in the two steps of inhibition of carcinogenesis and also of inhibition of angiogenesis in cancer tissues.

Further, NO induces the edema which is noted characteristically in inflammatory lesions, i.e. blood vessel permeability [Maeda, et al., Japanese Journal of Cancer Research, volume 85, pages 331–334 (1994)] and also induces the biosynthesis of prostaglandins which are inflammation mediators [Salvemini, et al., Proceedings of National Academy of Sciences, U. S. A., volume 90, pages 7240–7244 (1993)]. On the other hand, it is believed that NO quickly reacts with superoxide radicals and the resulting peroxy nitrite causes inflammatory cells and tissue damages.

When activated immune cells are taken in organ and cytokine is released therefrom, production of NO is induced. Insulin-dependent diabetes mellitus is a diseases caused by a specific destruction of Langerhans β cells and the destruction is done by NO. In addition, the joint fluid of lesions of patients suffering from chronic articular rheumatism, osteoarticular rheumatism, gouty arthritis and arthritis accompanied by Behcet disease contains higher concentrations of NO as compared with the joint fluid in the normal joints of such patients or in the joints of healthy persons.

When the compound of the present invention, an optically active substance thereof or a salt thereof is administered to such patients, production of NO in the lesions is inhibited and the symptom is improved.

During cerebral ischemia and after re-perfusion, production of NO increases and, as a result, cerebral tissues are damaged. When the compound of the present invention, an optically active substance thereof or a salt thereof is administered to the patient during cerebral ischemia, damage of the cerebral tissues is reduced and prognosis is improved.

Cell surface antigen which is called as Fas antigen (APO-1 antigen or CD95) has been receiving attention as molecules for inducing the apoptosis [Cell, volume 66, pages 233–243 (1991); J. Exp. Med., volume 169, pages 1747–1756 (1989); J. Biol. Chem., volume 267, pages 10709–10715 (1992); and J. Immunology, volume 184, pages 1274–1279 (1992)].

Fas antigen is expressed in immune cells such as thymus cells, T cells, cytotoxic T cells, B cells and NK cells. Against invasion of foreign non-autoantigen, immune system induces immunoreaction whereby the non-autoantigen is excluded. However, it does not show immunoreaction but self tolerance is established. This is because lymphocytic stem cells having autoreactivity is subjected to removal of clones which is a negative selection whereby the exclusion takes place by death of cells by apoptosis. However, when those cells are not subjected to apoptosis due to some abnormality in living body such as genetic deficiency of Fas antigen, the autoreactive T cells for example are accumulated in peripheral areas. In normal living body, self tolerance is available even for B cells which are the cells in charge of immune and those autoreactive B cells are usually dead due to apoptosis but, when the autoreactive B cells are not subjected to apoptosis due to abnormality such as genetic deficiency of Fas antigen, the autoreactive B cells are accumulated in peripheral areas. In addition, in the case of articular rheumatism, the above-mentioned abnormality in autoreactive lympocytes and abnormality in turn-over of synovial cells are some of the causes of the diseases.

An inducer for production of Fas antigen in which at least one compound selected from the compound of the present invention, an optically active substance thereof or a salt thereof is an effective component is useful for induction of apoptosis of unnecessary cells for constituting the living body which are not discharged from living body due to abnormality of turnover and autoreactive lymphocytes and can be used in a method of inducing the Fas antigen production. The inducer of Fas antigen production containing at least one compound selected from the compound of the present invention, an optically active substance thereof or a salt thereof as an effective component is also useful as an agent for prevention or therapy of the diseases accompanied by abnormal production of Fas antigen. In the present invention, there is no particular limitation for the diseases accompanied by abnormal production of Fas antigen and its examples are articular rheumatism and autoimmune diseases caused by autoreactive T cells and autoreactive B cells, etc. including the diseases mentioned in the specification of WO97/0965.

The compound of the present invention, an optically active substance thereof or a salt thereof has an immunomodulating activity such as enhancer activity of interleukin-10 production, inhibition activity of delayed type hypersensitivity reaction, inhibition activity of lymphocyte transformation, inhibition activity of mixed lymphocyte reaction, inhibition activity of IgE production and inhibition activity of carrageenan edema and the immunomodulator containing at least one compound selected from the compound of the present invention, an optically active substance thereof or a salt thereof as an effective component is useful as an agent for therapy or prevention of the diseases caused by abnormality of those immune system and immune factor.

Thus, as a result of reduction of interleukin-10 production, Th1 is activated and inflammation of Th1-dominant autoimmune is induced. This inflammation participates in organ-specific autoimmune diseases such as nephritis and hepatitis as well as graft rejection and allergic contact dermatitis. The immunomodulator of the present invention enhances the interleukin-10 production and inhibits the Th1 activity whereby it is useful for the therapy and prevention of those diseases.

Lymphocyte transformation is a reaction in which mitogen is bonded to the receptor on the surface of lymphocyte to activate the lymphocyte whereby division and growth thereof are promoted. Mixed lymphocyte reaction is a reaction in which lymphocytes obtained from animals of the same species but different strain are subjected to a mixed culture whereupon activation of lymphocytes due to disagreement of main tissue-adaptable antigens is induced and division and growth of the lymphocytes are promoted. The above-mentioned immunomodulator inhibits those reactions and is particularly useful for therapy or prevention of the chronic autoimmune diseases caused by abnormal promotion of lymphocytes such as chronic nephritis, chronic colitis, diabetes mellitus of type I and chronic articular rheumatism and is also useful in inhibiting the graft rejection.

Carrageenan pododema model is a reaction in which carrageenan which is an inflammation inducer is subcutaneously injected to paws to induce inflammation cells such as macrophage and neutrophils whereby blood vessel permeability is enhanced by inflammatory factors produced from those cells inducing the edema. The inhibiting action of the above-mentioned immunomodulator to edema is useful for therapy or prevention of diseases requiring control of enhancement of blood vessel permeability such as chronic articular rheumatism.

In allergic diseases represented by asthma and atopic dermatitis, release of chemical mediators from mast cells plays an important role in allergic reaction. This reaction is induced when IgE is bonded to receptors on cell membrane to form a cross-linkage and the immunomodulator of the present invention inhibits the production of IgE and is quite useful for improvement of symptoms and/or prevention of diseases mediated or worsened by the IgE production such as allergic diseases caused by IgE including bronchial asthma, allergic rhinitis, atopic dermatitis, allergic conjunctivitis, urticaria, anaphylactic shock, etc. In addition, the immunomodulator of the present invention inhibits the delayed type hypersensitivity reaction and is useful for therapy and prevention of the diseases accompanied by the delayed type hypersensitivity such as contact hypersensitivity, allergic contact dermatitis, bacterial allergy, fungal allergy, viral allergy, drug allergy, thyroiditis and allergic encephalitis.

As a result of pathological studies for diabetes mellitus in recent years, it was reported that normal fat cells play an important role in normal systemic insulin action and that, for a smooth progress of saccharide metabolism, normal fat cells are necessary [Jikken Igaku, volume 14, pages 61–68 (1996)].

The compound of the present invention, an optically active substance thereof or a salt thereof has an ability of inducing the differentiation of precursor of fat cells such as precursor of fibroblast and induces the differentiation of said cells to fat cells. Therefore, when the compound of the present invention, an optically active substance thereof or a salt thereof is administered, normal fat cells increase whereby symptom of diabetes mellitus is improved.

The compound of the present invention, an optically active substance thereof or a salt thereof has a hypoglycemic activity and it is now possible to prepare an agent for therapy or prevention of diabetes mellitus containing at least one compound selected from the compound of the present invention, an optically active substance thereof or a salt thereof as an effective component.

Thus, when at least one compound selected from such compounds is used as an effective component and is made into a pharmaceutical preparation by combining with known pharmaceutical carriers, it is now possible to prepare an agent for therapy or prevention of diabetes mellitus. Said pharmaceutical preparation can be manufactured by the same manner as in the case of the above-mentioned anti-cancer agent and can be administered by the same manner as in the case of the above-mentioned drugs.

The compound of the present invention, an optically active substance thereof or a salt thereof has an activity of improving the hyperlipemia or activity of reducing the total cholesterol in serum, activity of reducing the triglycerides in serum and activity of reducing the free fatty acids in serum and, when at least one compound selected from the compound of the present invention, an optically active substance thereof or a salt thereof having such an activity is used as an effective component and is made into pharmaceutical preparation by combining with known pharmaceutical carriers, it is now possible to manufacture an agent for therapy or prevention of hyperlipemia. Manufacture of such a preparation can be conducted by the same manner as in the case of the above-mentioned therapeutic or preventive agent for diabetes mellitus and such a preparation can be administered by the same manner as in said therapeutic or preventive agent for diabetes mellitus. When the product containing the compound of the present invention, an optically active substance thereof or a salt thereof is taken, hyperlipemia is improved and lipid level in blood is significantly reduced.

In addition, when the compound of the present invention, an optically active substance thereof or a salt thereof having an ability of inducing the differentiation of the fat cell precursor to fat cells is used as an effective component and made into pharmaceutical preparations combining with the known pharmaceutical carriers, it is now possible to manufacture an agent for inducing the differentiation of precursor fatty cells to fatty cells. Manufacture of said agent may be conducted by the same manner as in the case of above-mentioned therapeutic or preventive agent for diabetes mellitus and the agent may be administered by the same manner as in the case of the agent for therapy or prevention of diabetes mellitus.

Further, the compound of the present invention, an optically active substance thereof or a salt thereof has an inhibition activity of the production of tumor necrosis factor and is useful for therapy or prevention of non insulin dependent diabetes mellitus caused by tumor necrosis factor [Nature, volume 389, pages 610–614 (1997)].

The compound of the present invention, an optically active substance thereof or a salt thereof has an antiviral activity and, when at least one compound selected therefrom is used as an effective component and is made into a pharmaceutical preparation by combining with known pharmaceutical carriers, it is now possible to prepare an antiviral agent. Manufacture of the antiviral agent may be conducted by the same manner as in the case of the above-mentioned anticancer agent and can be administered by the same manner as in the case of the above-mentioned drugs.

The compound of the present invention, an optically active substance thereof or a salt thereof has antiviral activity against DNA virus, RNA virus, retrovirus and viroid.

Accordingly, it may be used as antiviral agent for human being, antiviral agent for non-human animals such as that effective to viral diseases (e.g. for domestic animals, domestic fowls and cultured animals such as fish and shrimp), antiviral agent for plants such as that for viral diseases of agricultural and horticultural products (e.g. flowers and vegetables) and antiviral agent for useful animate things.

Viral diseases of birds such as Marek disease can be prevented and/or cured by the compound used in the present invention by the method known in veterinary or breeding such as that the antiviral agent of the present invention is injected to birds or added to feed or drinking water. Further, when the compound used in the present invention is directly added to pool, water tank, holding tank, or water, seawater, etc. in a breeding area or is mixed with the feed, the viral diseases can be similarly prevented and/or cured.

The non-human animals to which the antiviral agent of the present invention is administered are able to maintain their health whereby the improvement in survival rate, growing rate, spawning rate, etc. is significant.

The compound of the present invention, an optically active substance thereof or a salt thereof used in the present invention inhibits the synthesis of those viral proteins and inhibits the synthesis of virus genome as well and, accordingly, it exhibits a powerful antiviral action. In addition, it selectively kills the cells infected by those viruses.

For example, even in the patients suffering from human immunodeficiency virus (hereinafter, abbreviated as HIV), all of the CD4-positive cells are not infected by HIV but only a part of them are infected by it. The antiviral agent of the present invention inhibits the production of HIV in those infected cells, at the same time, selectively kills the infected cells, and induces the resisting ability to virus to the uninfected cells whereby it is possible to remove the HIV from the cells.

The compound of the present invention, an optically active substance thereof or a salt thereof has an ability of improving the hepatic function and an induction activity of the heat shock protein. An agent for improving the hepatic function and an agent for inducing the heat shock protein containing at least one compound selected from the compound of the present invention, an optically active substance thereof or a salt thereof can be made into a pharmaceutical preparation by the same manner as in the case of the above-mentioned antiviral agent and can be administered by the same manner as in the case of the antiviral agent.

When the compound of the present invention, an optically active substance thereof or a salt thereof is taken, disorder in hepatic function is improved and GOT and GPT values become normal.

Moreover, the compound of the present invention, an optically active substance thereof or a salt thereof has an induction activity of heat shock protein 70 kDa (HSP70), etc. and has an antiviral activity to RNA virus and DNA virus such as hepatitis virus, AIDS virus, influenza virus, vesicular stomatitis virus and herpesvirus. Heat shock protein participates in cancer immunity and those compounds are effective to cancer immunity as well. Further, the compounds has biodefense activity such as anti-inflammation activity. Since the compound of the present invention, an optically active substance thereof or a salt thereof has a high inducing ability to heat shock protein, it has antiviral activity to DNA virus, RNA virus, retrovirus and viroid. Examples of such virus and viroid are those which were mentioned hereinabove.

In addition, the compound of the present invention, an optically active substance thereof or a salt thereof has an inhibition activity of the growth of cancer cells which are transformed by cancer gene and has an activity of preventing the carcinogenesis due to cancer gene.

The compound of the present invention, an optically active substance thereof or a salt thereof has an activity of growth inhibition of cancer cells which are cancerated by cancer gene E7 of an HPV16 type. Thus, an inhibiting agent to the growth of cancer cells which are cancerated by virus can be offered by the use of at least one compound selected from the compound of the present invention, an optically active substance thereof or a salt thereof as an effective component whereby canceration by cancer gene can be prevented.

Incidentally, the compound of the present invention, an optically active substance thereof or a salt thereof has an inhibition activity to carcinogenesis in two steps as an initiator and a promoter and it is now possible to offer an inhibiting agent to chemical canceration containing at least one compound selected from the above compound as an effective component.

The compound of the present invention, an optically active substance thereof or a salt thereof has an inhibition activity of IgE production and of a delayed type hypersensitivity and, when at least one compound selected from the above compound is used as an effective component and made into a pharmaceutical preparation combining with known pharmaceutical carriers, an antiallergic agent can be manufactured. Manufacture of said preparation can be conducted by the same manner as in the case of the abovementioned anticancer agent. Incidentally, the antiallergic agent of the present invention can be administered by an appropriate route depending upon the dosage form.

An agent for inhibiting the IgE production and the delayed type hypersensitivity containing at least one compound selected from the compound of the present invention, an optically active substance thereof or a salt thereof as an effective component can be made into a pharmaceutical preparation by the same manner as in the case of the above-mentioned antiallergic agent and can be administered by the same manner as in the case of the antiallergic agent.

The antiallergic agent of the present invention inhibits the IgE production and is very useful for improvement and/or therapy of the diseases which is mediated or worsened by the IgE production such as allergic diseases caused by IgE including bronchial asthma, allergic rhitinis, atopic dermatitis, allergic conjunctivitis, urticaria and anaphylactic shock. It also inhibits the delayed type hypersensitivity and is useful for therapy and prevention of the diseases accompanied by a delayed type hypersensitivity such as contact sensitivity, allergic contact dermatitis, bacterial allergy, fungal allergy, viral allergy, drug allergy, thyroiditis and allergic encephalitis.

No dead case was observed in rats by a single oral administration of the compound of the present invention, an optically active substance thereof or a salt thereof even when the dose which is effective to achieve those physiological activities is administered.

As such, the compound of the present invention, an optically active substance thereof or a salt thereof is a very useful compound in an area of pharmaceuticals because of its various physiological functions.

EXAMPLES

The present invention will be further illustrated by way of the following examples although the present invention is never limited to those examples. Incidentally, "%" used in the examples stands for "% by weight".

Example 1

(1) D-Glucuronic acid (G 5269; manufactured by Sigma) (10 g) was dissolved in 1 liter of water, heated at 121° C. for four hours and concentrated in vacuo until about 10 ml. This was mixed with 40 ml of an upper layer of a 3:2:2 mixture of butyl acetate, acetic acid and water and centrifuged and the resulting supernatant liquid was concentrated in vacuo until about 10 ml.

The above extract was applied to silica gel (BW-300SP; 2×28 cm; manufactured by Fuji Silycia) for a column chromatography and separated using an upper layer of a 3:2:2 mixture of butyl acetate, acetic acid and water as an eluate at the flow rate of about 5 ml/minute under a pressure of 0.2 kg/cm$^2$ using a compressor. Fractionation was conducted to make a volume of one fraction 10 ml and a part of each fraction was analyzed by a thin layer chromatography whereupon (±)-cyclopentenone of a high purity was contained in 61st to 80th fractions. Those fractions were collected, concentrated in vacuo, extracted with 40 ml of chloroform and the extract was concentrated in vacuo to afford 100 mg of (±)-cyclopentenone.

The fraction was separated by means of a normal phase HPLC using a Palpack type S column and, when a detection was conducted by an ultraviolet absorption of 215 nm, the purity was found to be 98%.

(2) Reaction of Cyclopentenone with Imidazole 100 mM cyclopentenone and 500 mM aqueous solution of imidazole (pH 7.4) were left alone at 37° C. for one hour and the reaction solution (200 μl) was separated by means of a reverse phase HPLC under the following conditions.

Column: TSK gel ODS-80Ts, 20 mm×250 mm (manufactured by Tosoh)
Guard column: TSK guard column ODS-80Ts, 20 mm×50 mm (manufactured by Tosoh)
Mobile phase: 0.1% aqueous solution of trifluoroacetic acid
Flow rate: 9 ml/minute
Detection: absorbance at 215 nm The peak of 14.75 minutes was fractionated and evaporated to dryness in vacuo to obtain imidazolylcyclopentenone.

The result is show n in FIG. 1. Thus, FIG. 1 shows an elution pattern of reverse phase HPLC of the imidazolylcyclopentenone by showing the relation between eluting time and absorbance at 215 nm in which abscissa indicates eluting time (minutes) while ordinate indicates absorbance at 215 nm.

Example 2

A fast atom bombardment mass spectrometry (FAB-MS) of the imidazolylcyclopentenone isolated in Example 1 was conducted using a mass spectrometer DX302 (manufactured by Nippon Denshi). Further, it was dissolved in heavy water and its structures was analyzed by means of nuclear magnetic resonance (NMR) JNM-A500 (manufactured by Nippon Denshi) was used as a nuclear magnetic resonance device. Ultraviolet (UV) absorption spectrum was measured using a UV-2500 spectrophotomer (manufactured by Shimadzu). Infrared absorption spectrum (IR) was measured by a diffuse reflectance method. The results are as given below.

FAB-MS: m/z 165 [M+H]$^+$
Glycerol was used as a matrix.
$^1$H-NMR: δ2.45 (1H, d, J=19.5, 5-H), 3.05 (1H, dd, J=6.5, 19.5 Hz, 5-H), 5.56 (1H, m, 4-H), 6.44 (1H, m, 3-H), 7.30 (1H, d, J=1.0, imidazole 4-H or 5-H), 7.39 (1H, d, J=1.0 Hz, imidazole 4-H or 5-H), 8.65 (1H, s, imidazole 2-H)

In the above, chemical shift values of HOD was defined as 4.65 ppm.

$^{13}$C-NMR: δ41.6 (5-C), 55.3 (4-C), 120.8 (imidazole 4-C or 5-C), 121.1 (imidazole 4-C or 5-C), 125.7 (3-C), 134.8 (imidazole 2-C), 157.2 (2-C), 202.9 (1-C)

In the above, chemical shift values of dioxane was defined as 67.4 ppm.

UV: $\lambda_{max}$ 208, 245 nm (water)
IR: $\nu^{KBr}_{max}$ cm$^{-1}$ 3100, 2846, 1722, 1633, 1573, 1299, 1085

Figure 2:
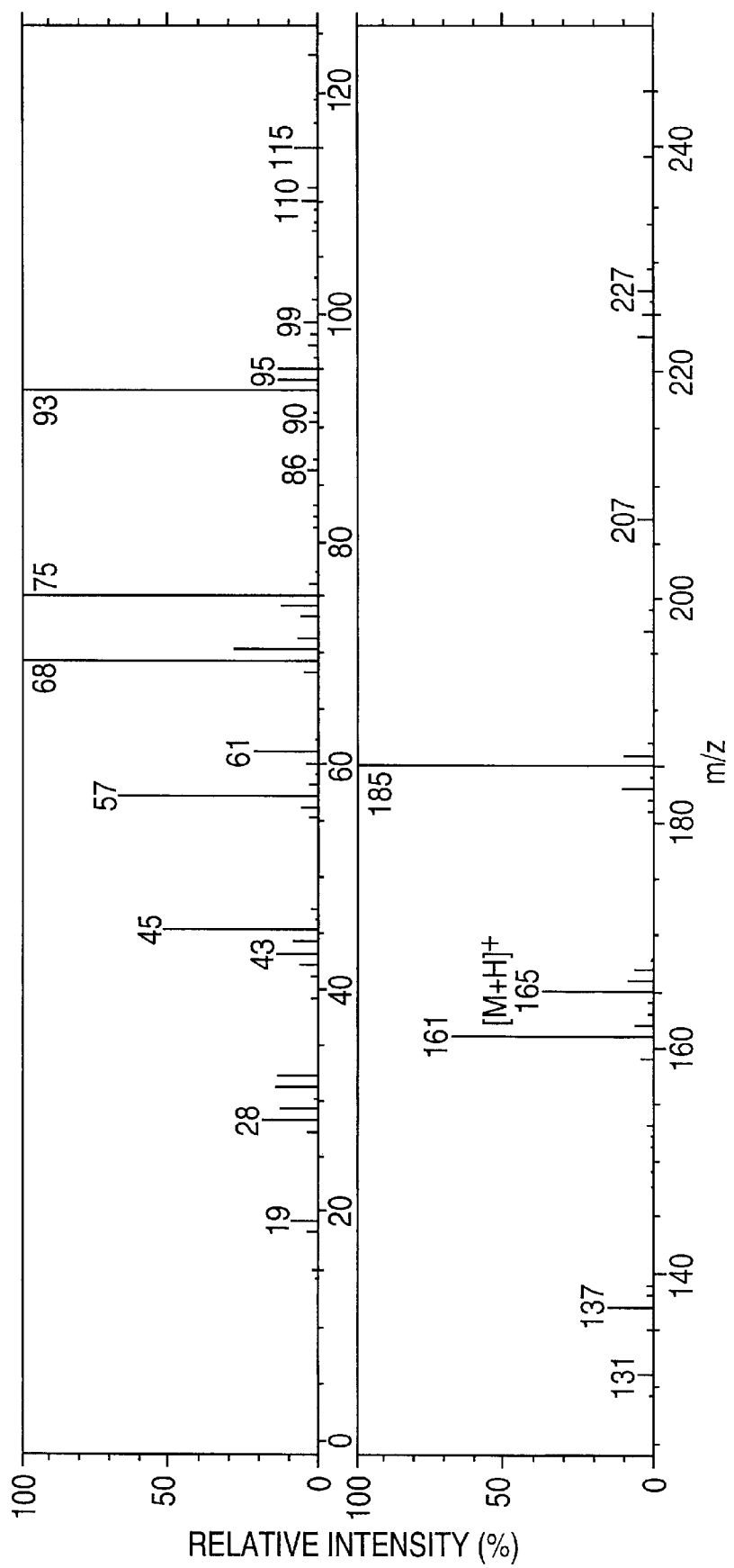
FIG. 2 shows a mass spectrum of imidazolylcyclopentenone.
Figure 3:
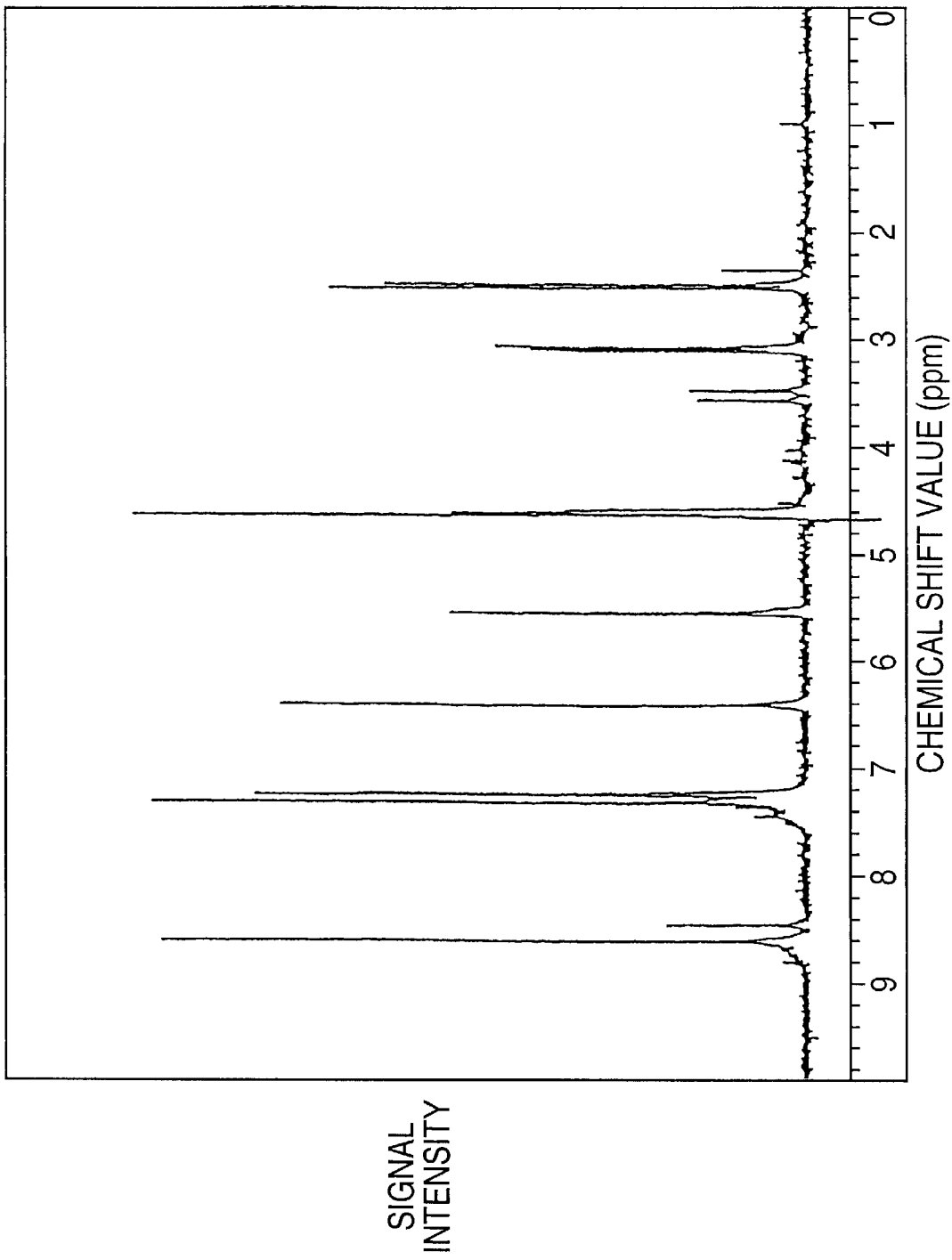
FIG. 3 shows a $^1$H-NMR spectrum of imidazolylcyclopentenone.
Figure 4:
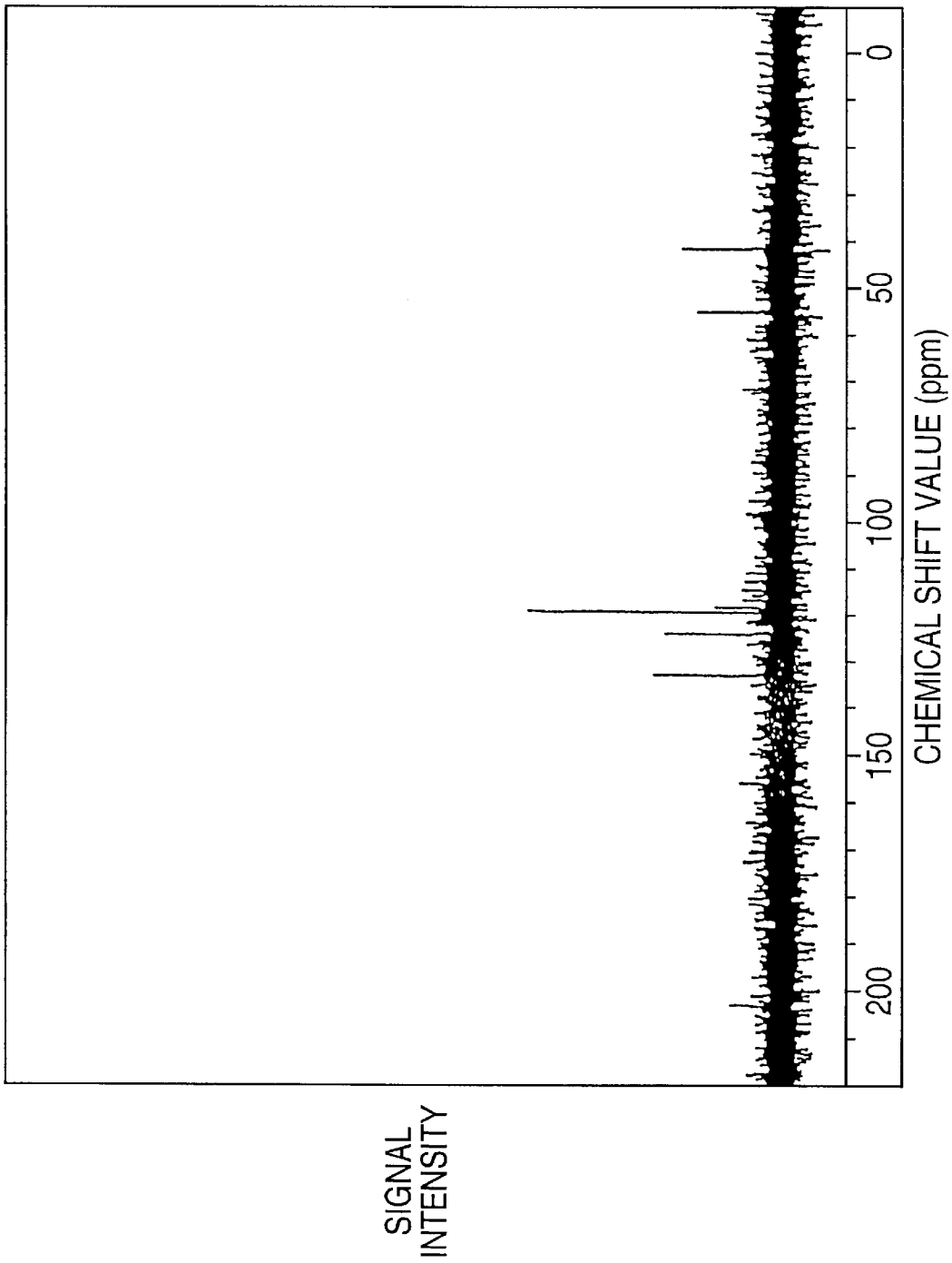
FIG. 4 shows a $^{13}$C-NMR spectrum of imidazolylcyclopentenone.
Figure 5:
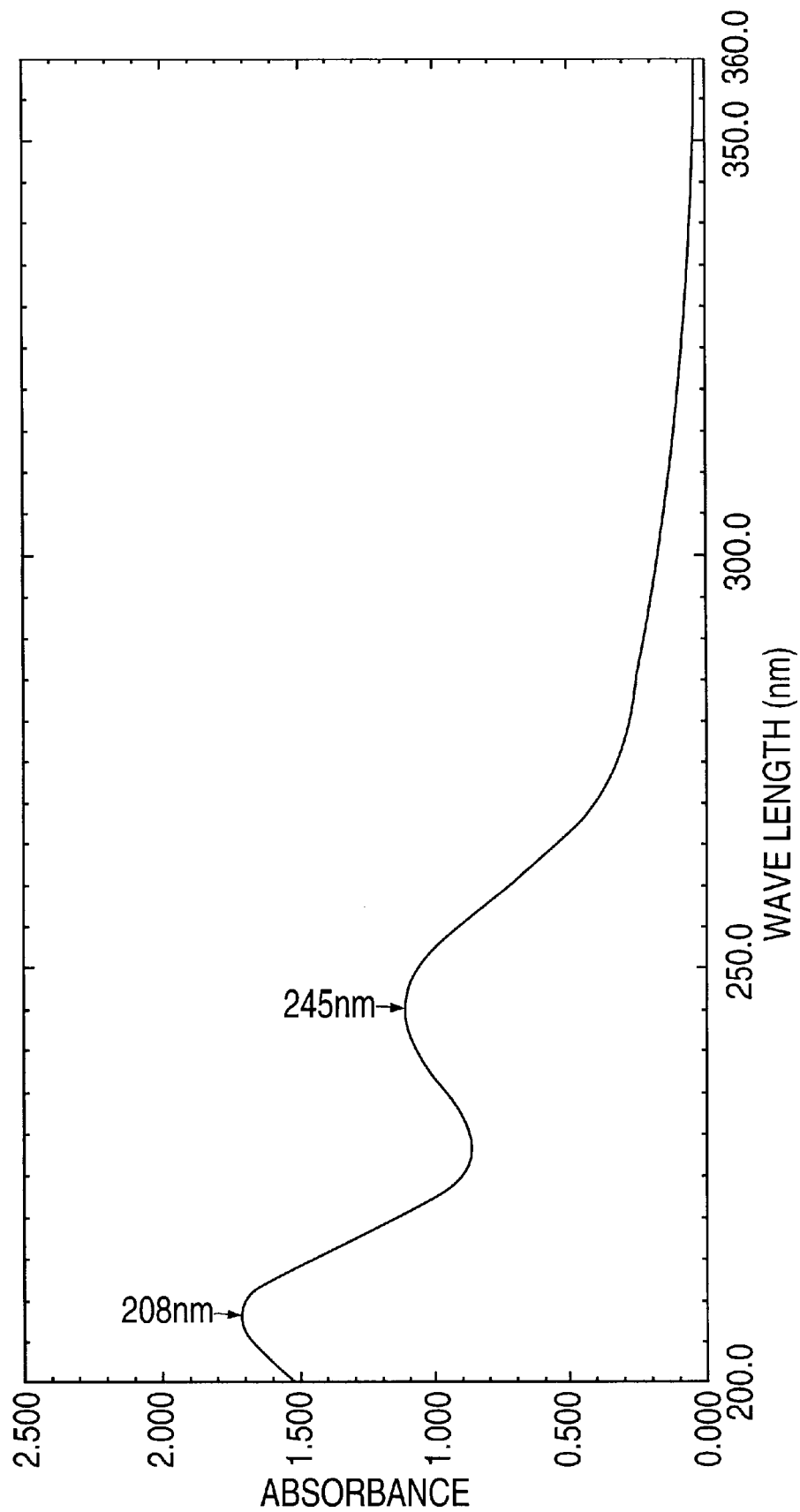
FIG. 5 shows a UV absorption spectrum of imidazolylcyclopentenone.
Figure 6:
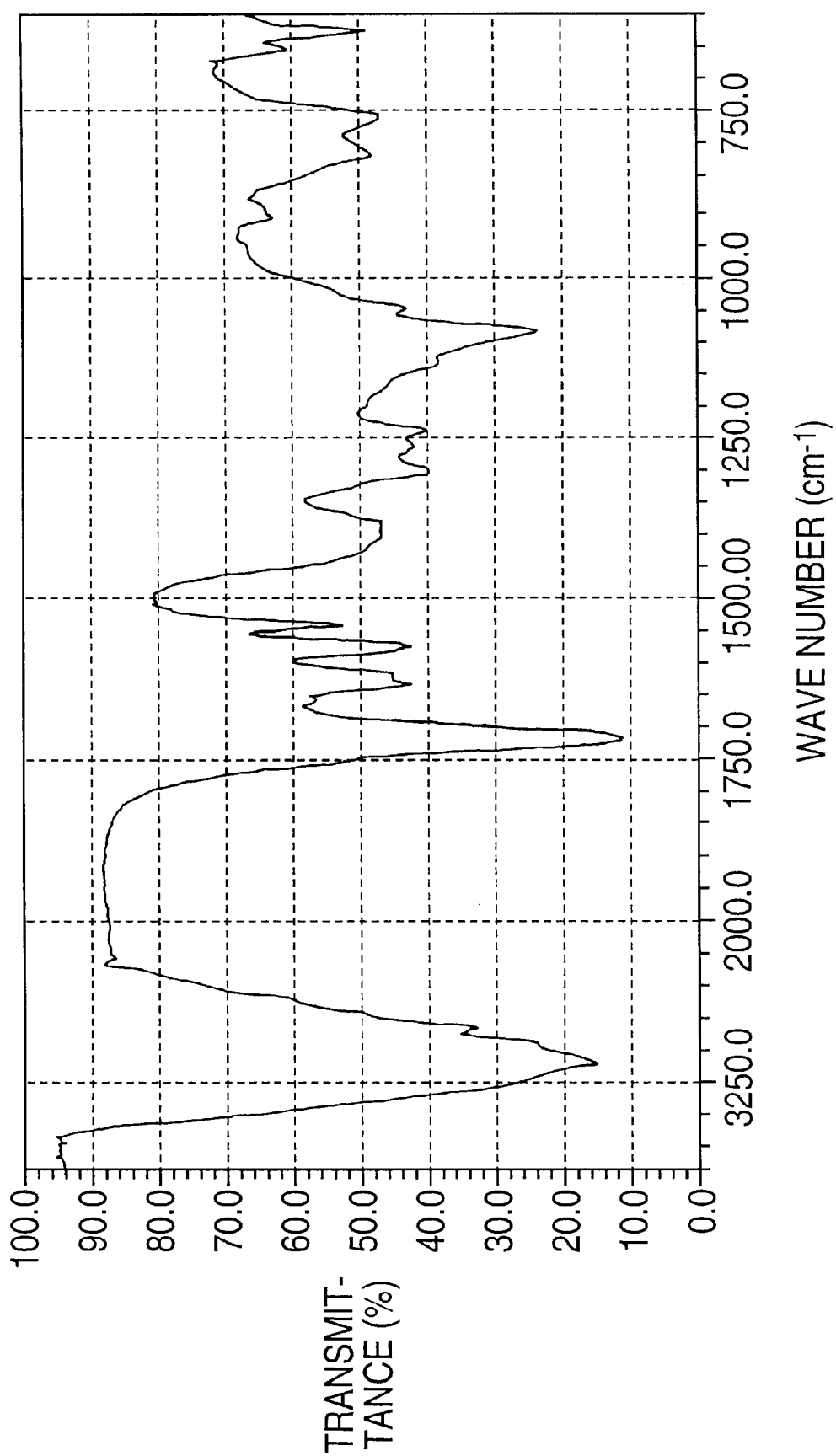
FIG. 6 shows an IR absorption spectrum of imidazolylcyclopentenone.

The results are shown in FIG. 2 to FIG. 6. Thus, FIG. 2 shows mass spectrum of imidazolylcyclopentenone in which abscissa indicates m/z values while ordinate indicates relative intensity (%). FIG. 3 shows $^1$H-NMR spectrum of imidazolylcyclopentenone in which abscissa indicates chemical shift value (ppm) while ordinate indicates the signal intensity. FIG. 4 shows $^{13}$C-NMR spectrum of imidazolylcyclopentenone in which abscissa indicates chemical shift value (ppm) while ordinate indicates the signal intensity. FIG. 5 shows UV absorption spectrum of imidazolylcyclopentenone in which abscissa indicates wave length (nm) while ordinate indicates absorbance. FIG. 6 shows IR absorption spectrum of imidazolylcyclopentenone in which abscissa indicates wave number (cm$^{-1}$) while ordinate indicates transmittance (%).

Incidentally, the numbers of assignment of the signals of $^1$H-NMR and $^{13}$C-NMR are as shown in the following formula [XIV].

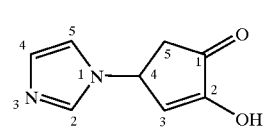

[XIV]

Example 3

To each of the wells of a 96-well microtiter plate was added 1000, 500, 250, 125, 62.5 or 31.3 μg/ml aqueous solution of imidazolylcyclopentenone obtained in Example 1-(2) or 10 μl of water as a control. HL-60 (ATCC CCL-240) was suspended in an RPMI 1640 medium containing 10% of fetal calf serum to make the concentration 5×10$^4$ cells/ml and each 90 μl thereof was placed in each well of the above-mentioned microtiter plate and incubated at 37° C. for 48 hours in the presence of 5% carbon dioxide. Incubation was conducted for four hours more after addition of 10 μl of a solution (5 mg/ml) of 3-(4,5-dimethylthiazol-2-yl)-2,5-diphenyltetrzolium bromide (MTT; manufactured by Sigma) in a phosphate-buffered saline solution and the state of growth of the cells was observed under a microscope. Further, 100 μl of 2-propanol containing 0.04N hydrochloric acid was added followed by stirring and an absorbance at 590 nm was measured.

AS a result, no growth of cells was detected in the section where 62.5 μg/ml of imidazolylcyclopentenone was added (final concentration: 6.25 μg/ml). Accordingly, it was clarified that imidazolylcyclopentenone completely inhibited the growth of HL-60 cells at the concentration of 6.25 μg/ml.

Example 4

A 0.25M sodium phosphate buffer (pH 7.0) (0.5 ml), 10 ml of a 10 mg/ml aqueous solution of N-acetylgalactosamine (manufactured by Wako Pure Chemicals; 013-12821), 0.1 ml of a 50 mg/ml aqueous solution of galactose oxidase [prepared by a method of Tressel, et al: *Methods in Enzymology,* volume 89, pages 163–171 (1982)] and 0.5 ml of a 2.35 units/ml aqueous solution of catalase (manufactured by Boehringer-Mannheim; 106 810) were mixed and water was added thereto to make 25 ml. The mixed solution was kept at 37° C. and made to react for 16 hours together with introduction of air thereinto by means of a peristaltic pump.

The above reaction product was applied to a column of 20 ml of Amberlite IRA-900 (manufactured by Organo) which was washed with 2M NaCl and equilibrated with water to give a non-adsorbed fraction.

Example 5

The non-adsorbed fraction of Example 4 was adjusted to pH 3 with HCl and heated at 121° C. for 1 hour. The resulting heat-treated solution was diluted with aseptic water to an extent of 2-, 4-, 8-, 16-, 32- or 64-fold and its activity of growth inhibition of HL-60 cells was measured by the same way as in Example 3.

The result was that, with regard to the growth of the cells, there was no difference between the sample-added section before heating and the water-added section used as a control while, in the section to which a 2-fold diluted solution of the heated solution for 1 hour was added, growth of the cells was completely inhibited and, in the section to which an 8-fold diluted solution was added, growth of the cells was inhibited to an extent of about one half. As a result of observation under a microscope, production of apoptotic body was confirmed.

Incidentally, there was no difference in terms of growth of the cells between the water-added control section and the section to which 4 mg/ml of N-acetylgalactosamine was added or the section to which N-acetylgalactosamine of the same concentration heated at pH 3 for 1 hour was added.

From the above results, it is apparent that, when the non-adsorbed fraction of the galactose oxidase-treated N-acetylgalactosamine with Amberlite IRA-900 column was heated, a substance which inhibited the growth of cancer cells was produced.

Example 6

The non-adsorbed fraction of Example 4 was freeze-dried, dissolved in 25 ml of water, adjusted to pH 3 with HCl and heated at 121° C. for 4 hours. The resulting heat-treated solution (40 μl) was separated by means of a reverse phase HPLC as shown below.

Column: TSK gel ODS-80Ts, 4.6 mm×250 mm (manufactured by Tosoh)

Flow rate: 1 ml/minute

Solvent A: 0.1% aqueous solution of trifluoroacetic acid (TFA; manufactured by Merck)

Solvent B: a 0.1% aqueous solution of TFA and a 50% aqueous solution of acetonitrile Gradient: 0 minute→15 minutes solvent A
15 minutes→45 minutes solvent A→solvent B
45 minutes→60 minutes solvent B Detection: absorbance at 210 nm Main peaks and the fractions between them were collected and evaporated to dryness in vacuo, each of the fractions was diluted to an extent of 3- or 9-fold with water and their activity of growth inhibition of HL-60 cells was measured by the same way as in Example 3 except that 5 μl of the sample were added to each well and the incubation was conducted for 18 hours. The result was that, in the section to which an aqueous solution of a retention time of 17.1 minutes was added and in the section to which its 3-fold diluted solution was added, activity of growth inhibition of cancer cells was noted. Production of apoptotic body was confirmed as well.

Figure 7:
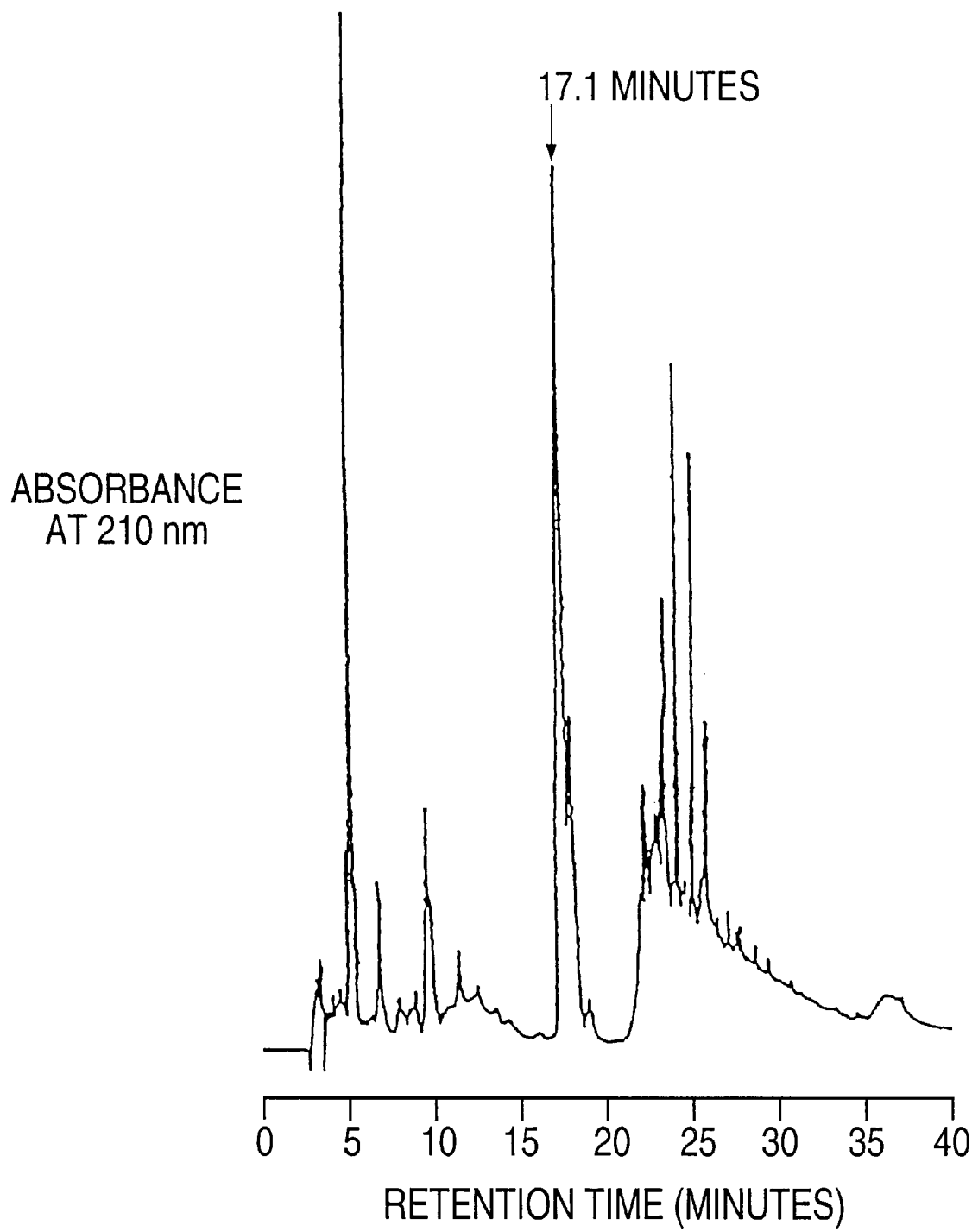
FIG. 7 shows a relation between retention time of reverse phase HPLC and absorbance at 210 nm.

Its chromatogram is shown in FIG. 7. FIG. 7 shows a relation between retention time and absorbance at 210 nm in which abscissa indicates retention time (minutes) while ordinate indicates absorbance at 210 nm.

The same reverse phase HPLC was repeated and the peak having a retention time of 17.1 minutes was fractionated and freeze-dried to isolate 5 mg of substance inhibiting the cancer cell growth.

Example 7

A substance inhibiting the cancer cell growth isolated in Example 6 from a peak of a retention time of 17.1 minutes was subjected to mass spectrometric analysis, structure analysis by means of a nuclear magnetic resonance (NMR) and infrared (IR) absorption spectrum measurement. Measurements of the mass spectrometric analysis, the NMR spectrum and the IR spectrum were carried out by a DX 302 mass spectrometer (manufactured by Nippon Denshi), a JNM-A500 (manufactured by Nippon Denshi) and an FTIR-8000 (manufactured by Shimadzu), respectively. The results are as follows.

FAB-MS: m/z 184 [M+H]$^+$, 206 [M+Na]$^+$ n-nitrobenzyl alcohol was used as a matrix.

$^1$H-NMR: 2.04 (3H, s, 9-H), 6.22 (1H, d, J=9.0 Hz, 5-H), 6.60 (1H, d, J=9.0 Hz, 6-H), 8.21 (1H, br-s, 3-OH), 8.71 (1H, br-s, 4-OH), 9.11 (1H, br-s, 2-OH), 9.48 (1H, br-s, 7-H)

The sample was dissolved in heavy dimethyl sulfoxide and the chemical shift of the residual dimethyl sulfoxide was expressed as 2.49 ppm.

$^{13}$C-NMR: δ23.0 (9-C), 106.3 (5-C), 112.7 (6-C), 119.0 (1-C), 134.3 (3-C), 138.5 (2-C), 143.3 (4-C), 169.1 (8-C)

The sample was dissolved in heavy dimethyl sulfoxide and the chemical shift of the residual dimethyl sulfoxide was expressed as 39.5 ppm.

IR: $\nu^{KBr}_{max}$ cm$^{-1}$ 3423, 1641, 1500, 1205, 1024

From the above results, it has now been clarified that the substance inhibiting the cancer cell growth is N-(2,3,4-trihydroxyphenyl)acetamide having a structure represented by the formula [II].

Figure 8:
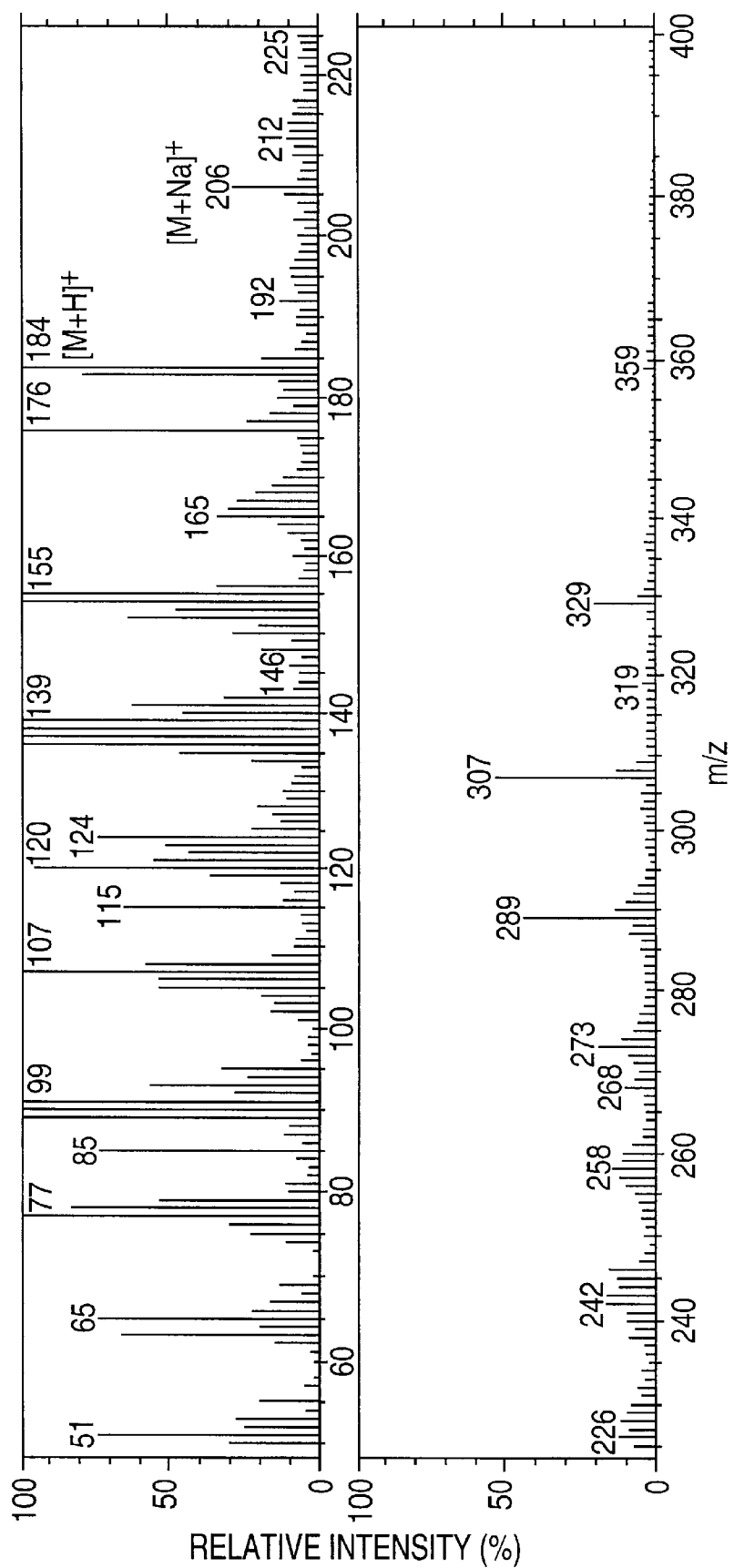
FIG. 8 shows a mass spectrum of trihydroxyphenylacetamide.
Figure 9:
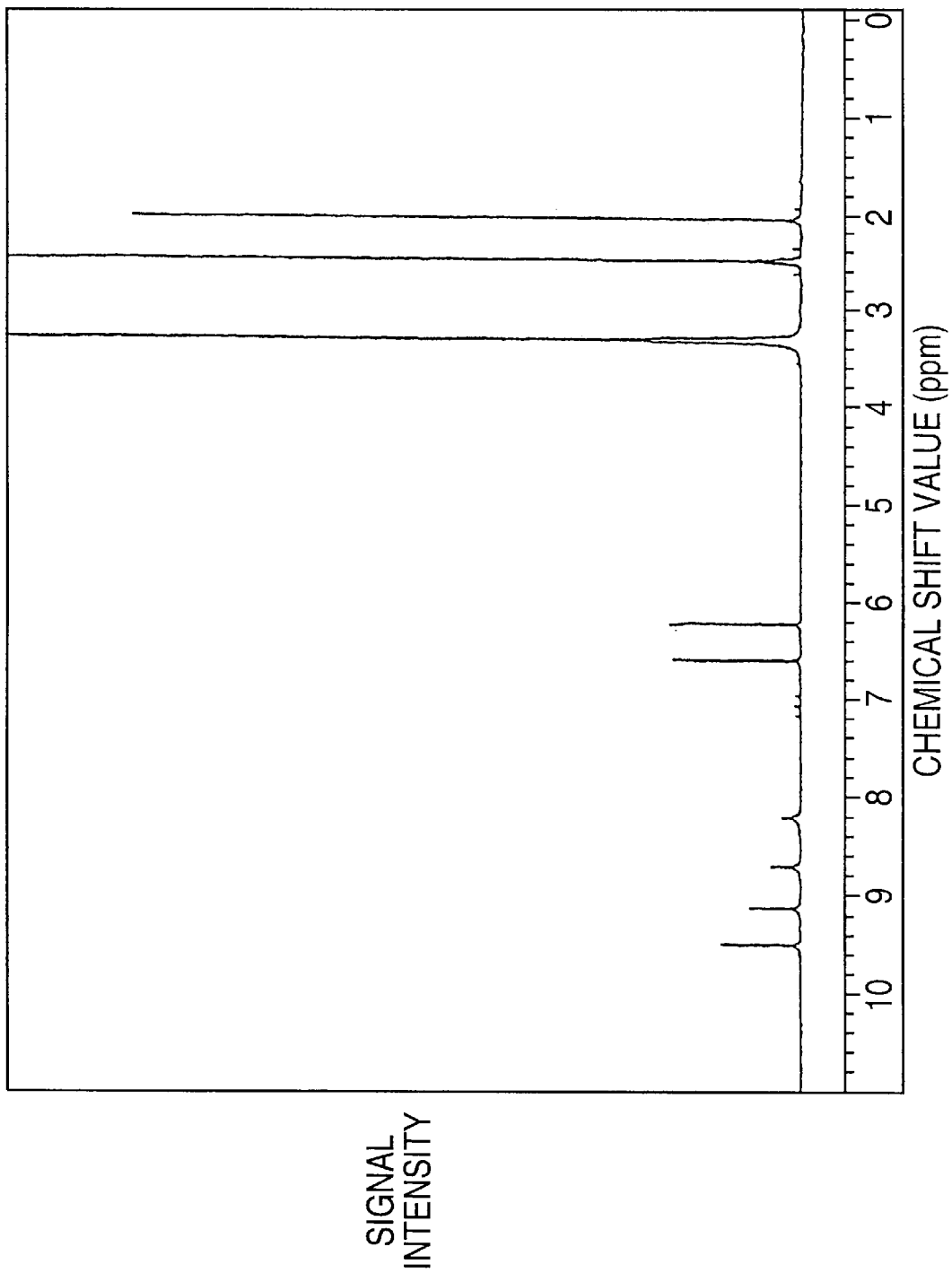
FIG. 9 shows a $^1$H-NMR spectrum of trihydroxyphenylacetamide.
Figure 10:
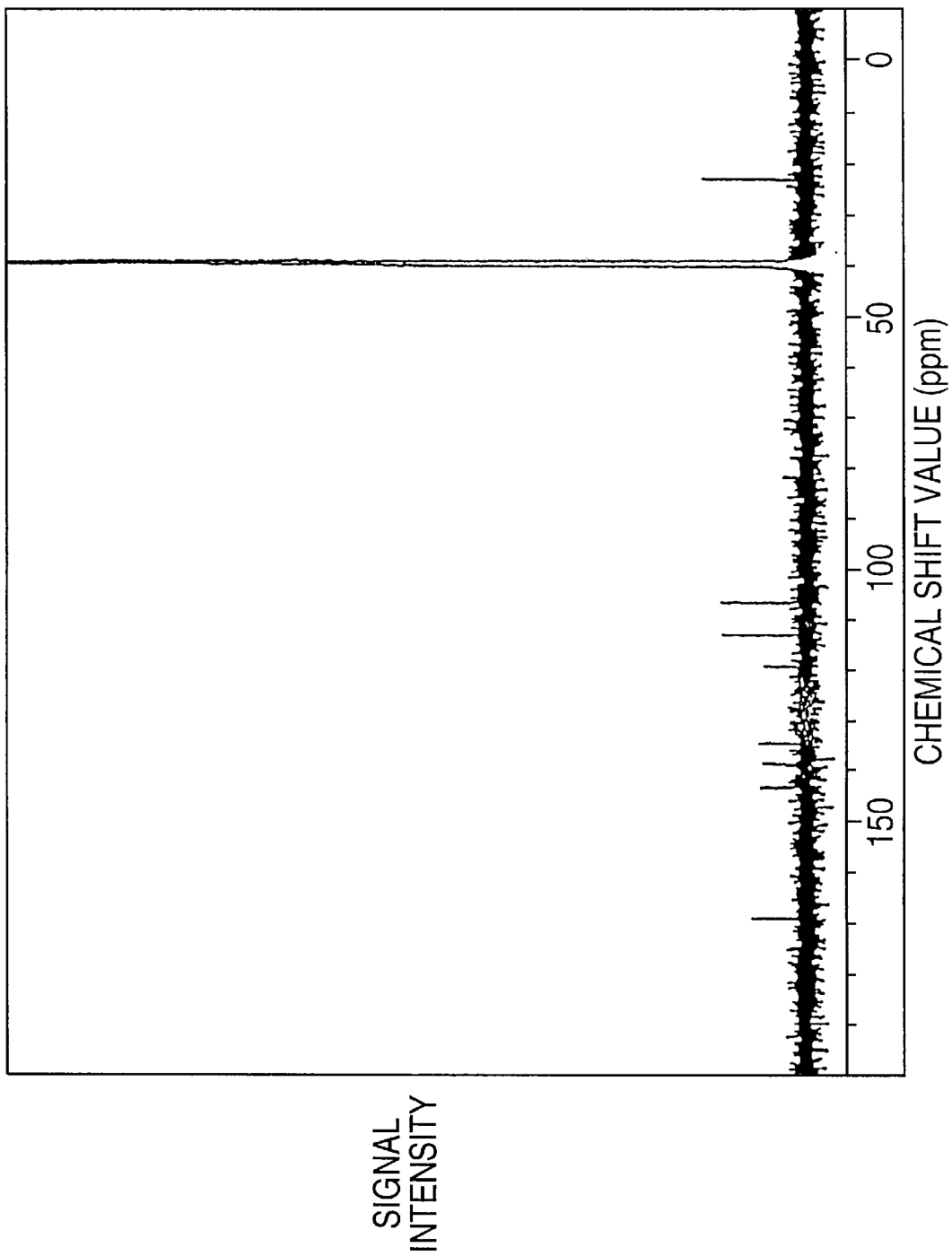
FIG. 10 shows a $^{13}$C-NMR spectrum of trihydroxyphenylacetamide.
Figure 11:
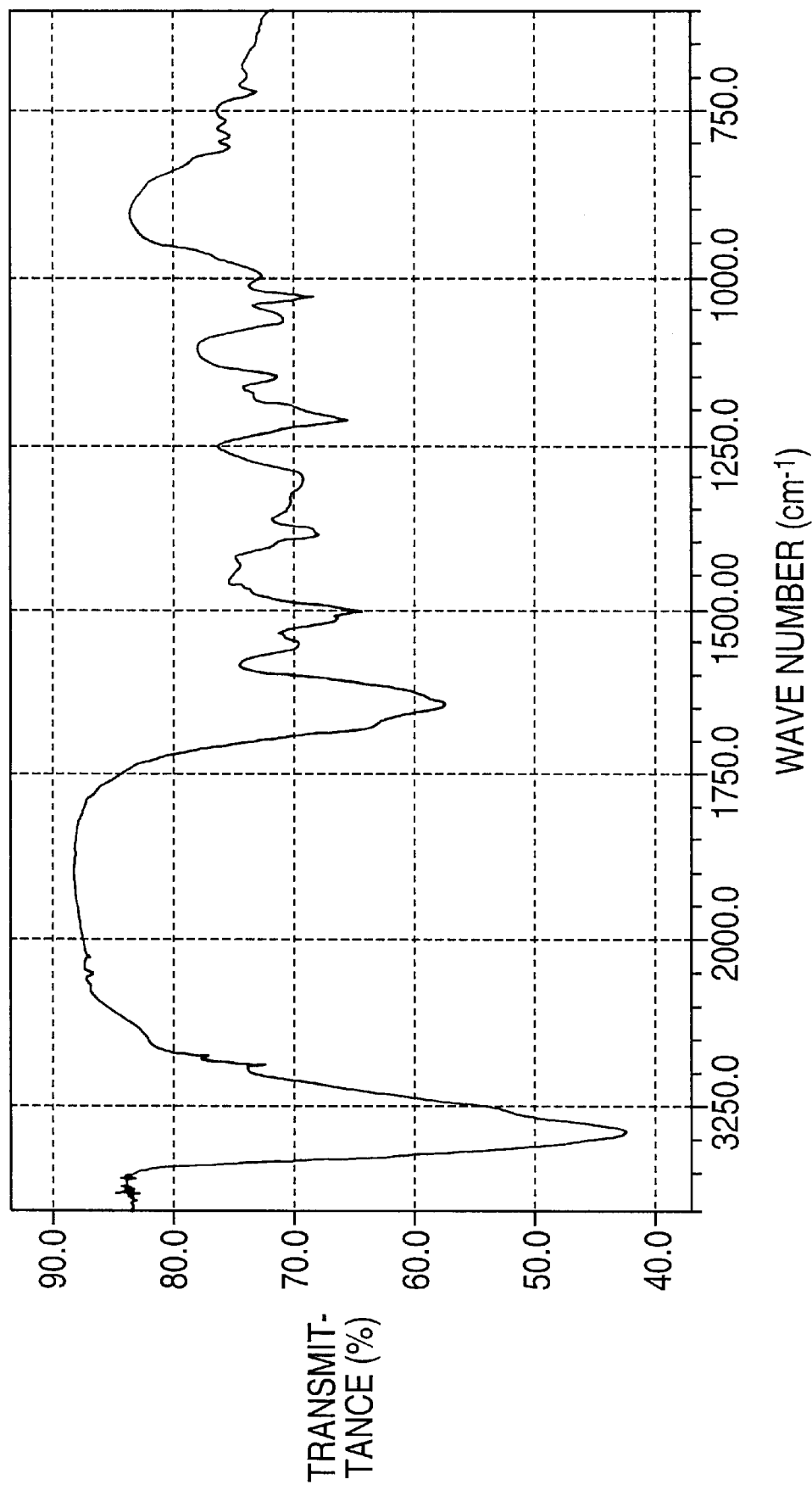
FIG. 11 shows a IR absorption spectrum of imidazolylcyclopentenone.

FIG. 8 shows its mass spectrum in which abscissa indicates m/z values while ordinate indicates relative intensity (%). FIG. 9 shows its $^1$H-NMR spectrum in which abscissa indicates chemical shift value (ppm) while ordinate indicates the signal intensity. FIG. 10 shows its $^{13}$C-NMR in which abscissa indicates chemical shift value (ppm) while ordinate indicates the signal intensity. FIG. 11 shows its IR absorption spectrum in which abscissa indicates wave number (cm$^{-1}$) while ordinate indicates transmittance (%).

Incidentally, the numbers of assignment of the signals of $^1$H-NMR and $^{13}$C-NMR are as shown in the following formula [XV].

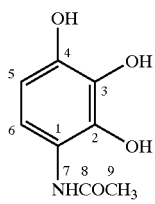

[XV]

Example 8

(1) An aqueous solution of 50 mM D-glucuronic acid and 500 mM glycine (both manufactured by Nacalai Tesque) was adjusted to pH 3 with 1N HCl and heated at 121° C. for 30 minutes.

(2) To 3 ml of the heat-treated solution obtained in Example 8-(1) were added 5 ml of 1-butanol, 3 ml of ethanol and 0.05 ml of acetic acid followed by mixing and the silica gel column chromatography of the resulting mixture was carried out as follows.

Filler: silica gel BW-300SP for column chromatography (manufactured by Fuji Silycia)

Column size: 2.0 cm×45 cm

Mobile phase: 1-butanol, ethanol, acetic acid and water in a ratio of 5:3:3:0.05

An elution was carried out by applying an air pressure of 0.4 kgf/cm$^2$ using a pump. The first 100 ml were discarded and then fractionation was carried out for each 7.5 ml. The 25th to the 28th fractions were collected and concentrated and evaporated to dryness in vacuo followed by dissolving in 200 μl of water.

(3) The partially purified specimen obtained in Example 8-(2) was further purified by the following reverse phase HPLC.

Column: CAPCELL PAK C$_{18}$ SG300 Å 5 μm, 6×250 mm (manufactured by Shiseido)

Mobile phase: 0.1% aqueous solution of trifluoroacetic acid

Flow rate: 1 ml/minute

Detection: absorbance at 215 nm

A sample (30 μl) was charged and the main peak at the retention time of 6.9 minutes was collected. This operation was carried out for four times and the collected solution was evaporated to dryness in vacuo to give B-UG.

Figure 12:
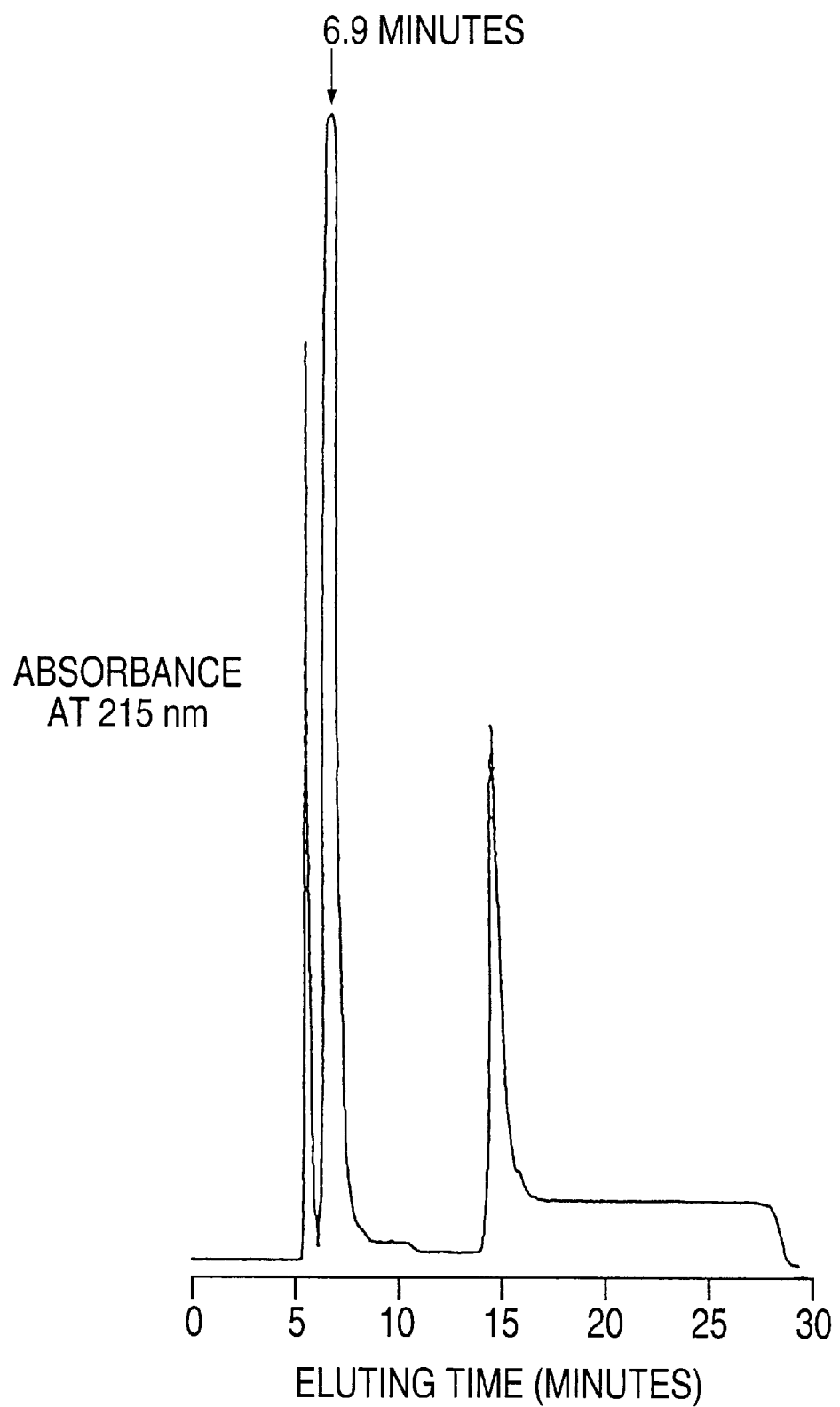
FIG. 12 shows a relation between eluting time of reverse phase HPLC of B-UG and absorbance at 215 nm.

The result is shown in FIG. 12. Thus, FIG. 12 shows a relation between eluting time of reverse phase HPLC of B-UG and absorbance at 215 nm in which abscissa indicates eluting time (minutes) while ordinate indicates absorbance at 215 nm.

Example 9

A fast atom bombardment mass spectrometry (FAB-MS) of B-UG isolated in Example 8 was conducted using a mass spectrometer DX302 (manufactured by Nippon Denshi). Further, it was dissolved in heavy water and its structures was analyzed by means of nuclear magnetic resonance (NMR). JNM-A500 (manufactured by Nippon Denshi) was used as a nuclear magnetic resonance device. Ultraviolet (UV) absorption spectrum was measured by a UV-2500 spectrophotometer (manufactured by Shimadzu); and infrared absorption spectrum (IR) was measured by an FTIR-8000 infrared spectrophotometer (manufactured by Shimadzu). The results are as given below.

FAB-MS: m/z 154 [M+H]$^+$, 176 [M+Na]$^+$, MW153

Glycerol was used as a matrix.

$^1$H-NMR: δ5.06 (2H, s, 7-H), 7.74 (1H, dd, J=6.0, 9.0 Hz, 5-H), 7.86 (1H, ddd, J=1.0, 2.5, 9.0 Hz, 4-H), 8.14 (1H, dd, J=1.0, 6.0 Hz, 6-H), 8.20 (1H, m, 2-H)

In the above, chemical shift values of HOD was defined as 4.65 ppm.

$^{13}$C-NMR: δ62.8 (7-C), 129.2 (5-C), 133.4 (4-C), 134.6 (2-C), 137.9 (6-C), 157.3 (3-C), 170.6 (8-C)

In the above, chemical shift values of dioxane was defined as 67.4 ppm.

UV: $\lambda_{max}$ 290 nm (water)

IR: $\nu^{KBr}_{max}$ cm$^{-1}$ 3100, 1678, 1499, 1325, 1198, 721

From the above, it has now been clarified that B-UG is a 1-carboxymethyl-3-hydroxypyridinium inner salt represented by the formula [XII].

Figure 13:
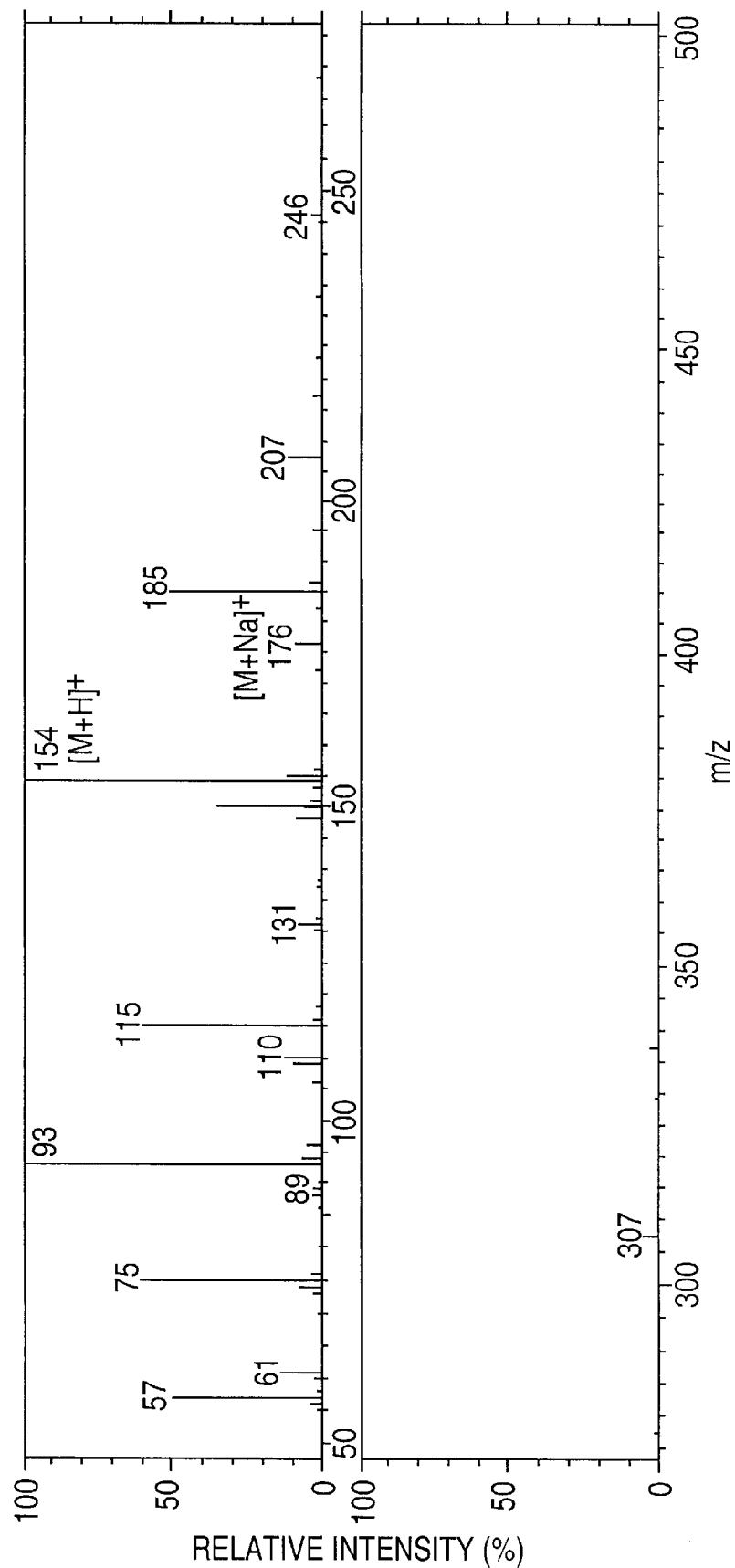
FIG. 13 shows a mass spectrum of B-UG.
Figure 14:
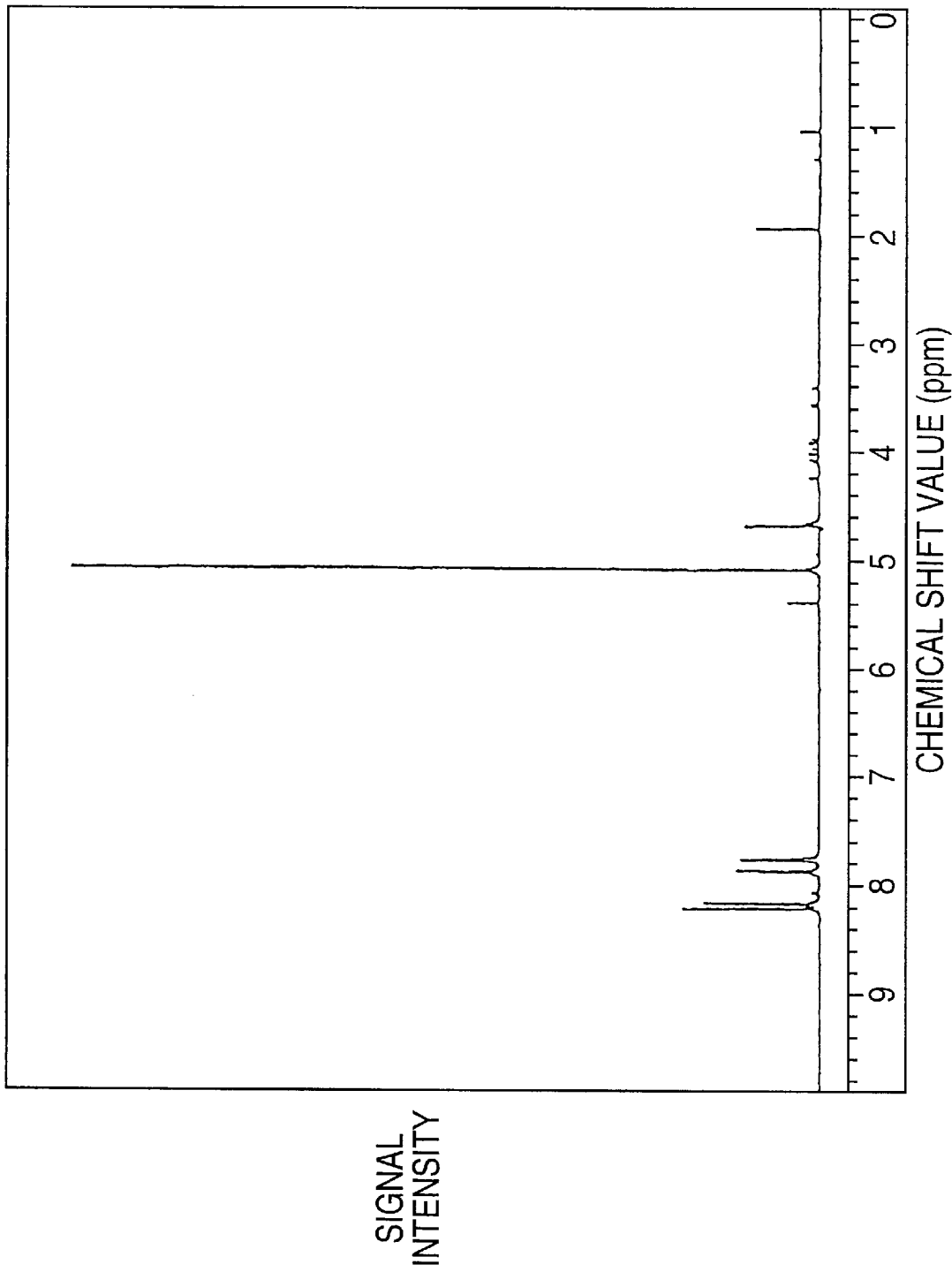
FIG. 14 shows a $^1$H-NMR spectrum of B-UG.
Figure 15:
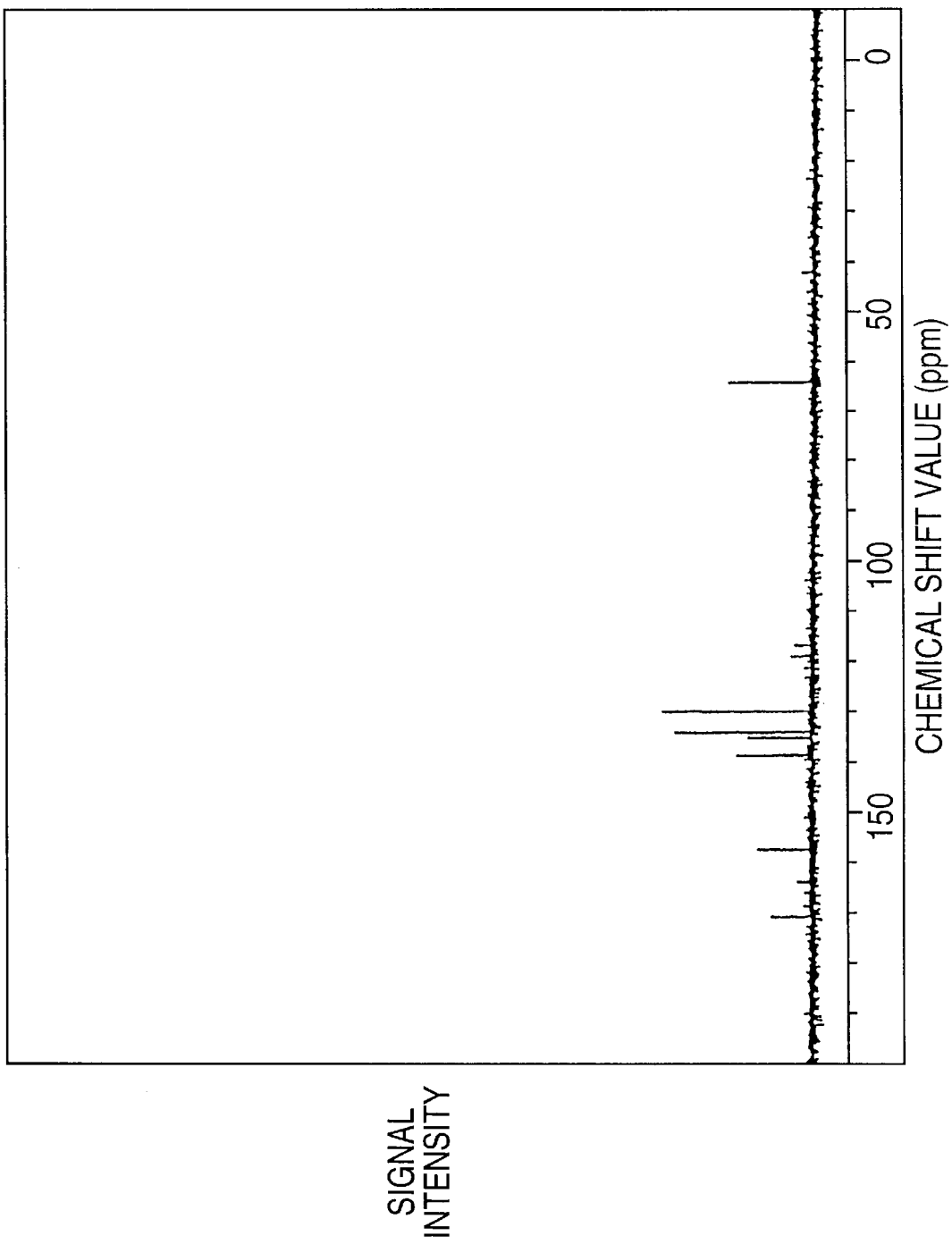
FIG. 15 shows a $^{13}$C-NMR spectrum of B-UG.
Figure 16:
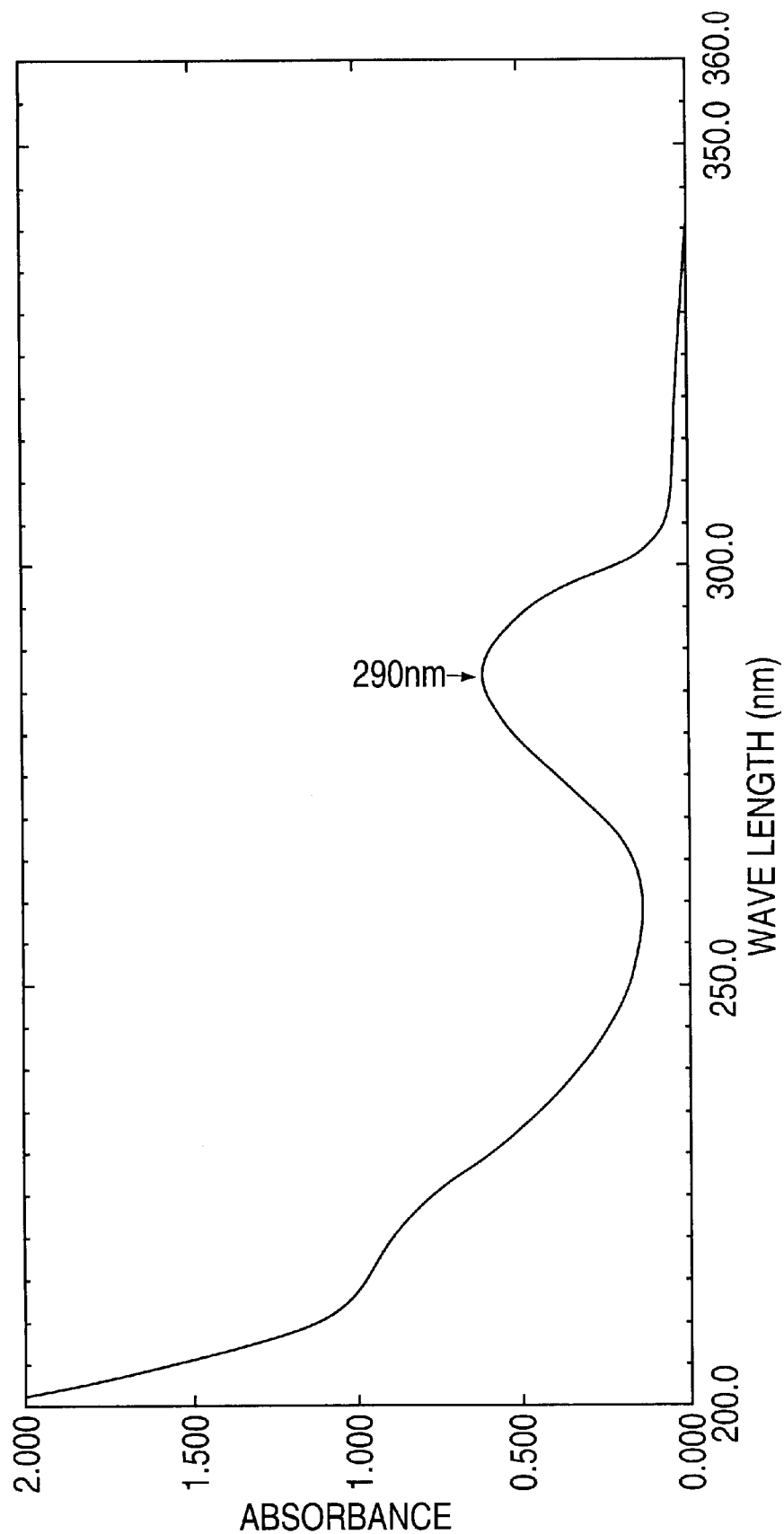
FIG. 16 shows a UV absorption spectrum of B-UG.
Figure 17:
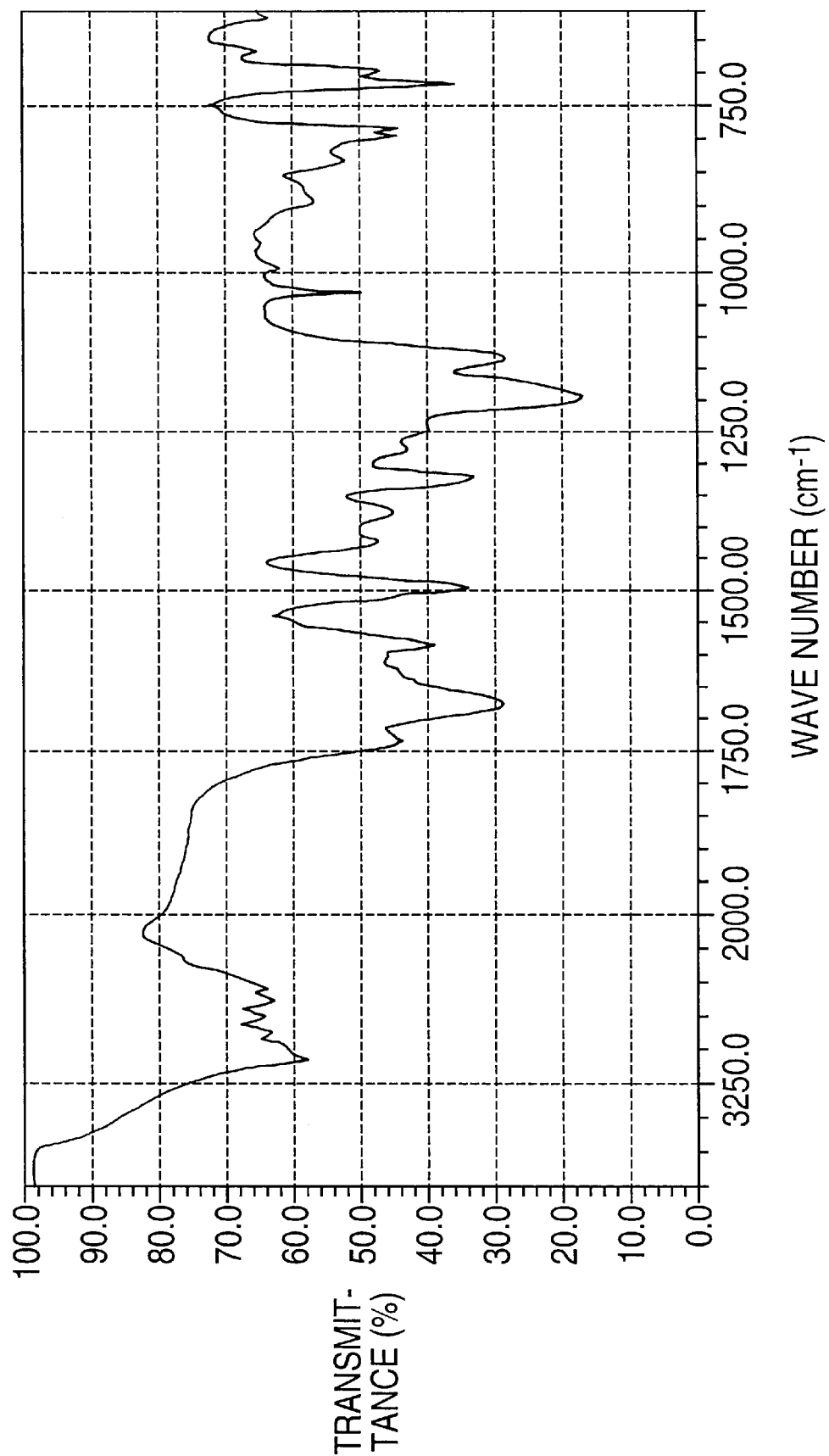
FIG. 17 shows an IR absorption spectrum of B-UG.

The results are shown in FIG. 13 to FIG. 17. Thus, FIG. 13 shows mass spectrum of B-UG in which abscissa indicates m/z values while ordinate indicates relative intensity (%). FIG. 14 shows $^1$H-NMR spectrum of B-UG in which abscissa indicates chemical shift value (ppm) while ordinate indicates the signal intensity. FIG. 15 shows 13C-NMR spectrum of B-UG in which abscissa indicates chemical shift value (ppm) while ordinate indicates the signal intensity. FIG. 16 shows UV absorption spectrum of B-UG in which abscissa indicates wave length (nm) while ordinate indicates absorbance. FIG. 17 shows IR absorption spectrum of B-UG in which abscissa indicates wave number (cm$^{-1}$) while ordinate indicates transmittance (%)

Incidentally, the numbers of assignment of the signals of $^1$H-NMR and $^{13}$C-NMR are as shown in the following formula [XVI].

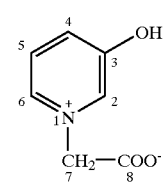

[XVI]

Example 10

(1) The cyclopentenone (6 mg) obtained in Example 1-(1) was dissolved in 1.5 ml of a 5:95 mixture of 10N HCl and methanol and made to react at 37° C. for one night. Silver carbonate was added thereto to neutralize and the supernatant liquid after centrifugation was evaporated to dryness in vacuo and dissolved in 70 μl of a 0.1% aqueous solution of trifluoroacetic acid (TFA). This sample was separated by the following reverse phase HPLC.

Column: TSK gel ODS-80Ts, 20 mm×250 mm (manufactured by Tosoh)

Guard column: TSK guard column ODS-80Ts, 20×50 mm (manufactured by Tosoh)

Solvent A: 0.1% TFA aqueous solution

Solvent B: 0.1% TFA, 50% aqueous solution of acetonitrile

Elution: solvent A (20 minutes)→a linear concentration gradient (40 minutes) from solvent A to solvent B Flow rate: 9 ml/minute Detection: absorbance at 215 nm The main peak was noted at the retention time of 48.58 minutes and this peak was collected and evaporated to dryness in vacuo to give MC2.

(2) MC2 obtained in Example 10-(1) was dissolved in 1 mM HCl and made to react at 37° C. for 16 hours. The reaction solution was separated by the following reverse phase HPLC.

Column: TSK gel ODS-80Ts, 4.6 mm×250 mm (manufactured by Tosoh)

Solvent: 0.1% TFA aqueous solution

Flow rate: 1 ml/minute

Detection: absorbance at 215 nm

Since a main peak at the retention time of 6.6 minutes was newly found, it was collected and concentrated and evaporated to dryness in vacuo to give HMC2.

(3) The cyclopentenone obtained in Example 1-(1) was dissolved in 300 mM sulfuric acid to make 8.6 mg/ml and then made to react at 100° C. for 4 hours. The reaction product was separated by the same reverse phase HPLC as in Example 10-(1) to collect a main peak having a retention time of 6.6 minutes.

Example 11

(1) Mass spectrum of MC2 was conducted using a mass spectrometer DX302 (manufactured by Nippon Denshi). Further, it was dissolved in 0.1N heavy hydrochloric acid and nuclear magnetic resonance (NMR) spectrum was measured by JNM-A500 (manufactured by Nippon Denshi). Ultraviolet (UV) absorption spectrum was measured using a UV-2500 spectrophotomer (manufactured by Shimadzu). Infrared (IR) absorption spectrum was measured by FTIR-8000PC infrared spectrophotometer (manufactured by Shimadzu). The result is as follows.

FAB-MS: m/z 143 [M+H]$^+$, 165 [M+Na]$^+$ m-nitrobenzyl alcohol was used as a matrix.

$^1$H-NMR: δ2.23 (1H, dd, J=1.5, 19.0 Hz, 5-H), 2.72 (1H, dd, J=6.0, 19.0 Hz, 5-H), 3.26 (3H, s, 4-OC$\underline{H}_3$), 3.61 (3H, s, 2-OC$\underline{H}_3$), 4.52 (1H, m, 4-H), 6.52 (1H, d, J=3.0 Hz, 3-H)

In the above, chemical shift values of HOD was defined as 4.65 ppm.

$^{13}$C-NMR: δ40.8 (5-C), 56.7 (2-OC$\underline{H}_3$), 58.4 (4-OC$\underline{H}_3$), 74.7 (4-C), 127.3 (3-C), 159.0 (2-C), 203.9 (1-C)

In the above, chemical shift values of dioxane was defined as 67.4 ppm.

UV: λ$_{max}$ 247 nm (water)

IR: ν$^{KBr}_{max}$ cm$^{-1}$ 1728, 1631, 1346, 1120, 1093, 987

From the above, it has been clarified that MC2 is 2,4-dimethoxy-2-cyclopenten-1-one represented by the formula [VI] where R$_3$ and R$_4$ are methyl groups. Incidentally, the numbers of assignment of the peaks of $^1$H-NMR and $^{13}$C-NMR are as shown in the following formula [XVII].

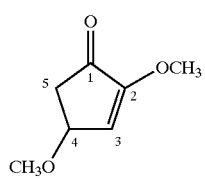

[XVII]

(2) MC2 was dissolved in 0.1N heavy hydrochloric acid and nuclear magnetic resonance (NMR) spectrum was measured by JNM-A500 (manufactured by Nippon Denshi). The result is as follows. $^1$H-NMR: δ2.13 (1H, dd, J=1.5, 19.0 Hz, 5-H), 2.75 (1H, dd, J=6.0, 19.0 Hz, 5-H), 2.76 (2H, t, J=2.5 Hz, 4'-H), 4.78 (1H, m, 4-H), 6.10 (1H, td, J=2.5, 6.5 Hz, 2'-H), 6.40 (1H, d, J=2.5 Hz, 3-H), 7.78 (1H, td, J=2.5, 6.5 Hz, 3'-H)

In the above, chemical shift values of HOD was defined as 4.65 ppm.

$^{13}$C-NMR: δ43.2 (5-C), 44.7 (4'-C), 65.7 (4-C), 93.3 (5'-C), 130.0 (2'-C), 132.5 (3-C), 154.6 (2-C), 166.6 (3'-C), 205.4 (1-C), 207.3 (1'-C)

In the above, chemical shift values of dioxane was defined as 67.4 ppm.

From the above, it has been clarified that HMC2 is a composition consisting of 2,4-dihydroxy-2-cyclopenten-1-one represented by the formula [IV] and 5,5-dihydroxy-2-cyclopenten-1-one represented by the formula [V] in a molar ratio of about 2:1 in 0.1N heavy hydrochloric acid. Incidentally, the numbers of assignment of the peaks of $^1$H-NMR and $^{13}$C-NMR are as shown in the following formulae [XVIII] and [XIX].

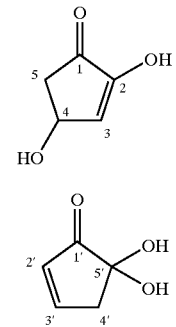

[XVII]

[XIX]

(3) When an NMR spectrum of the fraction of a retention time of 6.6 minutes obtained in Example 10-(3) was measured, the result was entirely same as that in the case of HMC2 of Example 11-(2) whereby it has been clarified that the substance of this fraction is a composition of 2,4-dihydroxy-2-cyclopenten-1-one represented by the formula [IV] and 5,5-dihydroxy-2-cyclopenten-1-one represented by the formula [V] in a molar ratio of about 2:1.

Figure 18:
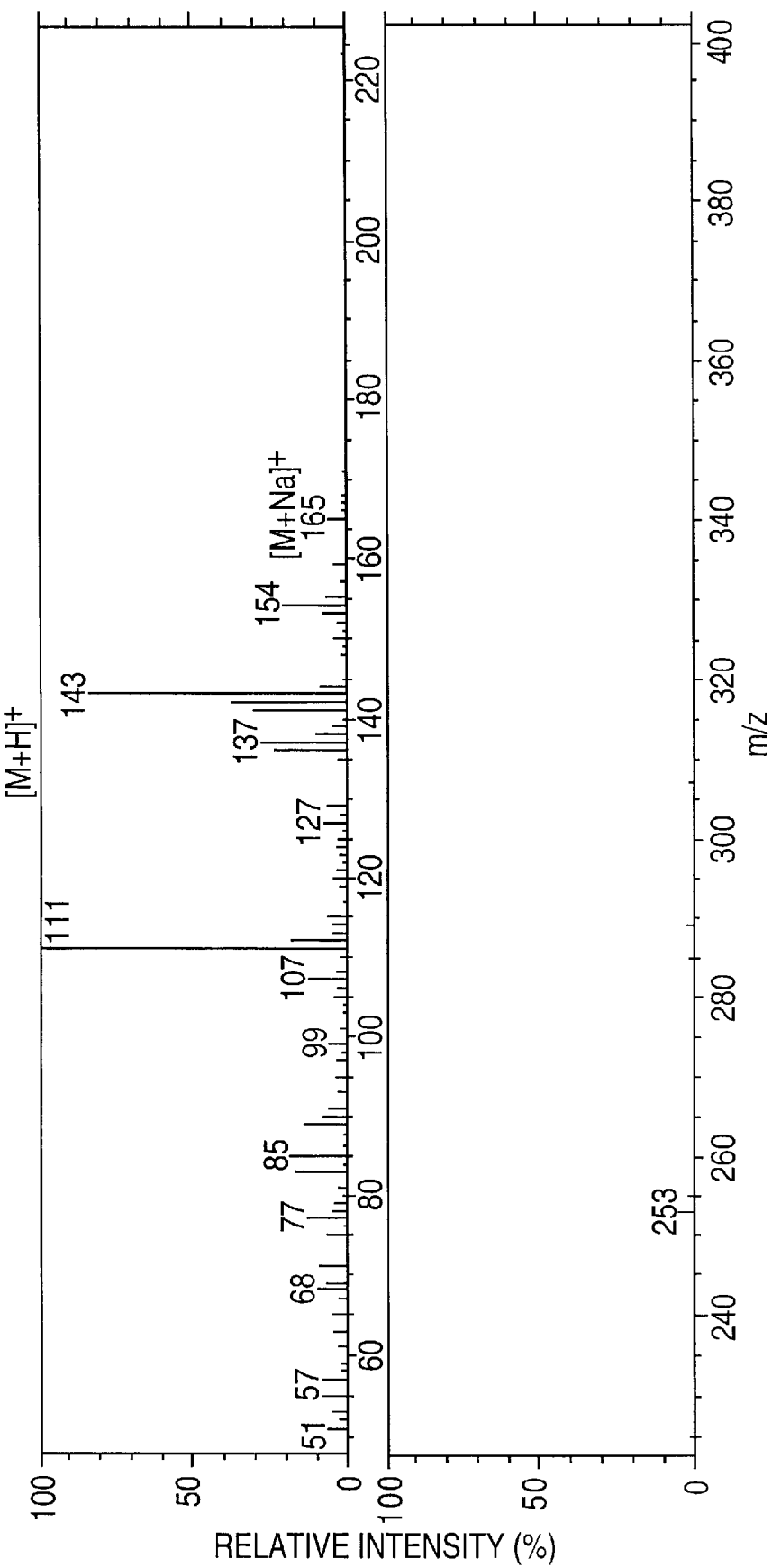
FIG. 18 shows a mass spectrum of MC2.
Figure 19:
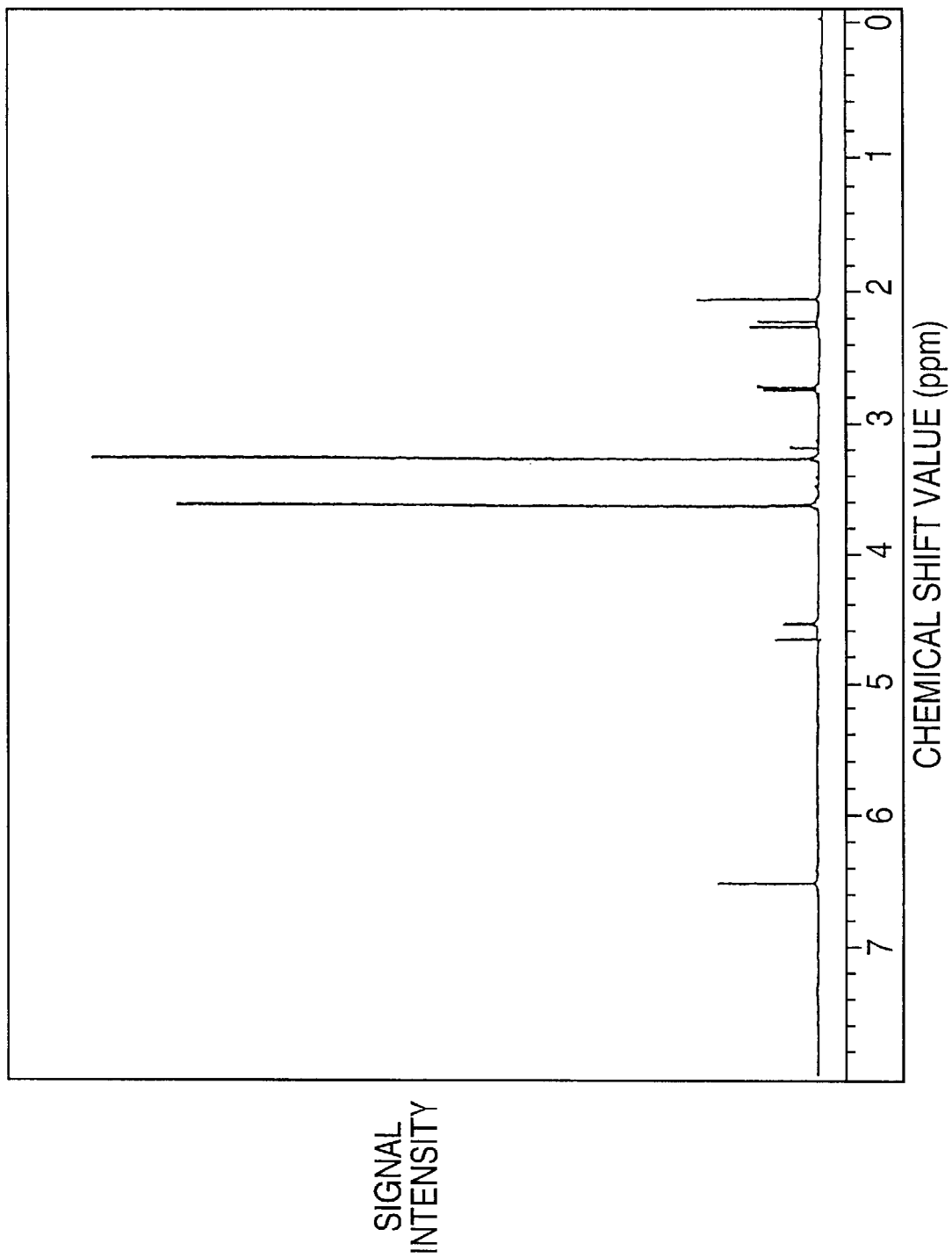
FIG. 19 shows a $^1$H-NMR spectrum of MC2.
Figure 20:
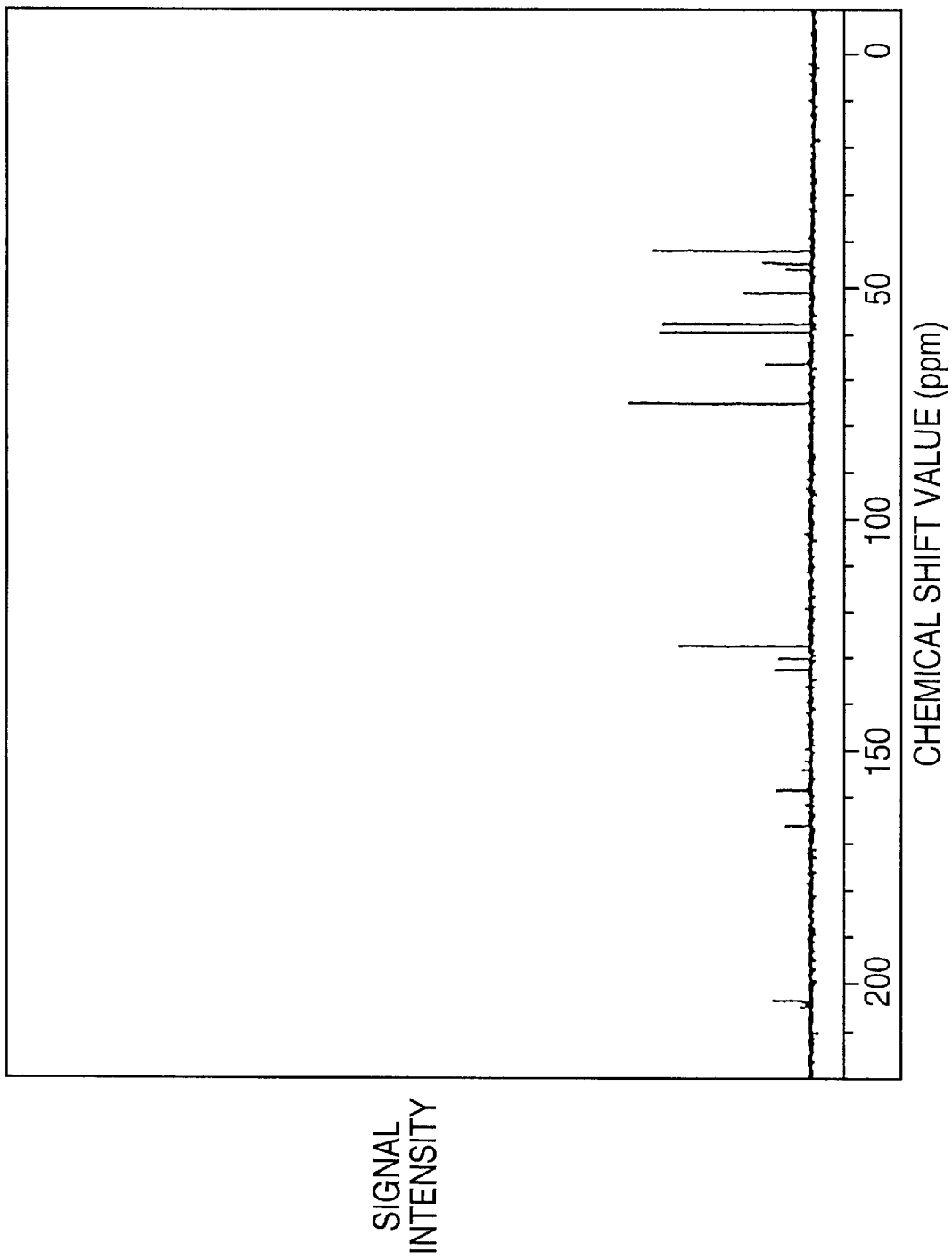
FIG. 20 shows a $^{13}$C-NMR spectrum of MC2.
Figure 21:
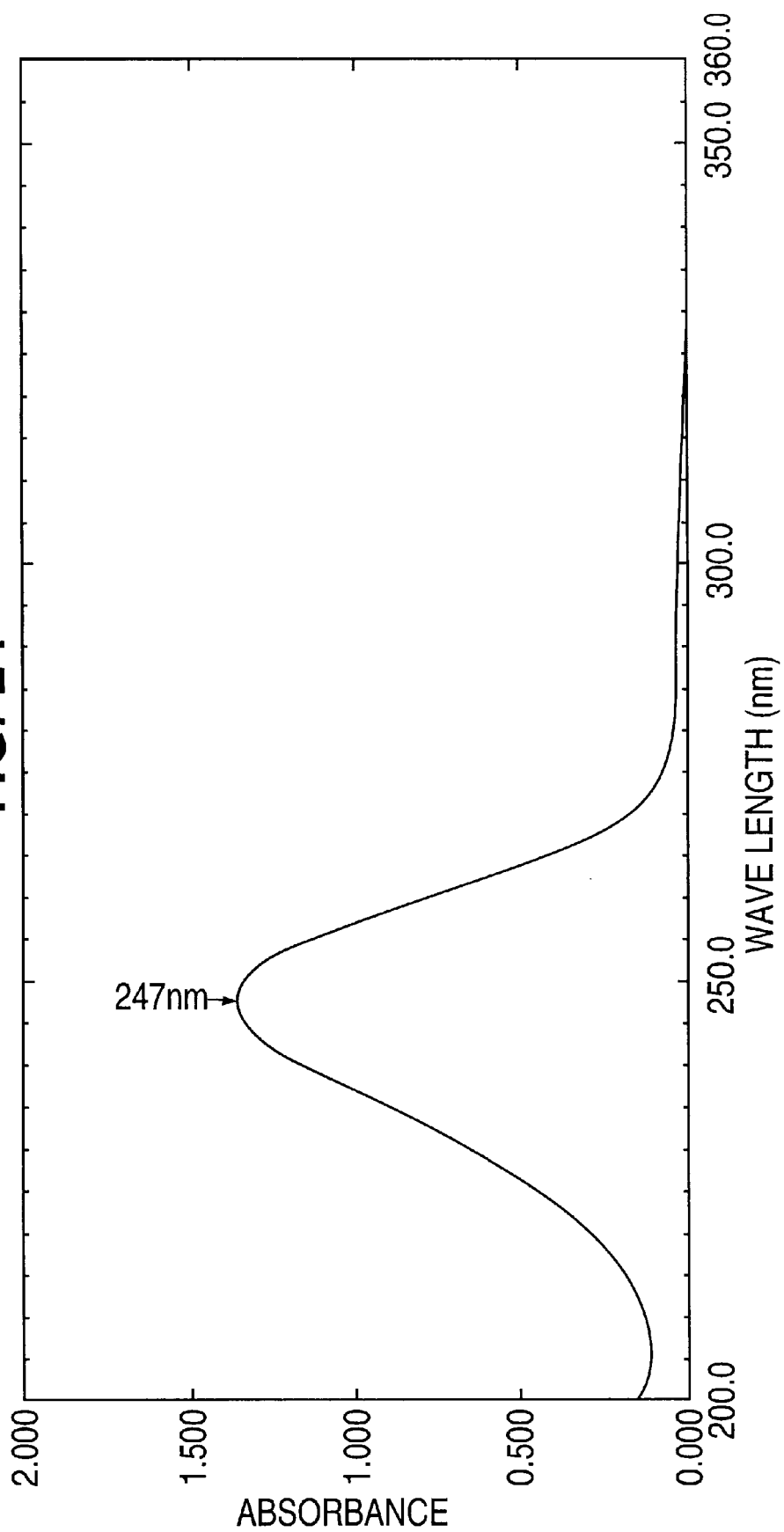
FIG. 21 shows a UV spectrum of MC2.
Figure 22:
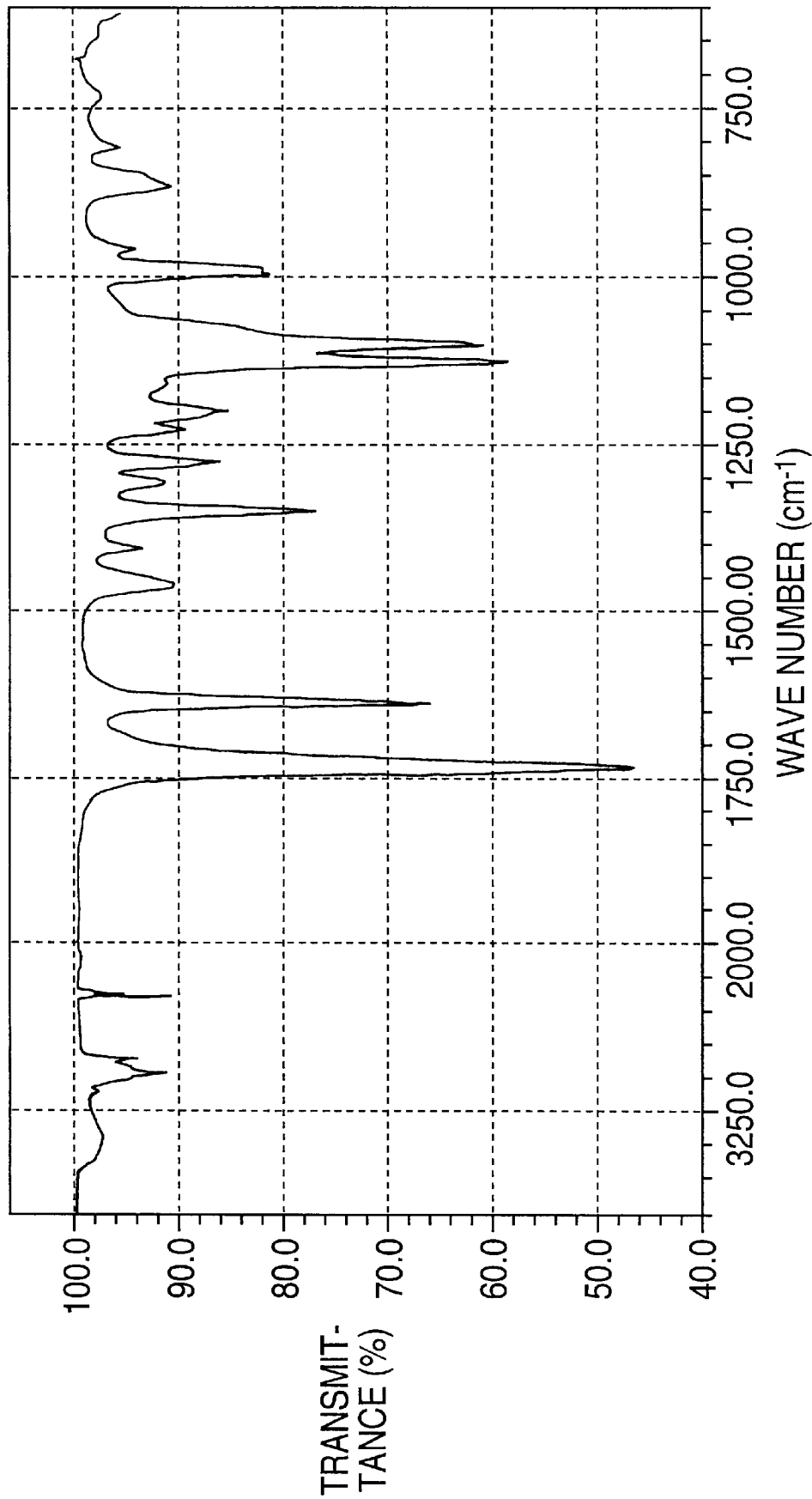
FIG. 22 shows an IR spectrum of MC2.
Figure 23:
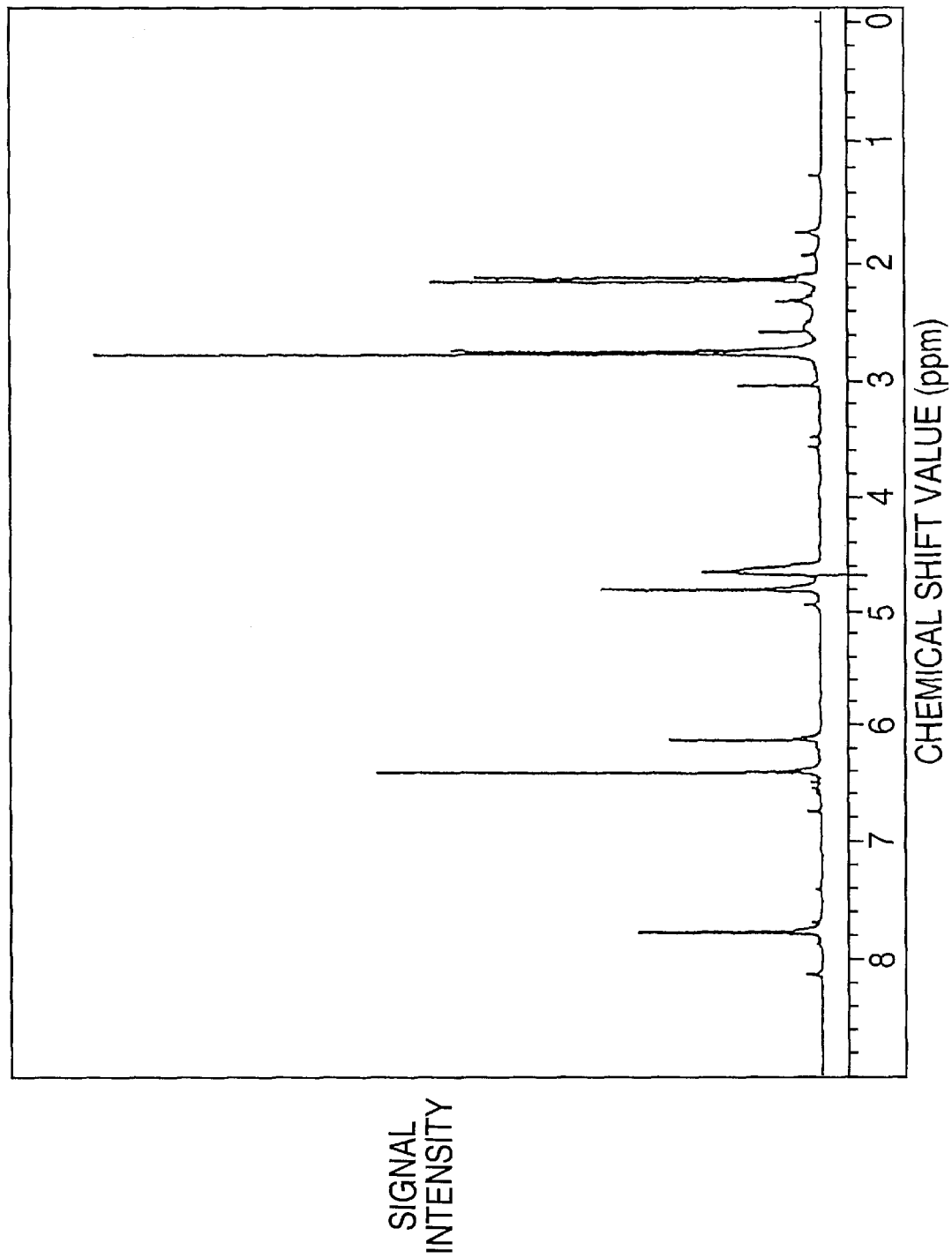
FIG. 23 shows a $^1$H-NMR spectrum of HMC2.
Figure 24:
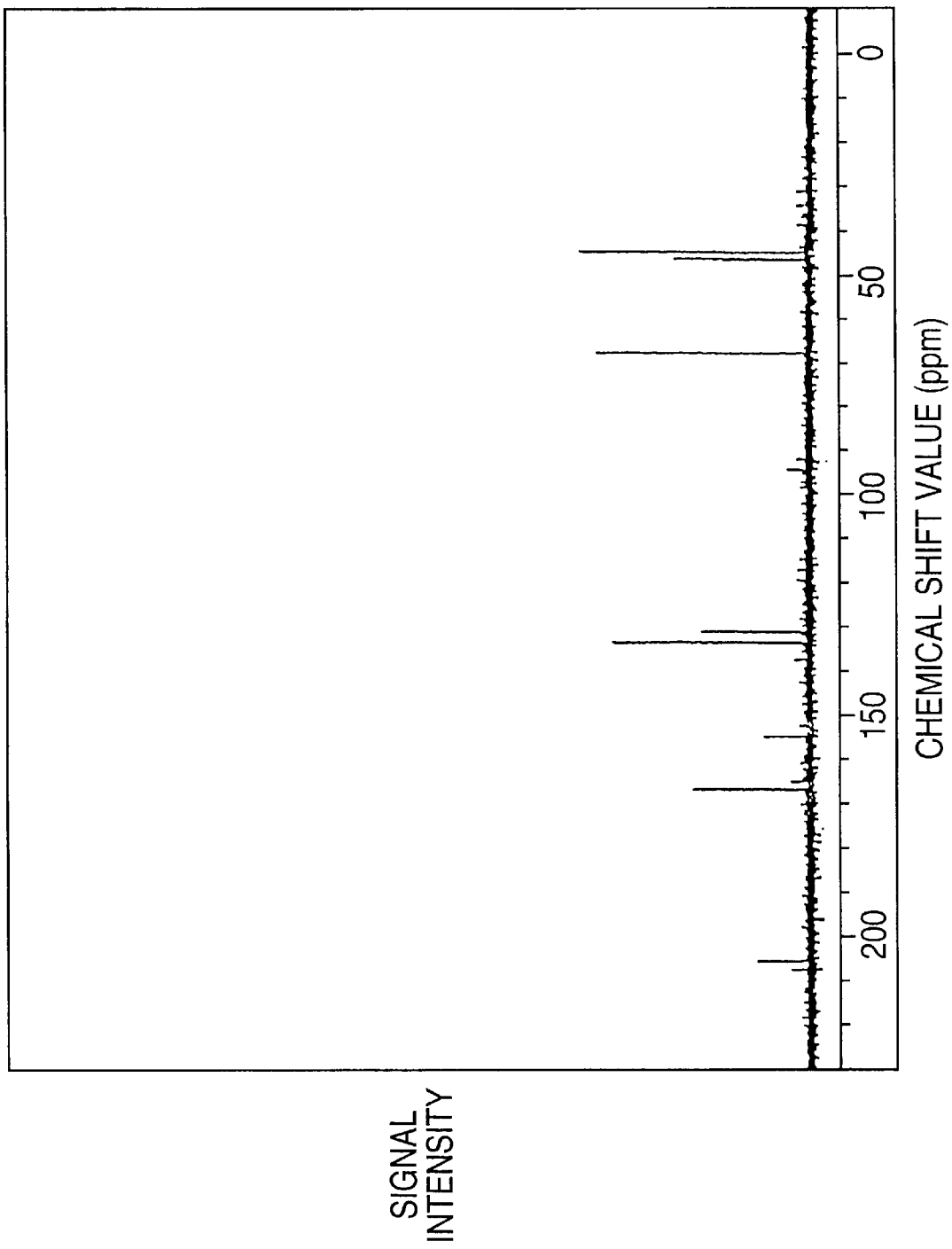
FIG. 24 shows a $^{13}$C-NMR spectrum of HMC2.

The results are shown in FIG. 18 to FIG. 24. Thus, FIG. 18 shows mass spectrum of MC2 in which abscissa indicates m/z values while ordinate indicates relative intensity (%). FIG. 19 shows $^1$H-NMR spectrum of MC2 and FIG. 20 shows $^{13}$C-NMR spectrum of MC2. In FIGS. 19 and 20, abscissa indicates chemical shift value (ppm) while ordinate indicates the signal intensity. FIG. 21 shows UV spectrum of MC2 in which abscissa indicates wave length (nm) while ordinate indicates absorbance. FIG. 22 shows IR spectrum of MC2 in which abscissa indicates wave number (cm$^{-1}$) while ordinate indicates transmittance (%). FIG. 23 shows $^1$H-NMR spectrum of HMC2 and FIG. 24 shows $^{13}$C-NMR spectrum of HMC2. In FIGS. 23 and 24, abscissa indicates chemical shift value (ppm) while ordinate indicates the signal intensity.

Example 12

The growth inhibiting activity of a 1 mM aqueous solution of MC2 and a 350 μM aqueous solution of HMC2 obtained in Example 10 to HL-60 cells was measured by the same way as in Example 3.

The result was that growth of the cells was inhibited in the section to which the 1 mM MC2 was added (final concentration: 100 µM) and in the section to which the 350 µM HMC2 was added (final concentration: 35 µM) and that apoptotic body was observed under an optical microscope.

Example 13

(1) An aqueous solution (500 ml) of 30 mM D-glucuronic acid and 30 mM tyrosine (both manufactured by Nacalai Tesque) was adjusted to pH 3 with 1N HCl and heated at 121° C. for 4 hours.

(2) The heat-treated solution obtained in Example 13-(1) was extracted with ethyl acetate and the liquid obtained by concentration of the extract in vacuo was separated by the following silica gel column chromatography.

Filler: silica gel BW-300SP for column chromatography (manufactured by Fuji Silycia)

Column size: 2.0 cm×45 cm

Mobile phase: hexane and ethyl acetate in a ratio of 3:7

An elution was carried out by applying an air pressure of 0.25 kgf/cm$^2$ using a pump. The first 40 ml were discarded and then fractionation was carried out for each 4 ml. The 6th to the 11th fractions were collected and concentrated and evaporated to dryness in vacuo followed by dissolving in 5 ml of a 3:2 mixture of hexane and ethyl acetate.

A silica gel column chromatography of this solution was carried out in the same way as mentioned above using a 3:2 mixture of hexane and ethyl acetate as a mobile phase. The first 30 ml were discarded and then fractionation was carried out for each 6 ml. The 19th to the 32nd fractions were collected and concentrated and evaporated to dryness in vacuo followed by dissolving in 1 ml of a 50% aqueous solution of acetonitrile.

(3) The partially purified specimen obtained in Example 13-(2) was further purified by the following reverse phase HPLC.

Column: CAPCELL PAK $C_{18}$ SG300 Å 5 µm, 6×250 mm (manufactured by Shiseido)

Flow rate: 1 ml/minute

Mobile phase: A 0.1% aqueous solution of trifluoroacetic acid (TFA)

B 50% aqueous solution of acetonitrile containing 0.1% TFA

Elution (concentration of the mobile phase B): 55% (0–8 minutes)→55%~80% linear concentration gradient (8–13 minutes)→100% (13 minutes and thereafter)

Detection: absorbance at 215 nm

A sample (50 µl) was charged and a main peak at the retention time of 18.7 minutes was collected. This operation was carried out for 19 times and the collected solution was evaporated to dryness in vacua to give 4.7 mg of S-1127.

Figure 25:
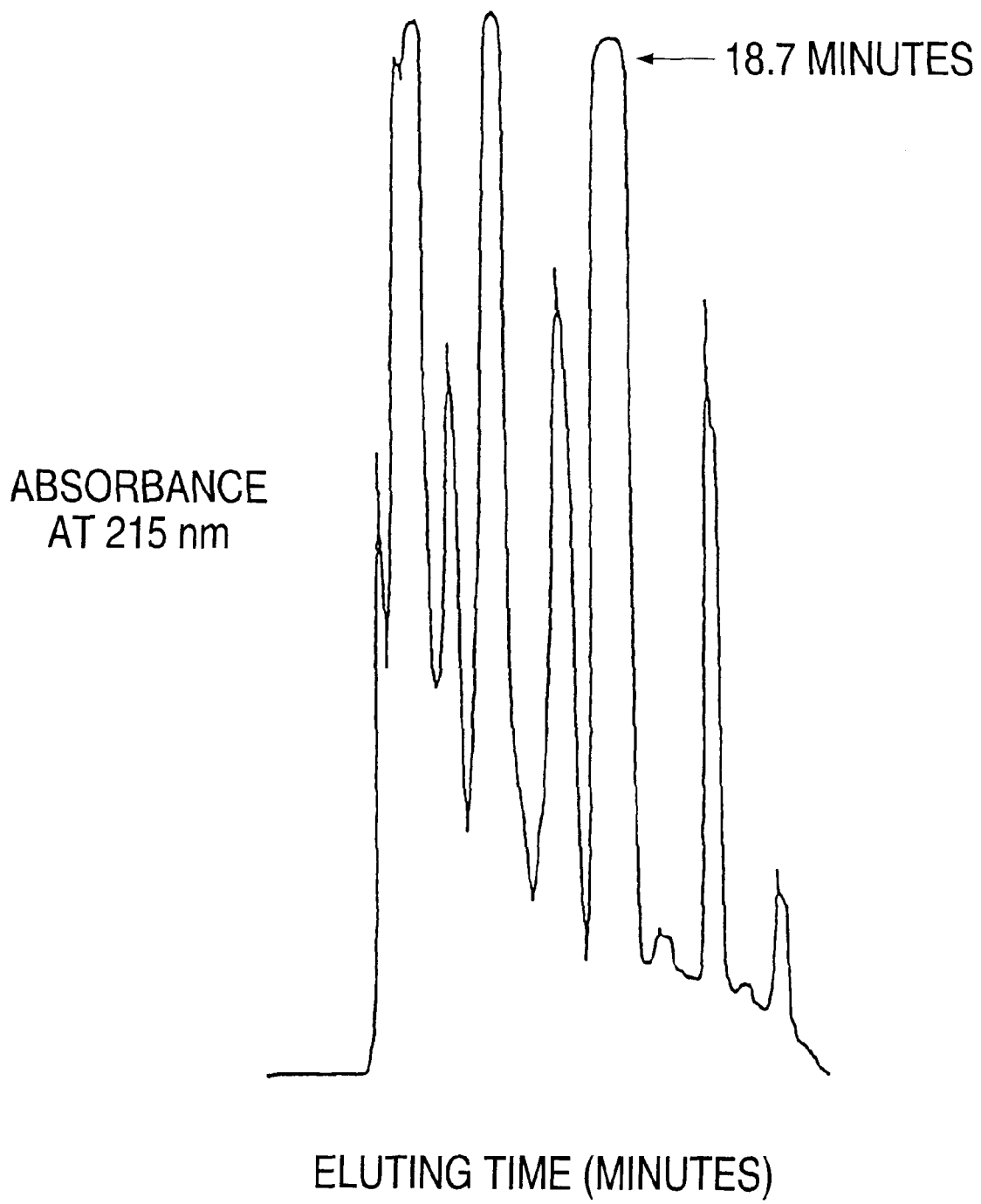
FIG. 25 shows a relation between eluting time of reverse phase HPLC of S-1127 and absorbance at 215 nm.

The result is shown in FIG. 25. Thus, FIG. 25 shows a relation between eluting time and absorbance at 215 nm in which abscissa indicates eluting time (minutes) while ordinate indicates absorbance at 215 nm.

Example 14

A fast atom bombardment mass spectrometry (FAB-MS) of S-1127 isolated in Example 13 was conducted using a mass spectrometer DX302 (manufactured by Nippon Denshi). Further, it was dissolved in heavy dimethylsulfoxide and its structure was analyzed by means of nuclear magnetic resonance (NMR). JNM-A500 (manufactured by Nippon Denshi) was used as a nuclear magnetic resonance device. Ultraviolet (UV) absorption spectrum was measured using a UV-2500 spectrophotomer (manufactured by Shimadzu). Infrared absorption spectrum (IR) was measured by a diffuse reflectance method. The results are as given below.

FAB-MS: m/z 253 [M–H]$^-$

Glycerol was used as a matrix.

$^1$H-NMR: δ3.54 (2H, d, J=7.5 Hz, 4-H), 6.69 (2H, d, J=8.5 Hz, 7-H), 6.80 (2H, d, J=9.0 Hz, 11-H), 6.88 (1H, t, J=7.5 Hz, 3-H), 6.97 (2H, d, J=8.5 Hz, 6-H), 7.00 (2H, d, J=9.0 Hz, 10-H), 9.25 (1H, s, 8-OH), 9.53 (1H, s, 12-OH), 9.58 (1H, s, 1-H)

In the above, the chemical shift value of the residual proton of heavy dimethyl sulfoxide was expressed as 2.49 ppm.

$^{13}$C-NMR: δ34.3 (4-C), 114.9 (11-C), 115.4 (7-C), 122.6 (9-C), 128.3 (5-C), 129.3 (6-C), 130.6 (10-C), 142.6 (2-C), 154.1 (3-C), 155.9 (8-C), 157.0 (12-C), 194.5 (1-C)

In the above, chemical shift values of heavy dimethylsulfoxide was defined as 39.5 ppm.

UV: $\lambda_{max}$ 225, 278 nm (methanol)

IR: $\nu^{KBr}_{max}$ cm$^{-1}$ 3294, 1672, 1610, 1514, 1228, 837

From the above, it has been clarified that S-1127 is 2,4-bis(p-hydroxyphenyl)-2-butenal represented by the formula [XIII].

Figure 26:
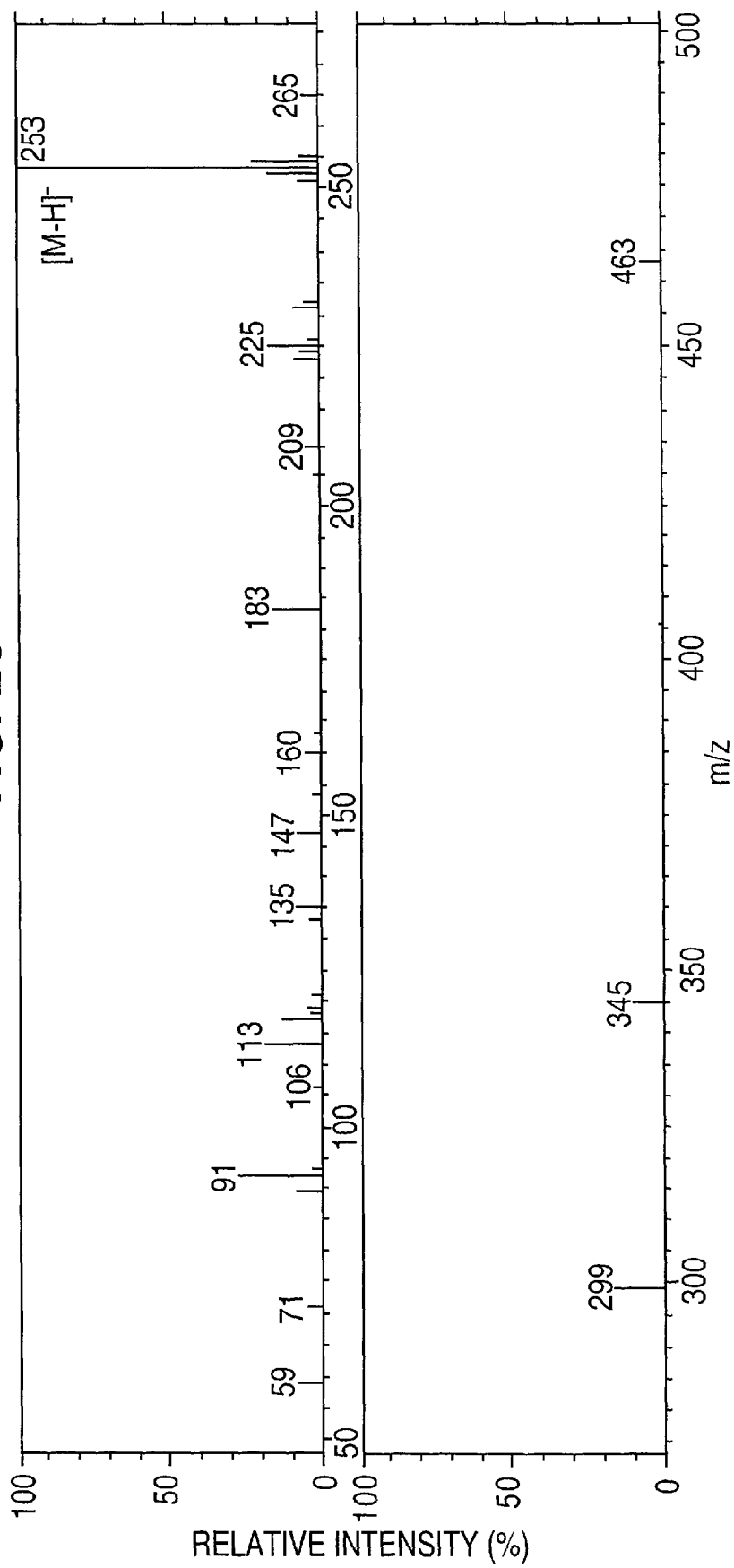
FIG. 26 shows a mass spectrum of S-1127.
Figure 27:
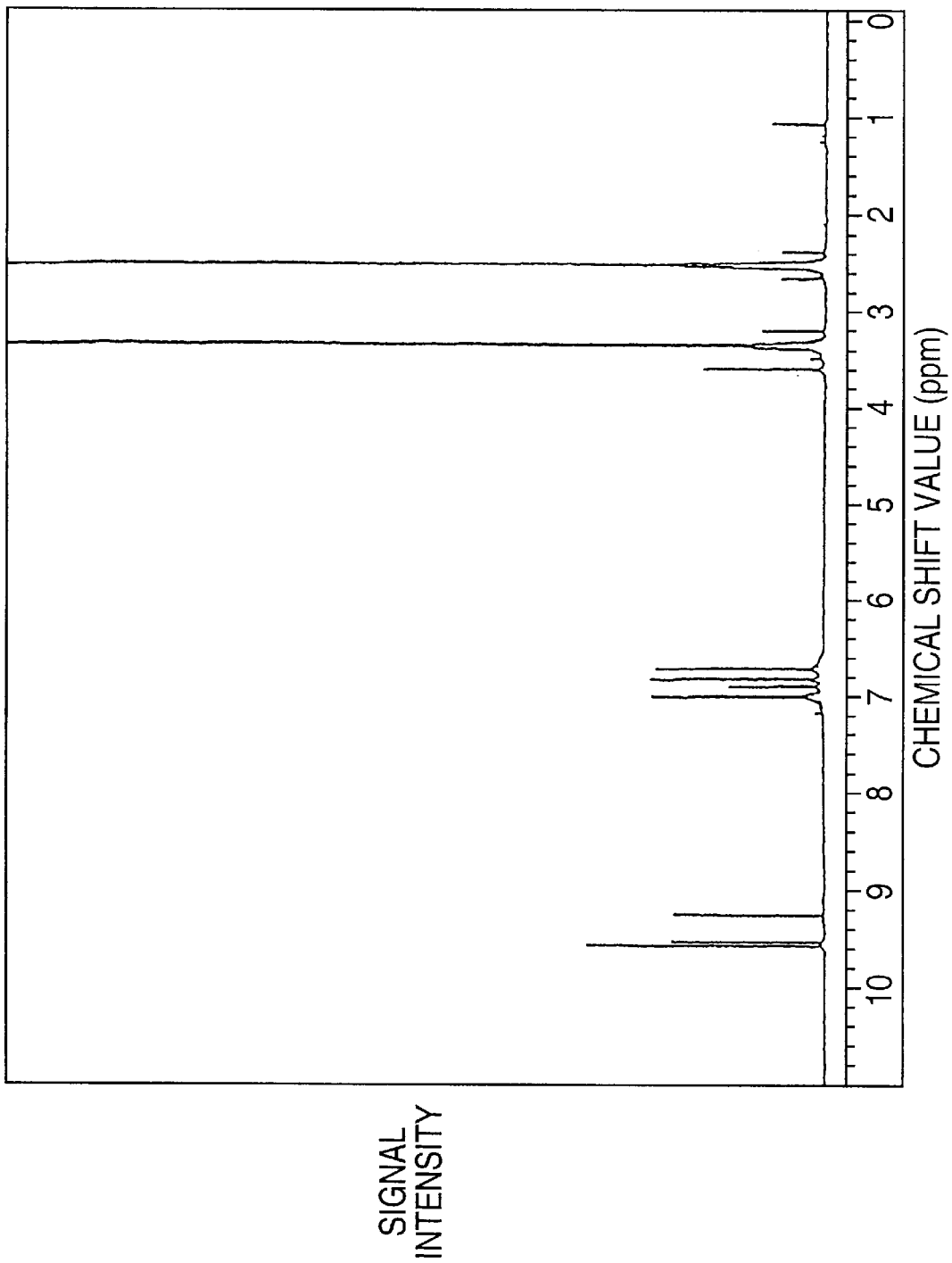
FIG. 27 shows a $^1$H-NMR spectrum of S-1127.
Figure 28:
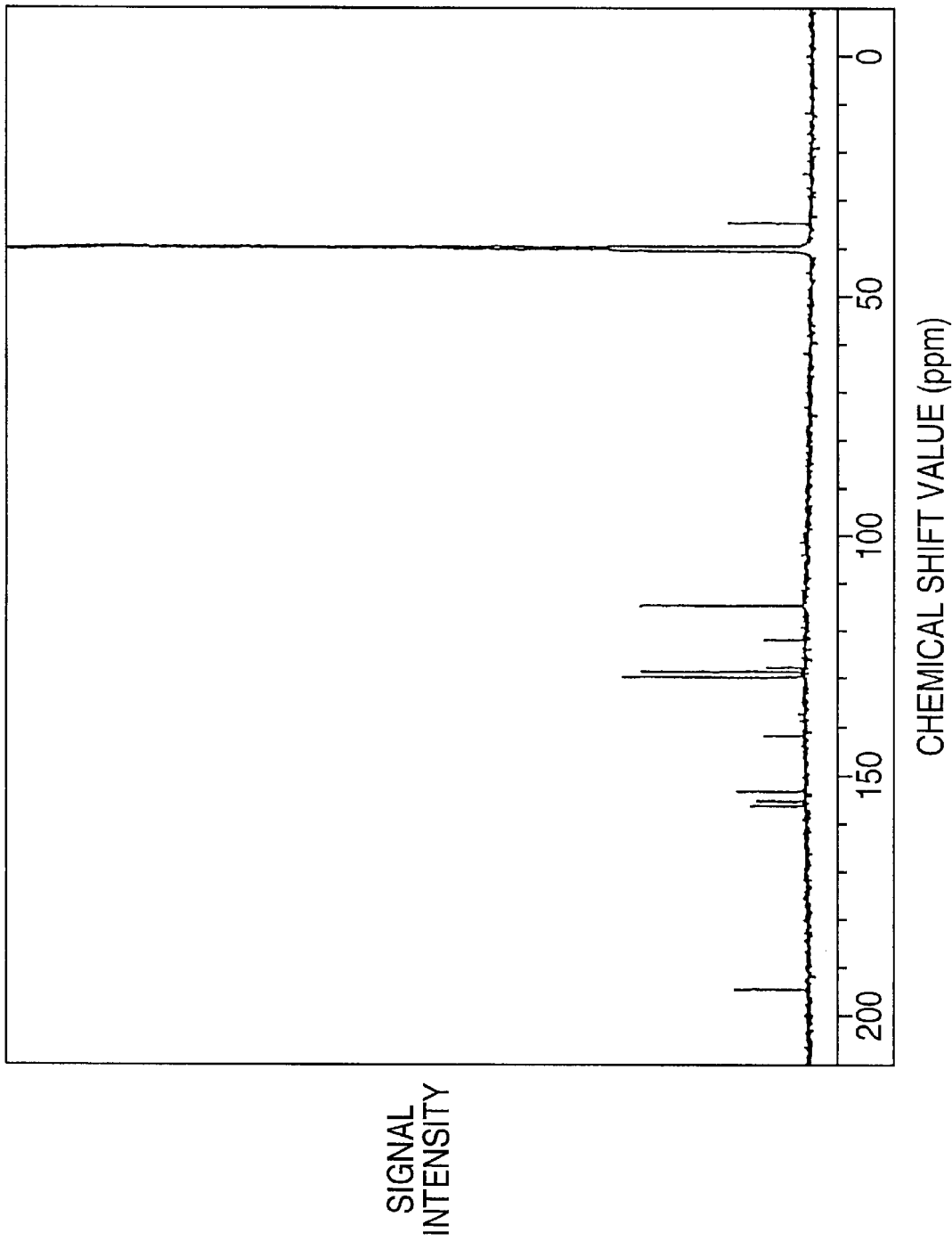
FIG. 28 shows a $^{13}$C-NMR spectrum of S-1127.
Figure 29:
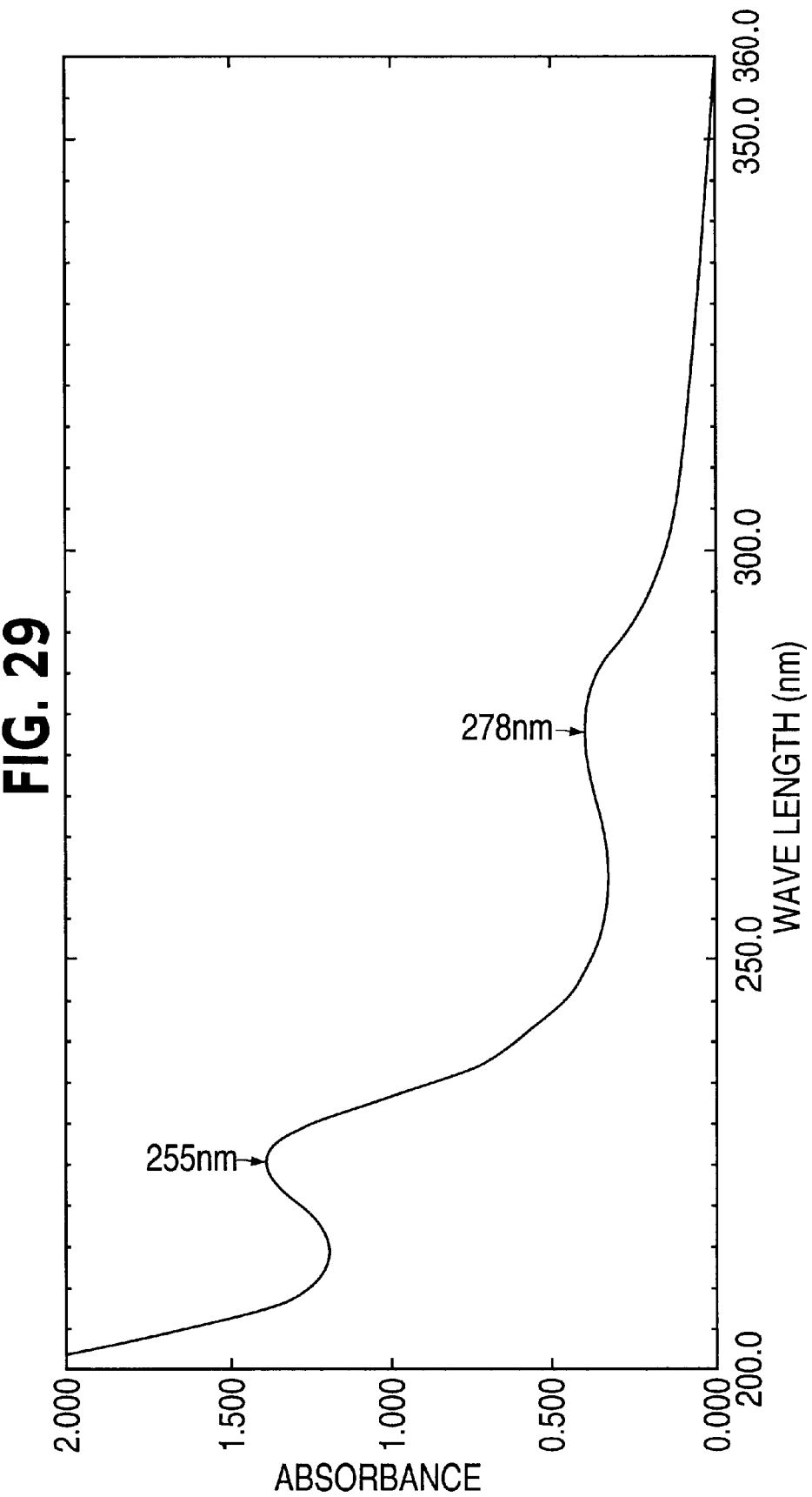
FIG. 29 shows a UV absorption spectrum of S-1127.
Figure 30:
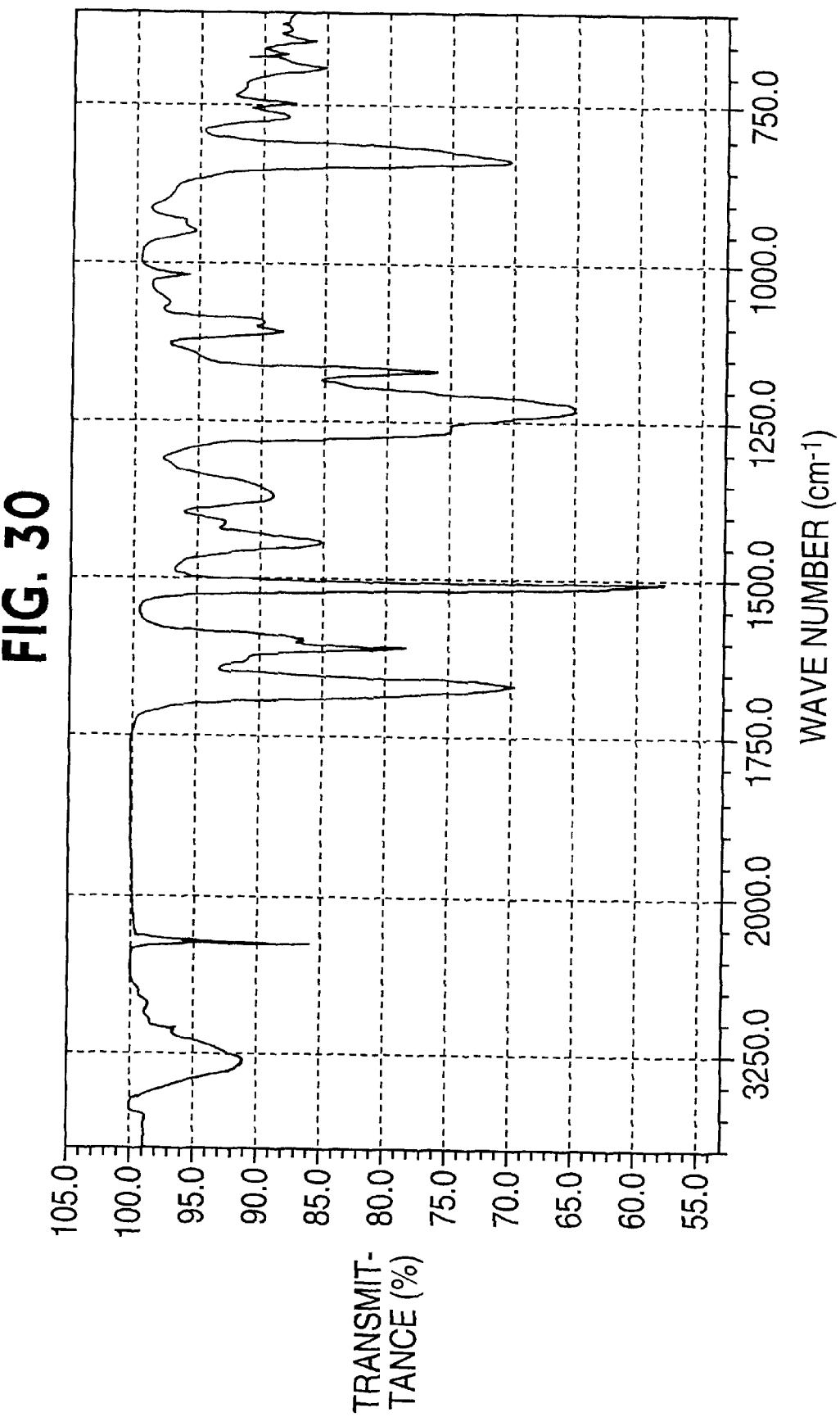
FIG. 30 shows an IR absorption spectrum of S-1127.

The results are shown in FIG. 26 to FIG. 30. Thus, FIG. 26 shows mass spectrum of S-1127 in which abscissa indicates m/z values while ordinate indicates relative intensity (%). FIG. 27 shows $^1$H-NMR spectrum of S-1127 in which abscissa indicates chemical shift value (ppm) while ordinate indicates the signal intensity. FIG. 28 shows $^{13}$C-NMR spectrum of S-1127 in which abscissa indicates chemical shift value (ppm) while ordinate indicates the signal intensity. FIG. 29 shows UV absorption spectrum of S-1127 in which abscissa indicates wave length (nm) while ordinate indicates absorbance. FIG. 30 shows IR absorption spectrum of S-1127 in which abscissa indicates wave number (cm$^{-1}$) while ordinate indicates transmittance (%).

Incidentally, the numbers of assignment of the signals of $^1$H-NMR and $^{13}$C-NMR are as shown in the following formula [XX].

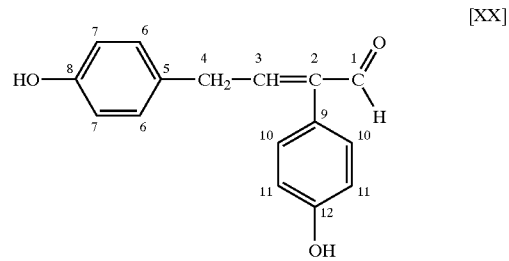

Example 15

HL-60 cells (ATCC CCL240) which were incubated at 37° C. in an RPMI 1640 medium (manufactured by Nissui) containing 10% of fetal calf serum (manufactured by Gibco) treated at 56° C. for 30 minutes were suspended in the above medium to make the concentration 2.5×10$^5$ cells/4.5 ml. To this suspension was added 0.5 ml of 10 µM, 20 µM, 40 µM or 80 µM aqueous solution of S-1127 followed by incubating at 37° C. in the presence of 5% carbon dioxide gas for 15 hours or 39 hours.

The incubated cells were stained with Trypan Blue and the living cell numbers and the dead cell numbers were counted whereupon it was found that cells were killed after incubation of 15 hours in the section to which 40 μM or more S-1127 were added while, in the section to which 20 μM of S-1127 were added, living cell numbers were significantly decreased after incubation of 39 hours as compared with the water-added control section. When DNA was extracted from the cells after incubation for 15 hours and subjected to an agarose gel electrophoresis, fragmentation of DNA was noted in the section to which 20 μM or more S-1127 were added. Incidentally, such a phenomenon was not observed in the water-added control section.

Figure 31:
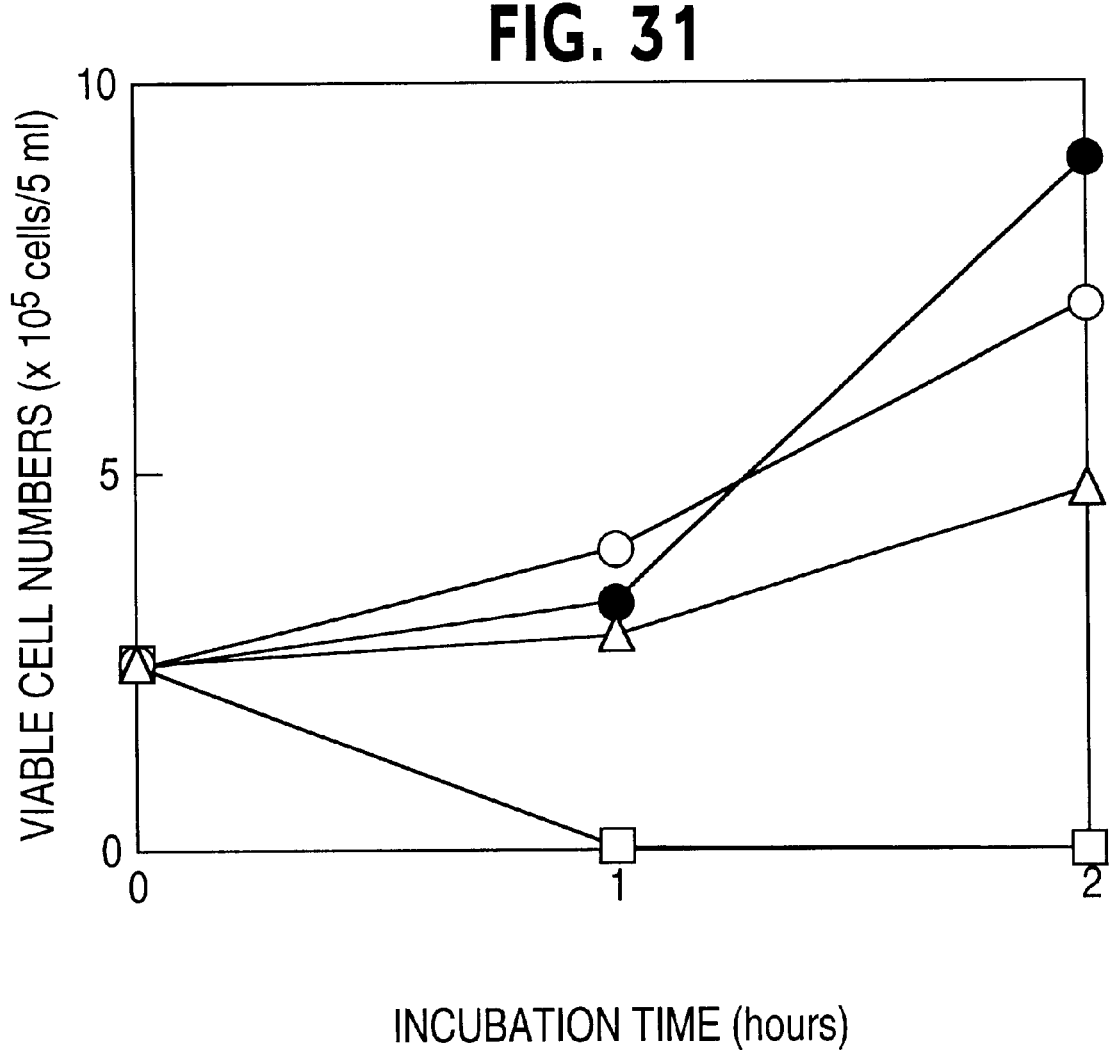
FIG. 31 shows a relation between the incubation time and viable cell numbers.

The result is shown in FIG. 31. Thus, FIG. 31 shows the relation between the incubation time and viable cell numbers in the incubated liquid when S-1127 was added to a culture liquid of HL-60 where abscissa indicates an incubation time (hours) while ordinate indicates viable cell numbers (×10$^5$ cells/5 ml) in the incubated liquid. In FIG. 31, ○ indicates the case where 10 μM of S-1127 was added; Δ indicates the case where 20 μM of S-1127 was added; □ indicates the case where 40 μM of S-1127 was added; X indicates the case where 80 μM of S-1127 was added and ● indicates the control where water was added.

Example 16

A 1M aqueous solution (0.2 ml) of cyclopentenone and 1.8 ml of a 1M aqueous solution of L-cysteine hydrochloride (manufactured by Nacalai Tesque; 103-13) were mixed and made to react at 37° C. for one night. The pH of the reaction solution was about 4. The reaction solution (150 μl) was separated by the following reverse phase HPLC and the peaks of retention time of 28.7 minutes and 29.1 minutes were collected together.

Column: TSK gel ODS-80Ts, 4.6 mm×250 mm (manufactured by Tosoh)

Mobile phase: A 0.1% aqueous solution of trifluoroacetic acid (TFA)

B 50% aqueous solution of acetonitrile containing 0.1% TFA

Elution: mobile phase A (15 minutes)→linear concentration gradient from mobile phase A to mobile phase B (15 minutes)→mobile B (15 minutes)

Flow rate: 1 ml/minute

Detection: absorbance at 210 nm

This operation was carried out for 11 times followed by evaporating to dryness in vacuo to give tCD. A re-chromatography was carried out and LCD1 and LCD2 were obtained from the peak of 28.7 minutes and the peak of 29.1 minutes, respectively.

Figure 32:
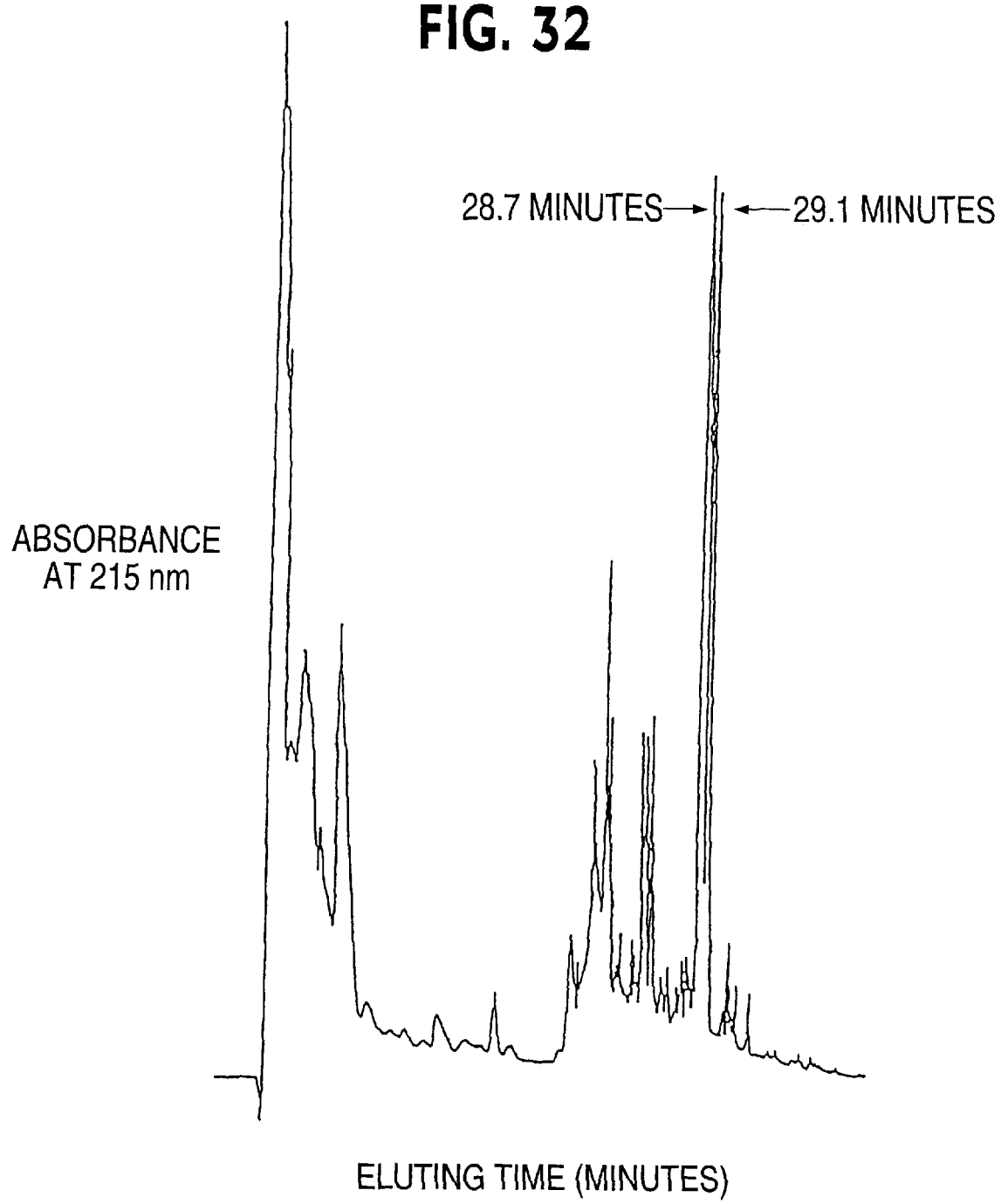
FIG. 32 shows a relation between eluting time and absorbance at 215 nm.

The result is shown in FIG. 32. Thus, FIG. 32 shows a relation between eluting time and absorbance at 215 nm in which abscissa indicates eluting time (minutes) while ordinate indicates absorbance at 215 nm.

Example 17

A fast atom bombardment mass spectrometry (FAB-MS) of LCD1 and LCD2 isolated in Example 16 was conducted using a mass spectrometer DX302 (manufactured by Nippon Denshi). Further, it was dissolved in heavy water and its structures was analyzed by means of nuclear magnetic resonance (NMR). JNM-A500 (manufactured by Nippon Denshi) was used as a nuclear magnetic resonance device. Ultraviolet (UV) absorption spectrum was measured by a UV-2500 spectrophotometer (manufactured by Shimadzu); and infrared absorption spectrum (IR) was measured by an FTIR-8000 infrared spectrophotometer (manufactured by Shimadzu). The results are as given below.

LCD1

FAB-MS: m/z 404 [M–H]$^-$

Glycerol was used as a matrix.

$^1$H-NMR: δ2.05 (1H, dd, J=4.0, 15.5 Hz, 10-H), 2.40 (1H, dd, J=9.5, 13.0 Hz, 8-H), 2.61 (1H, dd, J=8.0, 13.0, 8-H), 2.79 (1H, dd, J=11.0, 15.5 Hz, 10-H), 3.05 (1H, dd, J=7.0, 15.0 Hz, 1'-H), 3.10 (1H, d, J=11.0 Hz, 5-H), 3.13 (1H, dd, J=4.0, 15.0 Hz, 1'-H), 3.19 (1H, dd, J=6.0, 11.0 Hz, 5-H), 3.22 (1H, dd, J=8.5, 12.5 Hz, 13-H), 3.40 (1H, m, 9-H), 3.50 (1H, dd, J=8.5, 12.5 Hz, 13-H), 4.15 (1H, dd, J=4.0, 7.0, 2'-H), 4.30 (1H, d, J=6.0 Hz, 4-H), 4.82 (1H, t, J=8.5 Hz, 1-H)

In the above, chemical shift values of HOD was defined as 4.65 ppm.

$^{13}$C-NMR: δ31.9 (13-C), 32.1 (1'-C), 37.7 (9-C), 40.9 (10-C), 41.9 (5-C), 47.0 (8-C), 53.1 (2'-C), 61.8 (1-C), 63.1 (4-C), 83.8 (7-C), 88.7 (11-C), 171.0 (4'-C), 171.4 (3'-C), 173.7 (2-C)

In the above, chemical shift values of dioxane was defined as 67.4 ppm.

UV: terminal absorption (water)

IR: $\nu^{KBr}_{max}$ cm$^{-1}$ 2937, 1730, 1664, 1390, 1195, 1141

LCD2

FAB-MS: m/z 404 [M–H]$^-$

Glycerol was used as a matrix.

$^1$H-NMR: δ2.25 (2H, m, 8-H, 10-H), 2.63 (1H, dd, J=8.0, 14.0, 8-H), 2.95 (1H, dd, J=6.5, 14.5 Hz, 10-H), 3.04 (1H, dd, J=7.0, 15.0 Hz, 1'-H), 3.12 (1H, dd, J=4.5, 15.0 Hz, 1'-H), 3.12 (1H, d, J=11.0 Hz, 5-H), 3.18 (1H, dd, J=5.5, 11.0 Hz, 5-H), 3.26 (1H, dd, J=8.5, 12.5 Hz, 13-H), 3.49 (1H, dd, J=8.5, 12.5 Hz, 13-H), 3.63 (1H, m, 9-H), 4.16 (1H, dd, J=4.5, 7.0, 2'-H), 4.29 (1H, d, J=5.5 Hz, 4-H), 4.85 (1H, t, J=8.5 Hz, 1-H)

In the above, chemical shift values of HOD was defined as 4.65 ppm.

Figure 33:
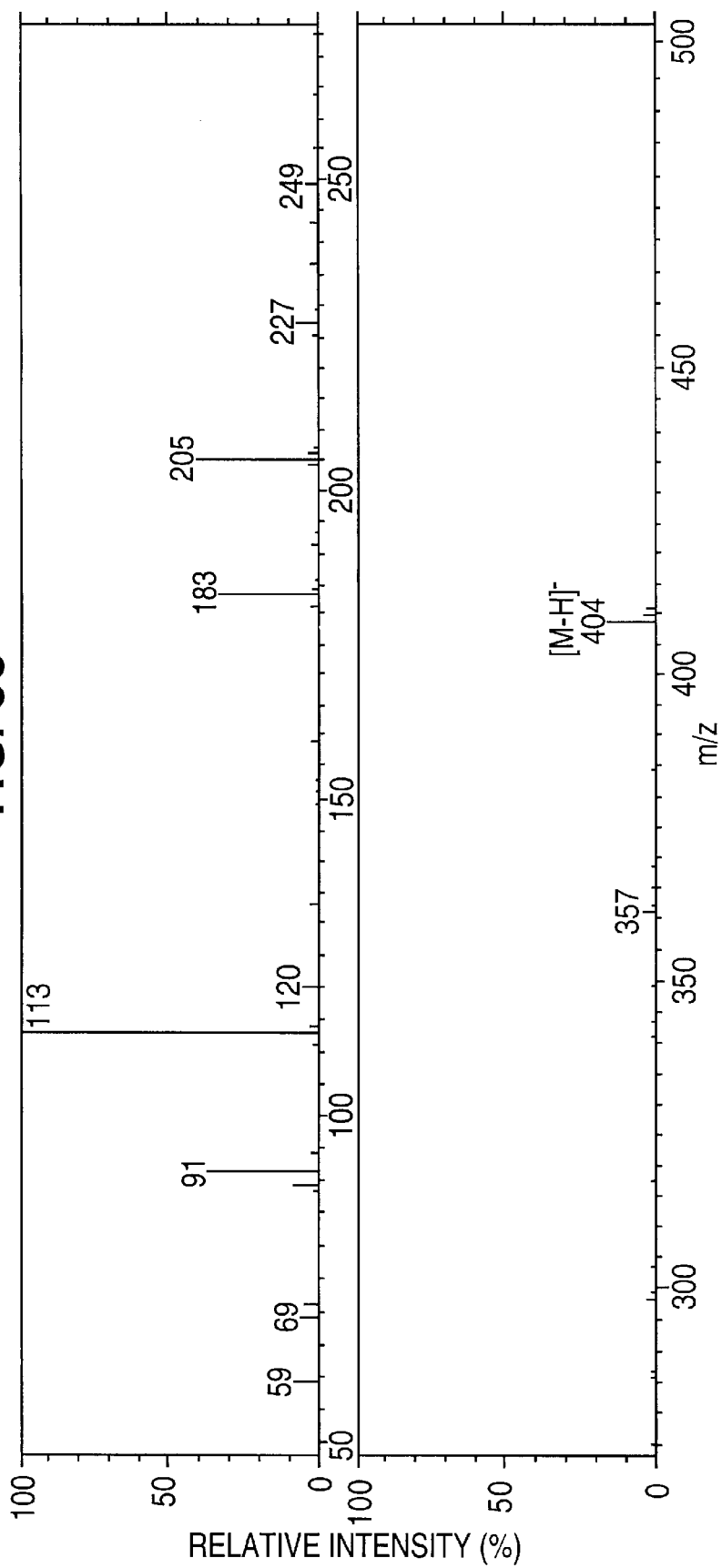
FIG. 33 shows a mass spectrum of LCD1.
Figure 34:
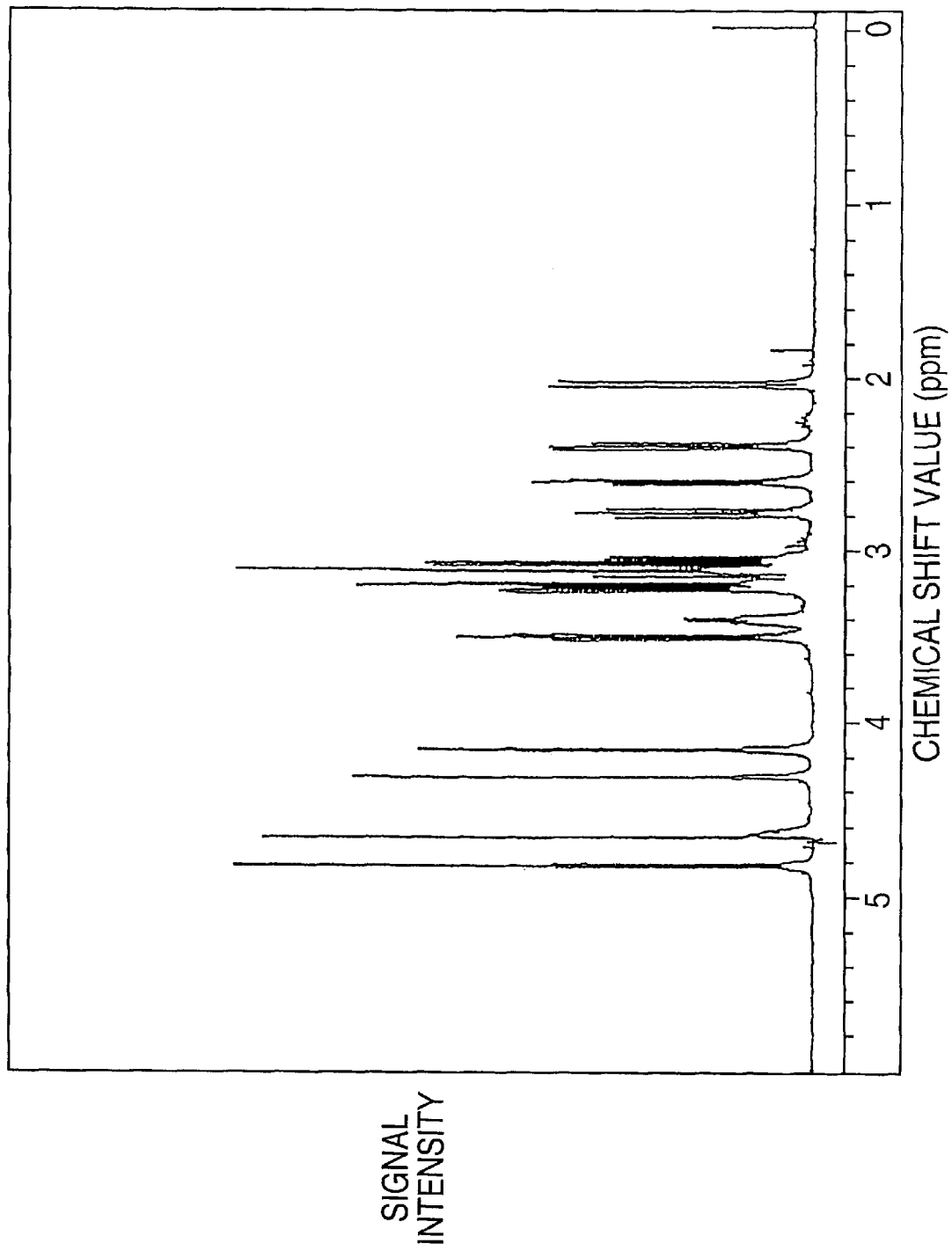
FIG. 34 shows a $^1$H-NMR spectrum of LCD1.
Figure 35:
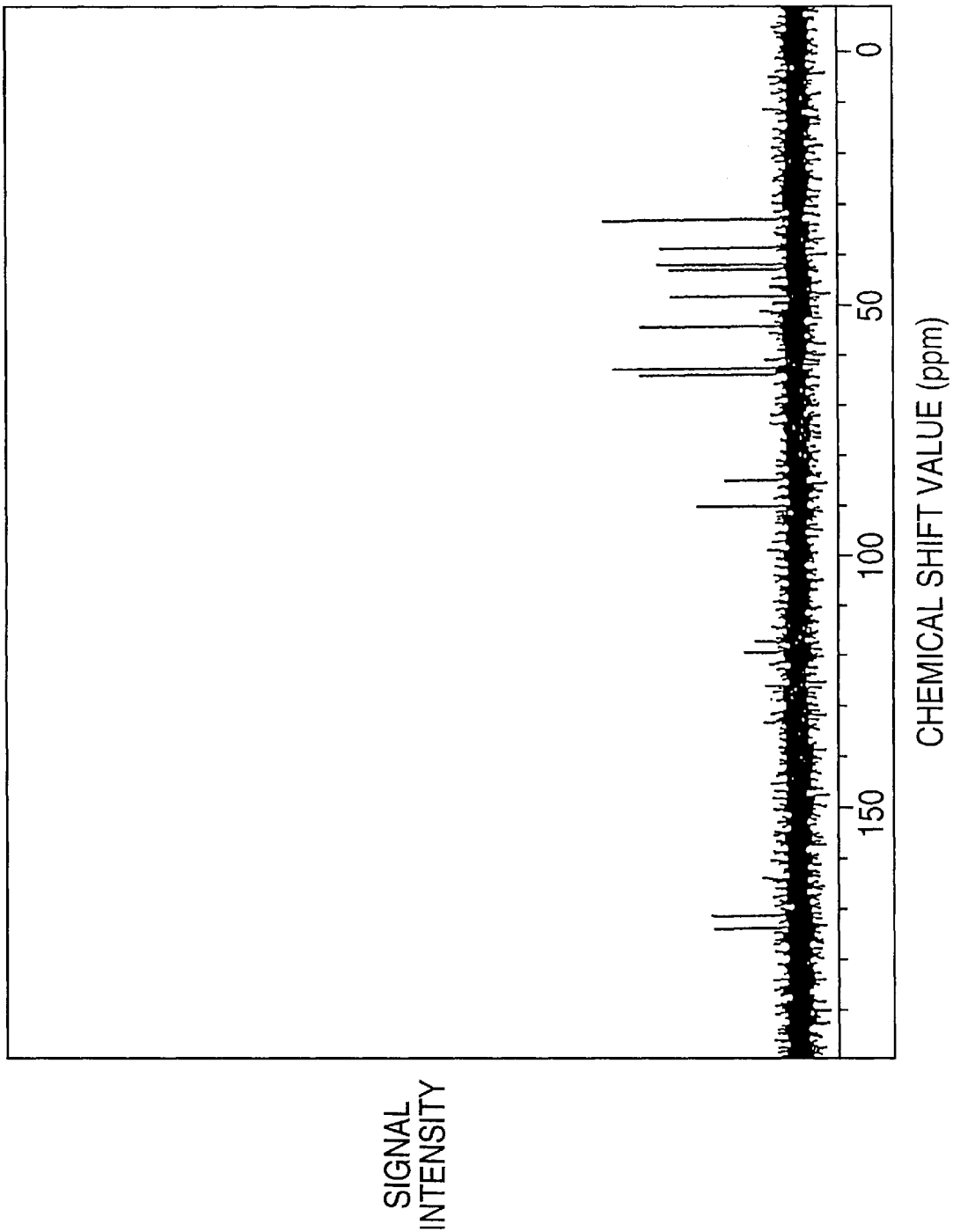
FIG. 35 shows a $^{13}$C-NMR spectrum of LCD1.
Figure 36:
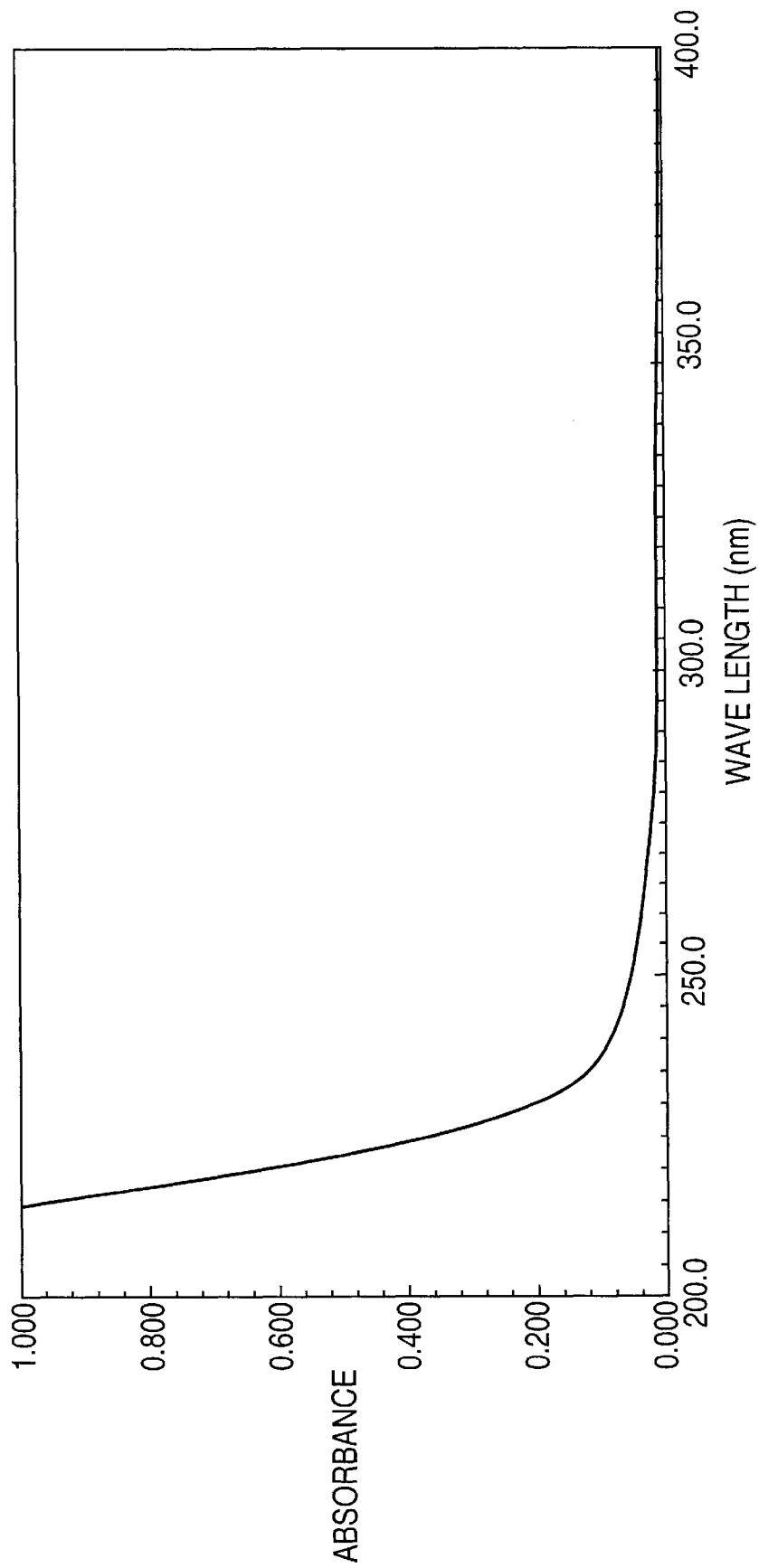
FIG. 36 shows a UV absorption spectrum of LCD1.
Figure 37:
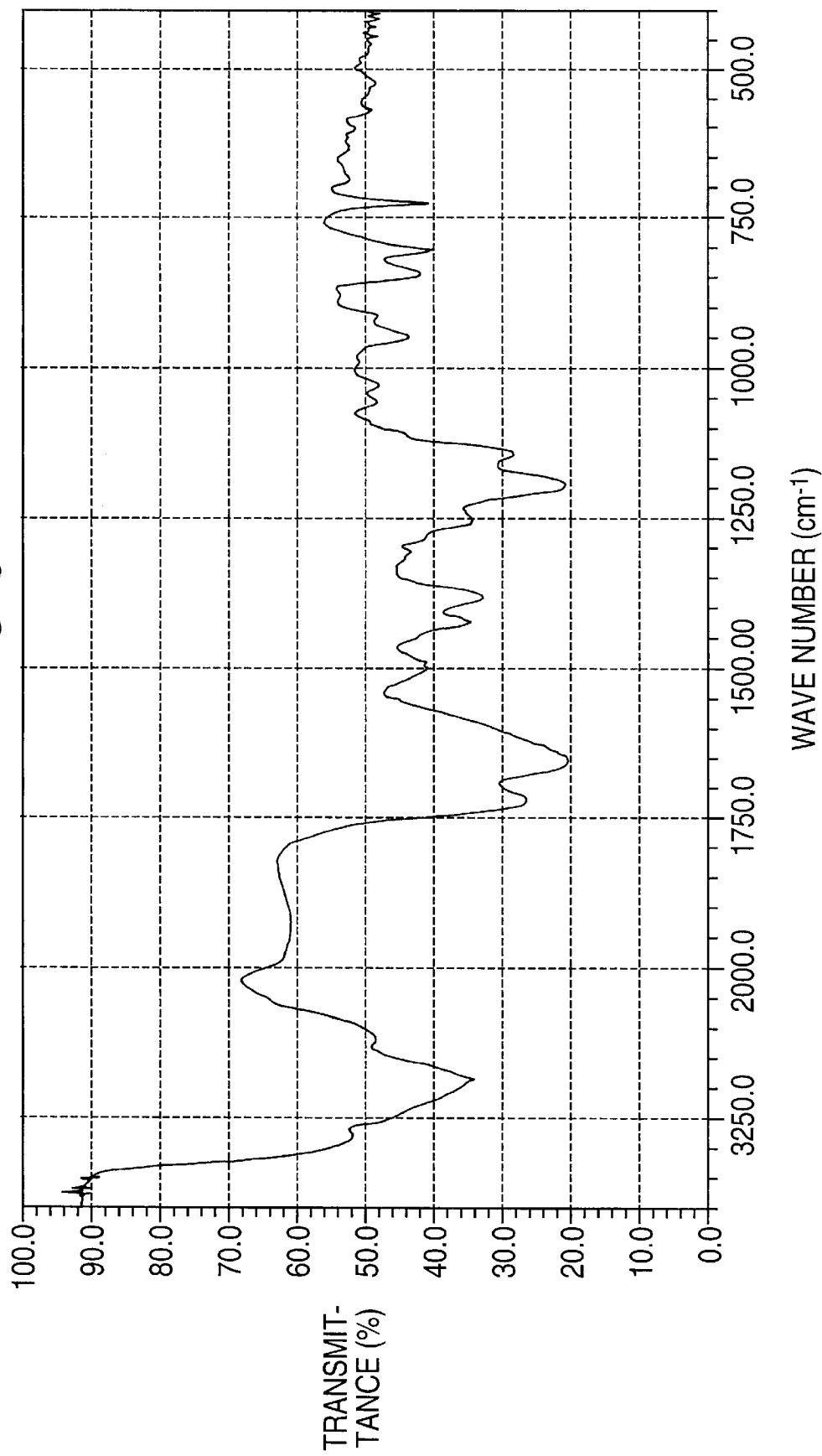
FIG. 37 shows an IR absorption spectrum of LCD1.
Figure 38:
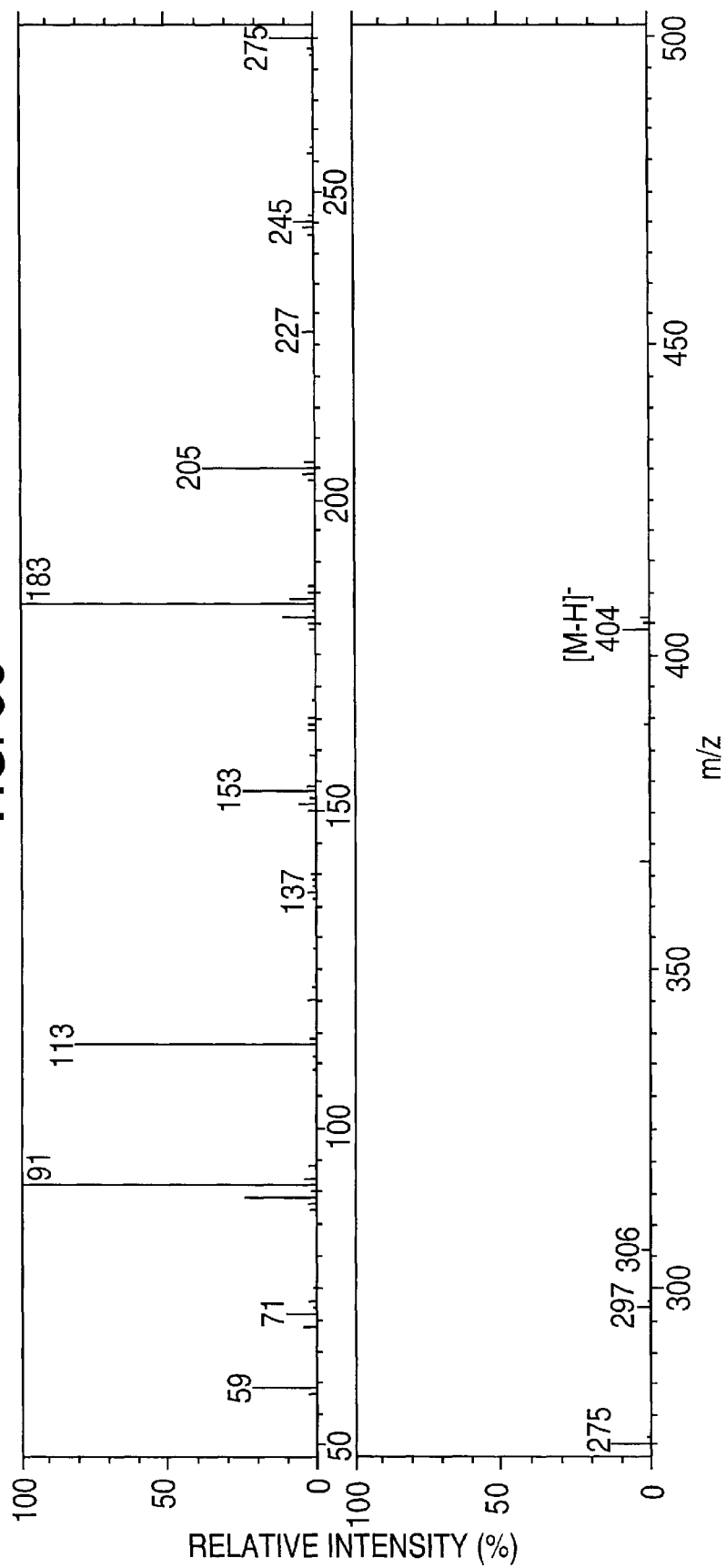
FIG. 38 shows a mass spectrum of LCD2.

The results are shown in FIG. 33 to FIG. 39. Thus, FIG. 33 shows mass spectrum of LCD1 in which abscissa indicates m/z values while ordinate indicates relative intensity (%). FIG. 34 shows $^1$H-NMR spectrum of LCD1 in which abscissa indicates chemical shift value (ppm) while ordinate indicates the signal intensity. FIG. 35 shows $^{13}$C-NMR spectrum of LCD1 in which abscissa indicates chemical shift value (ppm) while ordinate indicates the signal intensity. FIG. 36 shows UV absorption spectrum of LCD1 in which abscissa indicates wave length (nm) while ordinate indicates absorbance. FIG. 37 shows IR absorption spectrum of LCD1 in which abscissa indicates wave number (cm$^{-1}$) while ordinate indicates transmittance (%). FIG. 38 shows mass spectrum of LCD2 in which abscissa indicates m/z values while ordinate indicates relative intensity (%). FIG. 39 shows $^1$H-NMR spectrum of LCD2 in which abscissa indicates chemical shift value (ppm) while ordinate indicates the signal intensity.

Incidentally, the numbers of assignment of the signals of $^1$H-NMR and $^{13}$C-NMR are as shown in the following formula [XXI].

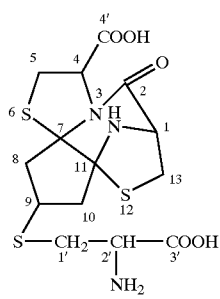

[XXI]

From the above, it has been clarified that tCD is a mixture of LCD1 and LCD2 which are in a relation of diastereomers each other and that both LCD1 and LCD2 are represented by a planar structure of the formula [XXI].

Example 18

Injection Preparations (1) Imidazolylcyclopentenone was added to a physiological saline solution (as listed in the Japanese Pharmacopoeia) in a concentration of 1% to prepare an injection preparation.

(2) Imidazolylcyclopentenone and glycyrrhizic acid were added to a physiological saline solution (the same as above) in concentrations of 0.5% and 0.1%, respectively, to prepare an injection preparation.

(3) tCD was added to a physiological saline solution (the same as above) in a concentration of 1% to prepare an injection preparation.

(4) tCD and glycyrrhizic acid were added to a physiological saline solution (the same as above) in concentrations of 0.5% and 0.1%, respectively, to prepare an injection preparation.

Injection preparation was prepared in same manner by using another apoptosis-inducing agent of the present invention.

Example 19

Tablets (1) A tablet containing 100 mg of imidazolylcyclopentenone and an appropriate amount of microcrystalline cellulose was prepared and coated with sugar to manufacture a tablet preparation.

(2) A tablet containing 0.1 mg of imidazolylcyclopentenone, 10 mg of dipotassium glycyrrhizinate and an appropriate amount of microcrystalline cellulose was prepared and coated with sugar to manufacture a tablet preparation.

(3) A tablet containing 100 mg of tCD and an appropriate amount of microcrystalline cellulose was prepared and coated with sugar to manufacture a tablet preparation.

(6) A tablet containing 0.1 mg of tCD, 10 mg of dipotassium glycyrrhizinate and an appropriate amount of microcrystalline cellulose was prepared and coated with sugar to manufacture a tablet preparation.

Tablet preparation was prepared in same manner by using another apoptosis-inducing agent of the present invention.

MERIT OF THE INVENTION

The present invention offers the compound of the present invention or an optically active substance or a salt thereof which exhibits physiological activities such as anticancer activity, activity of growth inhibition of cancer cells, apoptosis-inducing activity, activity of topoisomerase II inhibition, induction activity of the cancer cell differentiation, antirheumatic activity, activity of chronic articular rheumatism inhibition, activity of inducing the Fas antigen production, antibacterial activity, antiviral activity, activity of improving the hepatic function, activity of inducing the heat shock protein, normalizing activity of the blood components, enhancer activity of the cancer immunity, anti-inflammation activity, inhibition activity of tumor necrosis factor expression, inhibition activity of nitrogen monoxide production, immunomodulating activity such as inhibition activity of delayed type hypersensitivity, inhibition activity of lymphocyte transformation, inhibition activity of mixed lymphocyte reaction, inhibition activity of IgE production and inhibition activity of carrageenan edema. It also offers a pharmaceutical composition having physiological activity functions which contains the compound of the present invention or an optically active substance or a salt thereof.

What is claimed is:

1. A pharmaceutical composition for inducing apoptosis which contains an effective amount of the compound of formula [I] or a pharmaceutically acceptable salt thereof and a pharmaceutically acceptable carrier

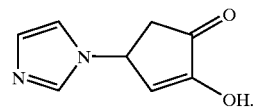

[I]

2. A compound represented by the following formula [I] or a pharmaceutically acceptable salt thereof

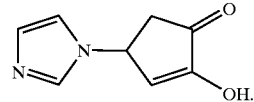

[I]

\* \* \* \* \*